(12) United States Patent
Girsh

(10) Patent No.: US 9,555,063 B2
(45) Date of Patent: *Jan. 31, 2017

(54) PLURIPOTENT THERAPEUTIC COMPOSITIONS AND USES THEREOF

(71) Applicant: IMMUNOPATH PROFILE, INC., Naples, FL (US)

(72) Inventor: Leonard S. Girsh, Naples, FL (US)

(73) Assignee: IMMUNOPATH PROFILE, INC., Naples, FL (US)

( * ) Notice: Subject to any disclaimer, the term of this patent is extended or adjusted under 35 U.S.C. 154(b) by 364 days.

This patent is subject to a terminal disclaimer.

(21) Appl. No.: 13/938,666

(22) Filed: Jul. 10, 2013

(65) Prior Publication Data

US 2014/0193368 A1 Jul. 10, 2014

Related U.S. Application Data

(63) Continuation of application No. 12/466,850, filed on May 15, 2009, now abandoned, which is a continuation-in-part of application No. 10/868,697, filed on Jun. 14, 2004, now abandoned, which is a continuation-in-part of application No. 10/765,664, filed on Jan. 26, 2004, now Pat. No. 7,790,678, and a continuation-in-part of application No. 10/752,298, filed on Jan. 5, 2004, now abandoned, and a continuation-in-part of application No. 09/639,859, filed on Aug. 16, 2000, now Pat. No. 6,974,796, said application No. 12/466,850 is a continuation-in-part of application No. 11/501,380, filed on Aug. 9, 2006, now abandoned.

(60) Provisional application No. 60/707,571, filed on Aug. 12, 2005, provisional application No. 60/577,120, filed on Jun. 4, 2004, provisional application No. 60/557,584, filed on Mar. 29, 2004, provisional application No. 60/550,797, filed on Mar. 5, 2004, provisional application No. 60/478,565, filed on Jun. 12, 2003, provisional application No. 60/493,237, (Continued)

(51) Int. Cl.

| | |
|---|---|
| *A61K 9/127* | (2006.01) |
| *A61K 35/60* | (2006.01) |
| *A61K 9/00* | (2006.01) |
| *A61K 31/726* | (2006.01) |
| *A61K 31/737* | (2006.01) |
| *A61K 35/741* | (2015.01) |
| *A61K 38/39* | (2006.01) |
| *A61K 31/198* | (2006.01) |
| *A61K 31/202* | (2006.01) |
| *A61K 35/744* | (2015.01) |
| *A61K 36/87* | (2006.01) |
| *A61K 38/54* | (2006.01) |

(52) U.S. Cl.
CPC ............ *A61K 35/60* (2013.01); *A61K 9/0095* (2013.01); *A61K 31/198* (2013.01); *A61K 31/202* (2013.01); *A61K 31/726* (2013.01); *A61K 31/737* (2013.01); *A61K 35/741* (2013.01); *A61K 35/744* (2013.01); *A61K 36/87* (2013.01); *A61K 38/39* (2013.01); *A61K 38/54* (2013.01)

(58) Field of Classification Search
CPC .. A61K 9/0095; A61K 31/726; A61K 31/737; A61K 35/741; A61K 38/39; A61K 31/198; A61K 31/202; A61K 35/744; A61K 36/87; A61K 38/54; A61K 2300/00

See application file for complete search history.

(56) References Cited

U.S. PATENT DOCUMENTS 2,710,807 A * 6/1955 Gyorgy ................. A23C 9/203
426/71
3,400,199 A 9/1968 Balassa
(Continued)

FOREIGN PATENT DOCUMENTS

WO WO 92/21752 12/1992
WO WO 97/10723 3/1997

OTHER PUBLICATIONS

U.S. Appl. No. 10/765,664, filed Jan. 26, 2004, Girsh.
(Continued)

*Primary Examiner* — Snigdha Maewall
(74) *Attorney, Agent, or Firm* — Saliwanchik, Lloyd & Eisenschenk

(57) ABSTRACT

Synthetic Stem Cell-like Tissue Healing and Regeneration Medication with Anti-inflammatory, Protein Synthesis, Enzyme Deficiency Activation and Genetic Therapy, and Anti-cancer Agent derived from a series of inventions that include these products of Biomolecular Engineering, Drug Discovery from a Biologic Periodic Table of Applied Biochemistry and Biophysics. Tissue has a self healing effect promoting tissue healing and tissue regeneration. Not only does it maintain good health but also it has been observed that the patient's blood is withdrawn from the patient and applied to the ulcer has healing qualities. Cartilage placed in a wound promotes and accelerates wound healing. The anabolic biochemical and biophysical equivalent of tissue has been found in these embodiments to have the same pharmacologic qualities, when devoid of genetic DNA mismatch and other catabolic factors including the catabolic effects of microorganism overgrowth that lacks pro-biotic qualities. The healing efficacy of these tissue components gives us further appreciation of the protective action of human tissue over and above and other than the immune protective system or perhaps an integral component part of the immune system.

9 Claims, 19 Drawing Sheets

Related U.S. Application Data filed on Aug. 6, 2003, provisional application No. 60/523,936, filed on Nov. 21, 2003, provisional application No. 60/442,278, filed on Jan. 24, 2003, provisional application No. 60/447,779, filed on Feb. 13, 2003, provisional application No. 60/448,003, filed on Feb. 18, 2003, provisional application No. 60/448,497, filed on Feb. 19, 2003, provisional application No. 60/437,939, filed on Jan. 3, 2003, provisional application No. 60/149,338, filed on Aug. 17, 1999.

(56) References Cited

U.S. PATENT DOCUMENTS

| | | | |
|---|---|---|---|
| 4,145,447 A | 3/1979 | Fisher et al. | |
| 4,562,080 A | 12/1985 | Tenn | |
| 4,752,618 A | 6/1988 | Mascioli et al. | |
| 4,857,326 A | 8/1989 | Stitt | |
| 4,871,550 A | 10/1989 | Millman | |
| 5,004,593 A | 4/1991 | Ames et al. | |
| 5,236,899 A | 8/1993 | Durette | |
| 5,397,778 A | 3/1995 | Forse et al. | |
| 5,545,667 A | 8/1996 | Wiersema et al. | |
| 5,654,337 A | 8/1997 | Roentsch et al. | |
| 5,674,853 A | 10/1997 | Forse et al. | |
| 5,739,107 A | 4/1998 | Cohen et al. | |
| 5,753,211 A | 5/1998 | Garson et al. | |
| 5,753,296 A | 5/1998 | Girsh | |
| 5,855,619 A | 1/1999 | Caplan et al. | |
| 5,902,617 A | 5/1999 | Pabst | |
| 5,904,924 A | 5/1999 | Gaynor et al. | |
| 5,958,684 A | 9/1999 | Van Leeuwen et al. | |
| 6,153,582 A | 11/2000 | Skelnik | |
| 6,197,356 B1 | 3/2001 | Girsh | |
| 6,306,908 B1 * | 10/2001 | Carlson | A61K 31/202 514/547 |
| 6,479,059 B2 | 11/2002 | Montanari et al. | |
| 6,974,796 B1 | 12/2005 | Girsh | |
| 7,147,882 B2 | 12/2006 | Girsh | |
| 7,790,678 B1 | 9/2010 | Girsh | |
| 8,119,596 B2 | 2/2012 | Girsh | |
| 2001/0046963 A1 | 11/2001 | Wenzel et al. | |
| 2002/0058065 A1 | 5/2002 | Guivarc'h et al. | |
| 2003/0152629 A1 | 8/2003 | Shefer et al. | |
| 2004/0156886 A1 * | 8/2004 | Kose | A61F 13/02 424/449 |
| 2004/0265462 A1 | 12/2004 | Carlson et al. | |
| 2005/0260181 A1 | 11/2005 | Girsh | |
| 2006/0074051 A1 | 4/2006 | Girsh | |
| 2007/0014904 A1 | 1/2007 | Girsh | |
| 2007/0037777 A1 | 2/2007 | Girsh | |
| 2007/0231402 A1 | 10/2007 | Girsh | |

OTHER PUBLICATIONS

U.S. Appl. No. 10/868,697, filed Jun. 14, 2004, Girsh.
Henschen, A. et al. "Covalent Structure of Fibrinogen" *Annals of New York Academy of Sciences*, 1983, pp. 28-43, vol. 408.
Wayman, K.I. et al. "Neurodevelopmental outcome of young children with extrahepatic biliary atresia 1 year after liver transplantation" *The Journal of Pediatrics*, Dec. 1977, pp. 894-898, vol. 131, No. 6.
Neocate Product Information Sheet, downloaded from www-shsweb.co.uk on Jul. 20, 2000, pp. 1-2.
Office Action dated Aug. 22, 2006 in U.S. Appl. No. 11/212,530, filed Aug. 26, 2005.
Office Action dated Apr. 12, 2007 in U.S. Appl. No. 11/212,530, filed Aug. 26, 2005.
Office Action dated May 21, 2008 in U.S. Appl. No. 11/212,530, filed Aug. 26, 2005.
Office Action dated Feb. 6, 2006 in U.S. Appl. No. 10/269,613, filed Oct. 11, 2002.
Office Action dated Jan. 11, 2008 in U.S. Appl. No. 10/765,664, filed Jan. 26, 2004.
Office Action dated Aug. 26, 2008 in U.S. Appl. No. 10/765,664, filed Jan. 26, 2004.
Office Action dated Jul. 1, 2008 in U.S. Appl. No. 11/073,514, filed Mar. 7, 2005.
Enig, M.G. "Fat and cholesterol in human milk" Wise Traditions in Food, Farming and the Healing Arts, a quarterly magazine of the Weston A. Price Foundation, Fall 2001, Dec. 31, 2001, pp. 1-3.
Office Action dated Jun. 6, 2008 in U.S. Appl. No. 10/868,697, filed Jun. 14, 2004.
Patt, H.M.et al. (1953) "Comparative protective effect of cysteine against fat neutron and gamma irradiation in mice" *Proc. Soc. Exp. Biol. Med.* Oct.;84(1):189-193.
Patt, H.M et al. (1950) "The effect of cysteine on the peripheral blood of he irradiated rat" *Blood* Aug.;5(8):758-763.
Straube, R.I. et al. (1953) "Studies with cysteinamine and cysteine in x-irradiated animals" *Proc. Soc. Exp. Biol. Med.* Dec.;84(3):702-704.
Patt, H.M. (1954) "Radiation effects on mammalian systems" *Annu. Rev. Physiol.* 16:51-80.
Patt, H.M. et al. (1953) "Radiation dose reduction by cysteine" *J. Cell Physiol.* Dec.;42(3):327-341.
Patt, H.M. et al. (1952) "Effect of x-rays on thymocytes and its modification by cysteine" *Proc. Soc. Exp. Biol. Med.* May;80(1):92-97.
Patt, H.M. et al. (1950) "Further studies on modification of sensitivity to X-rays by cysteine" *Proc. Soc. Exp. Biol. Med.* Jan.; 73(1):18-21.
Konstantinova, M.M. et al. (1983) "The role of endogenous glutathione in the action of sulfur-containing radio-protectors" *Radiobiologiia* Nov.-Dec.:23(6):749-753.
Patt, H.M. et al. (1949) "Cysteine protection against x-irradiation" *Science* 10:213-214.
Hall, E.J. (1994) "The discovery of radioprotectors mechanism of action" IN: Chapter 11, *Radiology for the Radiologist*, 4th Ed., J.B. Lippincott Co., Philadelphia, PA, pp. 183-189.
Product Insert. Intralipid 20%® a 20% I.V. Fat Emulsion (Rev Apr. 2000) Baxter Healthcare Corporation, Clintec Nutrition Division, Deerfield, IL 60015 USA.
Office Action dated Oct. 9, 2007 in U.S. Appl. No. 11/073,514, filed Mar. 7, 2005.
Melichar, V. et al."Nitrogen and fat balance studies and aminograms in low birth weight infants fed modified human bank milk" *Padiatrie and Padologie*, 1986, pp. 241-248, vol. 21, entire document with English summary.
Wattiaux, M.A. "19) Milk composition and nutritional value" Dair Essentials, Badcock Institute for International Dairy Rsearch and Development, University of Wisconsin-Madison, Sep. 26, 1997, entire document at web: www.babcock.wisc.edu/downloads/de/19.ed.pdf.
Martin, R. et al. "Human milk is a source of lactic acid bacteria for the infant gut" *The Journal of Pediatrics*, Dec. 2003, vol. 143, pp. 754-758.
Brooker, B.E. "The epithelial cells and cell fragments in human milk" *Cell and Tissue Research*, 1980, pp. 321-332, vol. 210.
Guerin-Danan, C. etal. "Milk fermented with yogurt cultures and lactobacillus casei compared with yougurt and gelled milk: influence on intestinal microflora in healthy infants" *Am. J. Clin. Nutr.*, 1998, pp. 111-117, vol. 67.
Meigs, E.B. et al. "The comparative composition of human milk and of cow's milk" *The Journal of Biological Chemistry*, 1913, pp. 147-168, vol. XVI, No. 1.
Office Action dated Jun. 9, 2005 in U.S. Appl. No. 10/752,298, filed Jan. 5, 2004.
Office Action dated Jan. 19, 2006 in U.S. Appl. No. 10/752,298, filed Jan. 5, 2004.
Office Action dated Jun. 28, 2006 in U.S. Appl. No. 10/752,298, filed Jan. 5, 2004.
Office Action dated May 25, 2007 in U.S. Appl. No. 10/752,298, filed Jan. 5, 2004.
Office Action dated Feb. 13, 2008 in U.S. Appl. No. 10/752,298, filed Jan. 5, 2004.

(56) References Cited

OTHER PUBLICATIONS

Campbell, J.K. et al. "Tomato Phytochemicals and Prostate Cancer Risk" *The Journal of Nutrition*, 2004, pp. 3486S-3492S, vol. 134.
Vanderhoof, J.A. "Probiotics: future directions" *The American Journal of Clinical Medicine*, 2001, pp. 1152S-1155S, vol. 73 (suppl).
Office Action dated Feb. 21, 2008 in U.S. Appl. No. 11/501,380, filed Aug. 9, 2006.
Office Action dated Nov. 18, 2008 in U.S. Appl. No. 10/868,697, filed Jun. 14, 2004.
Office Action dated Nov. 17, 2008 in U.S. Appl. No. 10/752,298, filed Jan. 5, 2004.
Office Action dated Jul. 28, 2009 in U.S. Appl. No. 10/765,664, filed Jan. 26, 2004.
Office Action dated Mar. 9, 2009 in U.S. Appl. No. 10/765,664, filed Jan. 26, 2004.
Notice of Allowance dated Oct. 14, 2011 in U.S. Appl. No. 12/872,648, filed Aug. 31, 2010, pp. 1-9.
Allowed claims in U.S. Appl. No. 12/872,648, filed Aug. 31, 2010.

* cited by examiner

| Type of aggregation Liquid crystalline phase | Geometry | Macroscopic character | Approximate HLB value | Surfactant parameter (V/al) |
|---|---|---|---|---|

Micelles
small spherical aggregates

Bilayer/lamellar phase

Reversed hexagonal phase
Rods of water surrounded
by emulsifier

Metastatic breast cancer cells
Heavily clumped mitosis maximally corresponding to low HLB reversed hexagonal phase.
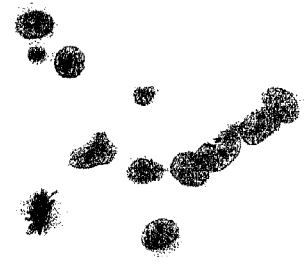
FIGURE 2A
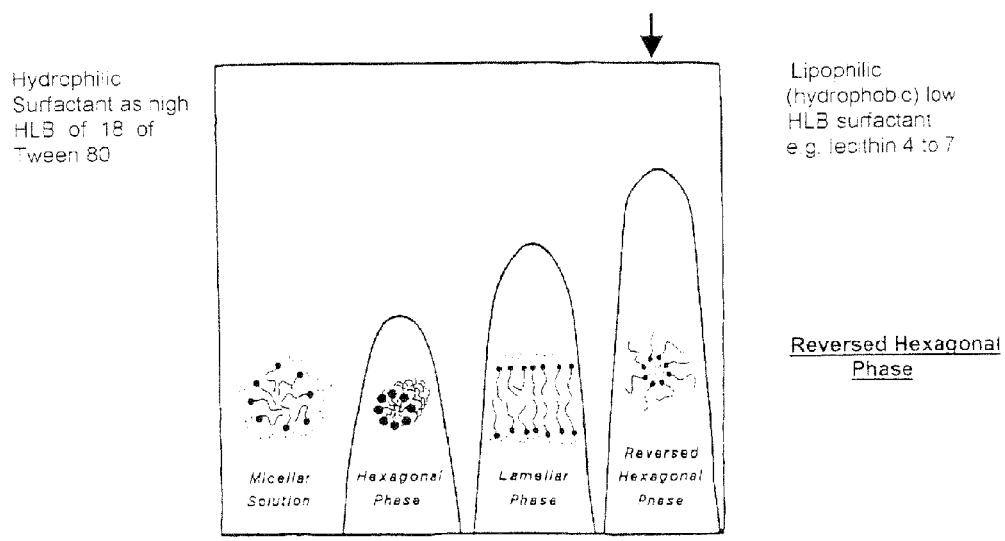
FIGURE 2B The typical sequence of phase that develops when a surfactant is mixed with water.

Indium III Abnormal radiogram of ileal inflammation.

Normalized Ileum 4 weeks after therapeutic subject composition.

| Disease | Protein | Normal Structure | Aggregate/Inclusion | Location |
|---|---|---|---|---|
| Transmissible spongiform encephalopathies (Prion disease) | Prion protein (PrP) | α-Helix and random coil | β-pleated sheet, protein-ase K–resistant | Extracellular (see Fig. 30–35D) |
| Alzheimer disease | Amyloid precursor protein (APP) | α-Helix and random coil | β-pleated sheet, amyloid (fragment of APP) | Extracellular (see Fig. 30–29C) |
| Parkinson disease | α-Synuclein | Random coil, re-peats | Aggregated, Lewy bodies | Intracytoplasmic (see Fig. 30–31C) |
| Huntington disease | Huntingtin | Trinucleotide repeats | Insoluble aggregates | Nuclear |
| Spinocerebellar ataxias | Ataxins | Trinucleotide repeats | Insoluble aggregates | Nuclear |

FIGURE 7

Placed in water

| Amino Acid | α Helix ($P_\alpha$) | β Sheet ($P_\beta$) | Turn ($P_t$) | |
|---|---|---|---|---|
| Ala | 1.29 | 0.90 | 0.78 | |
| Cys | 1.11 | 0.74 | 0.80 | |
| Leu | 1.30 | 1.02 | 0.59 | |
| Met | 1.47 | 0.97 | 0.39 | Favor α helices |
| Glu | 1.44 | 0.75 | 1.00 | |
| Gln | 1.27 | 0.80 | 0.97 | |
| His | 1.22 | 1.08 | 0.69 | |
| Lys | 1.23 | 0.77 | 0.96 | |
| Val | 0.91 | 1.49 | 0.47 | |
| Ile | 0.97 | 1.45 | 0.51 | |
| Phe | 1.07 | 1.32 | 0.58 | Favor β sheets |
| Tyr | 0.72 | 1.25 | 1.05 | |
| Trp | 0.99 | 1.14 | 0.75 | |
| Thr | 0.82 | 1.21 | 1.03 | |
| Gly | 0.56 | 0.92 | 1.64 | |
| Ser | 0.82 | 0.95 | 1.33 | |
| Asp | 1.04 | 0.72 | 1.41 | Favor turns |
| Asn | 0.90 | 0.76 | 1.23 | |
| Pro | 0.52 | 0.64 | 1.91 | |
| Arg | 0.96 | 0.99 | 0.88 | |

FIGURE 9A

1. Any segment of six residues or more, with $\langle P_\alpha \rangle \geq 1.03$, as well as $\langle P_\alpha \rangle > \langle P_\beta \rangle$, and not including Pro, is predicted to be α helix.
2. Any segment of five residues or more, with $\langle P_\beta \rangle \geq 1.05$, and $\langle P_\beta \rangle > \langle P_\alpha \rangle$, is predicted to be β sheet.
3. Examine the sequence for tetrapeptides with $\langle P_\alpha \rangle < 0.9$, $\langle P_t \rangle > \langle P_\beta \rangle$. They have a good chance of being turns. The actual rules for predicting β turns are more complex, but this method will work in most cases.

FIGURE 9B

|   | C | N | O | H |
|---|---|---|---|---|
| C | 3.20 (3.00) | 2.90 (2.80) | 2.80 (2.70) | 2.40 (2.20) |
| N |   | 2.70 (2.60) | 2.70 (2.60) | 2.40 (2.20) |
| O |   |   | 2.70 (2.60) | 2.40 (2.20) |
| H |   |   |   | 2.00 (1.90) |

FIGURE 12

| | gly | ala | ser | glu + gln | cys | pro | arg | leu | thr | asp + asn | val | hypro | hylys | tyr | ilu | phe | lys | trp | his | met |
|---|---|---|---|---|---|---|---|---|---|---|---|---|---|---|---|---|---|---|---|---|
| SILK | 44.6* | 29.4* | 12.2* | 1.0 | --- | .3 | .5 | .5 | .9 | 1.3 | 2.2 | --- | --- | 5.2 | .7 | .5 | .3 | .2 | .2 | --- |
| WOOL | 8.1 | 5.0 | 10.2 | 12.1 | 11.2 | 7.5 | 7.2 | 6.9 | 6.5 | 6.0 | 5.1 | --- | --- | 4.2 | 2.8 | 2.5 | 2.3 | 1.2 | .7 | .5 |
| COLLAGEN | 0* | 10.7* | 4.3 | 7.1 | --- | 12.2* | 5.0 | 2.4 | 2.0 | 4.5 | 2.3 | 9.4* | .7 | .4 | .9 | 1.2 | 2.7 | --- | .4 | .8 |

FIG. 14

PLURIPOTENT THERAPEUTIC COMPOSITIONS AND USES THEREOF

CROSS-REFERENCE TO RELATED APPLICATIONS

This application is a continuation of U.S. application Ser. No. 12/466,850, filed May 15, 2009, which is a continuation-in-part of U.S. application Ser. No. 10/868,697, filed Jun. 14, 2004, now abandoned, which claims the benefit of U.S. Provisional Patent Application Ser. Nos. 60/577,120, filed Jun. 4, 2004; 60/557,584, filed Mar. 29, 2004; 60/550,797, filed Mar. 5, 2004; 60/478,565, filed Jun. 12, 2003; 60/493,237, filed Aug. 6, 2003; and 60/523,936, filed Nov. 21, 2003. These applications are all hereby incorporated by reference in their entireties, including all figures, formulae, references, amino acid and nucleic acid sequences, and tables.

This application is a continuation of U.S. application Ser. No. 12/466,850, filed May 15, 2009, which is a continuation-in-part of U.S. application Ser. No. 10/868,697, filed Jun. 14, 2004, now abandoned, which is a continuation-in-part of application Ser. No. 10/765,664, filed Jan. 26, 2004, which claims the benefit of U.S. Provisional Patent Application Ser. Nos. 60/442,278, filed Jan. 24, 2003; 60/447,779, filed Feb. 13, 2003; 60/448,003, filed Feb. 18, 2003; 60/448,497, filed Feb. 19, 2003; 60/478,565, filed Jun. 12, 2003; 60/493,237, filed Aug. 6, 2003; and 60/523,936, filed Nov. 21, 2003. These applications are all hereby incorporated by reference in their entireties, including all figures, formulae, references, amino acid and nucleic acid sequences, and tables.

This application is a continuation of U.S. application Ser. No. 12/466,850, filed May 15, 2009, which is a continuation-in-part of U.S. application Ser. No. 10/868,697, filed Jun. 14, 2004, now abandoned, which is also a continuation-in-part of application of U.S. application Ser. No. 10/752,298, filed Jan. 5, 2004, now abandoned, which claims the benefit of 60/437,939, filed Jan. 3, 2003. These applications are all hereby incorporated by reference in their entireties, including all figures, formulae, references, amino acid and nucleic acid sequences, and tables.

This application is a continuation of U.S. application Ser. No. 12/466,850, filed May 15, 2009, which is a continuation-in-part of U.S. application Ser. No. 10/868,697, filed Jun. 14, 2004, now abandoned, which is also a continuation-in-part of U.S. application Ser. No. 09/639,859, filed Aug. 16, 2000 (now U.S. Pat. No. 6,974,796), which claims the benefit of U.S. Provisional Patent Application Ser. No. 60/149,338, filed Aug. 17, 1999. These applications are all hereby incorporated by reference in their entireties, including all figures, formulae, references, amino acid and nucleic acid sequences, and tables.

This application is a continuation of U.S. application Ser. No. 12/466,850, filed May 15, 2009, which is also a continuation-in-part of U.S. application Ser. No. 11/501,380, filed Aug. 9, 2006, which claims the benefit of U.S. Provisional Patent Application Ser. No. 60/707,571, filed Aug. 12, 2005. These applications are all hereby incorporated by reference in their entireties, including all figures, formulae, references, amino acid and nucleic acid sequences, and tables.

BRIEF DESCRIPTION OF THE DRAWINGS

The composition that mimics human tissue and its impact on normalization of diseased tissue.

I. Normalization of Cell Cycle.

FIGS. 2A-B. A) Illustrates (by arrows) lipophilic low HLB surfactant, and its reversed hexagonal phase micelle geometric configuration analog, to the abnormal mitosis in cancer. The typical sequence of phase that develops when a surfactant is mixed with water. Similar geometric appearance mechanism. 2A) Mitotic figure, cancer; 2B) Reversed hexagonal phase (also shown in 1C).

II. Normalization of Inflamed Tissue—Anti-Inflammatory and Immune Modulatory Effect of Therapeutic Composition.

Normalization of protein thereby reducing histamine release at the allergic response.

Figure 1A:
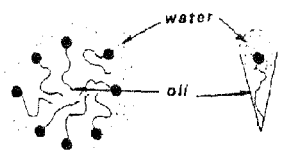
FIGS. 1A-C. Expands upon the reversed hexagonal liquid crystalline phase lipophilic micelle of FIG. 2B with an HLB of less than 6 versus intermediate HLB of 8-10 with bilayer lamellar liquid crystalline phase geometric configured micelle. Further to this comparison is another liquid crystalline phase hydrophilic micelle with the hexagonal micelle of hydrophilic HLB of more than 13. Other contrasted features include, in addition to the foregoing geometry of liquid crystalline phase aggregation and the type of liquid crystalline phase aggregation, macroscopic character, HLB range, and surfactant parameters used in in vitro embodiments with an 76% to 83% anticancer efficacy after 24 to 48 hours of contacting these compositions with cancer cells. A) Lysophospholipids (e.g., oleic acid, stearic acid) showing miscelles; —small spherical aggregates, clear solution; B) Double-chained lipids with large head group areas (anionic lipids and saturated chains, (e.g., phosphatidylcholine, phosphatidylserine) and double-chained lipids with small head group areas (anionic lipids and saturated chains, e.g., phosphatidylethanolamine, phosphatidylserine+$Ca^{2+}$) showing bilayer/lamellar phase, milky dispersion; C) Double-chained lipids with small head group areas (e.g., non-ionic lipids), showing reversed hexagonal phase and rods of water surrounded by emulsifier and showing lumps of emulsifier in equilibrium with surplus of water.
Figure 1B:
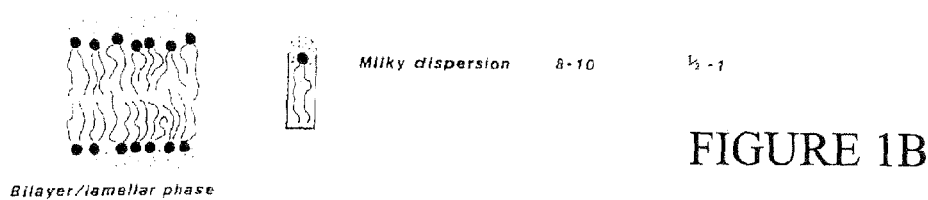
Figure 1C:
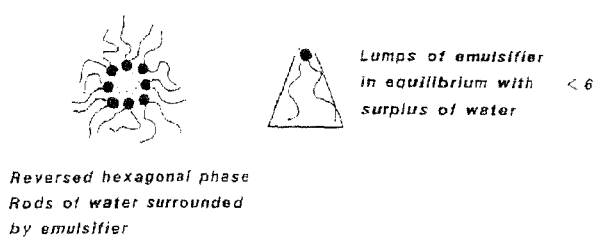
Figure 3:
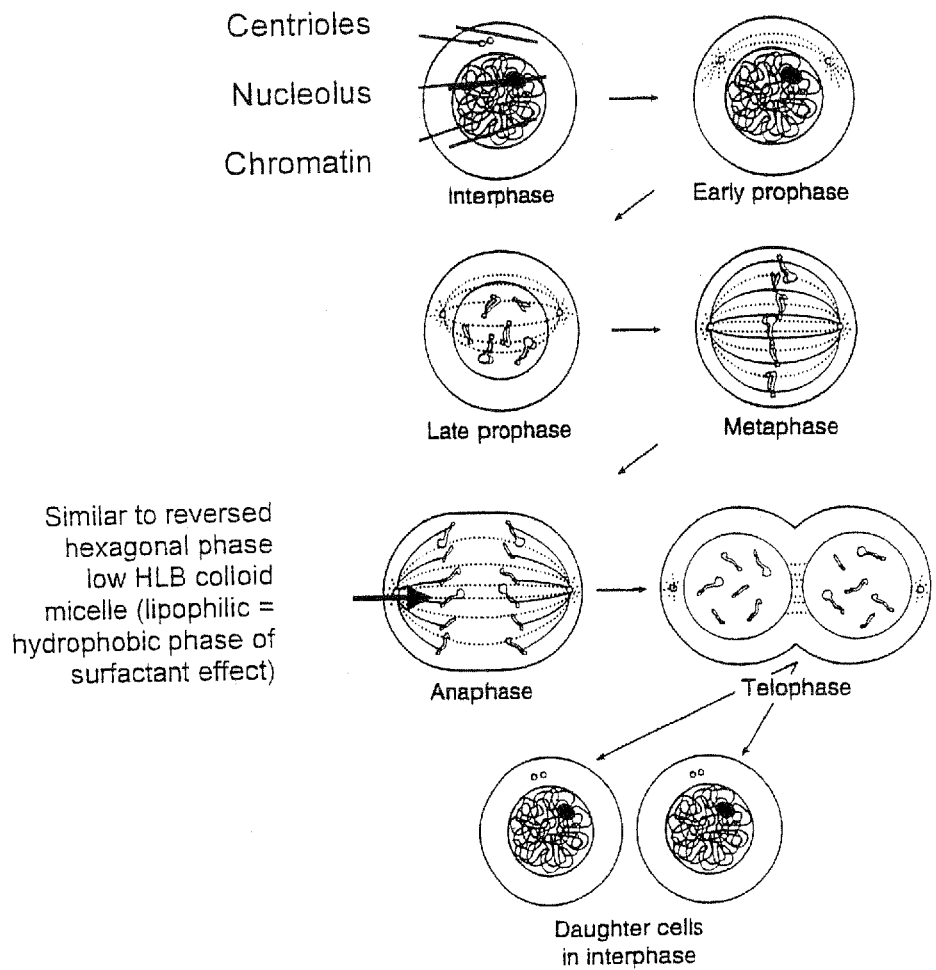
FIG. 3. Mitosis and its phases—showing Centrioles, Nucleolus and Chromatin and phase similar to reversed hexagonal phase low HLB colloid micelle (lipophilic=hydrophobic phase of surfactant effect). Genetic distribution, also mobilization of membrane of cell, cell nuclei, and intranuclear phospholipids.
Figure 4A:
Figure 4B:

FIGS. 4A-B. A) Indium 111 abnormal radiogram of ileal inflammation shown radiographically by permeability test tagged neutrophile with Indium 111 for Crohns Disease; B) Normalized ileum 4 weeks after therapeutic subject composition after subject therapeutic composition, in contrast to FIG. 4A.

Figure 5:
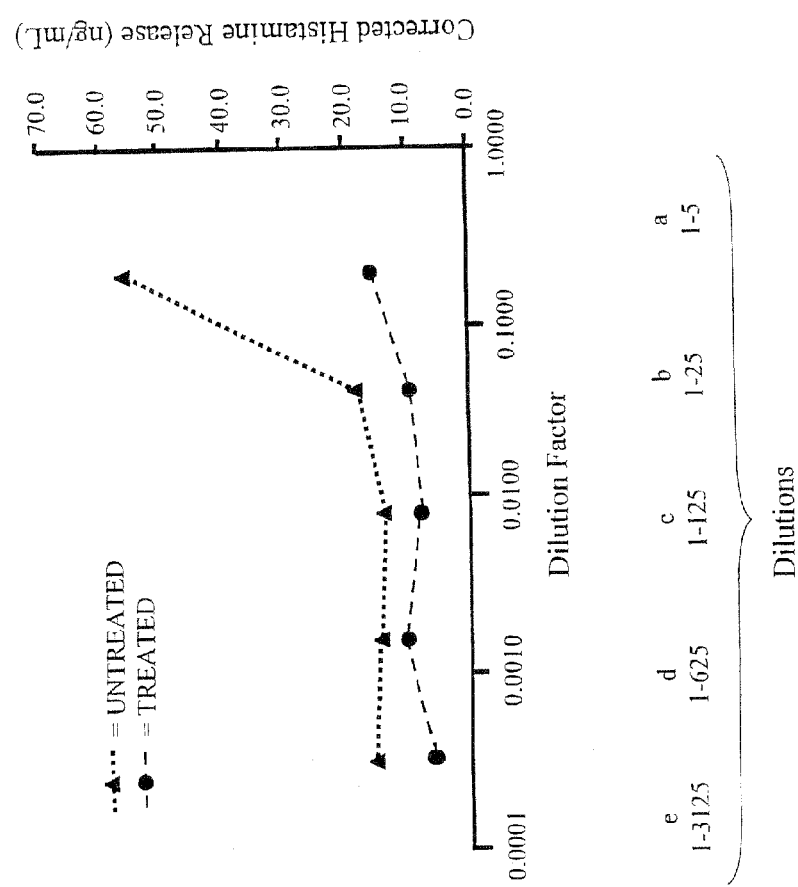

FIG. 5. In vitro basophilic de granulation measure by histamine release comparing efficacy of treated cat dander in preventing histamine release with untreated cat dander when exposed to serum from cat allergic patients. Further applications: the addition of liquid crystal formulation and its effect on the protein molecule was demonstrated in regard to the structure and folding of the macro-molecular protein antigen thereby modifying its biologic function and 3D antibody fit. This liquid crystalline formulation of processing of antigen resulted in a decrease of histamine release and abnormal response of allergy was lessened. In this case, the liquid crystalline formulation treated cat dander was compared with the untreated cat dander control, and when incubated with the patient's basophils and serum, the amount of histamine release was measured and found to be significantly lessened.

This structural change associated with reduction of allergenicity and antigenicity was further documented by specific protein polypeptide stains. Similar achievements in reduction in allergenicity have been made with allergens such as peanut, documented by RAST and Elisa studies. The peanut allergen was reduced by 285 times less (measured in picograms in contrast to the untreated controls). In the case of milk, no allergen was detectable in contrast to the untreated controls (the biologic properties of taste were not only maintained, but enhanced).

Figure 6:

FIG. 6. The prion protein. This model depicts NMR results for the structure of most of $PR^{Pc}$. The globular, a-helical region lies at the C-terminus. Most of the N-terminal region appears to be a disordered random coil. It is believed that it is this portion of the molecule that folds to produce the increase in B sheet observed in $PR^{Sc}$ and associated diseases such as Alzheimer's disease, Parkinson's disease, mad cow disease and its human variant—transmissible spongiform encephalopathies (diseases associated with abnormal dysfunctional mis-folded protein, such as prion protein).

FIG. 7. Table showing diseases associated with abnormal dysfunctional mis-folded protein such as prion protein.

Figure 8A:
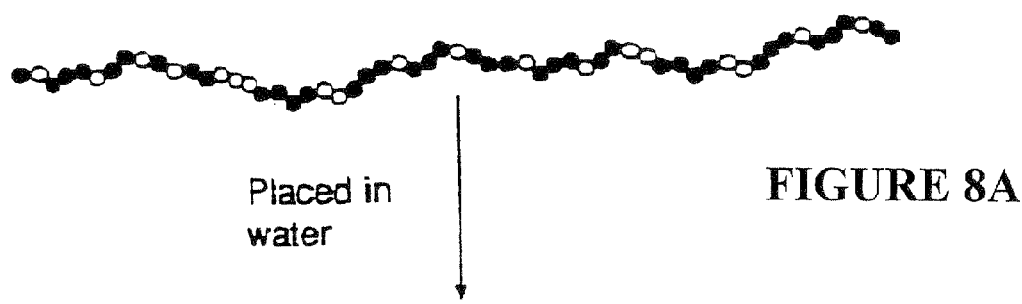
Figure 8B:
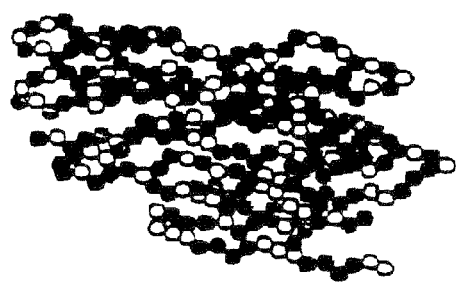
Figure 8C:
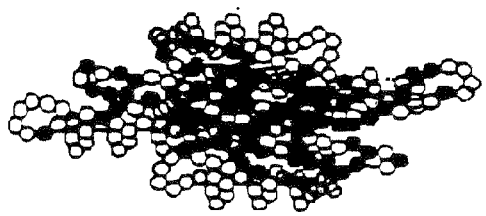
Figures 10A, 10B, 10C, 10D:
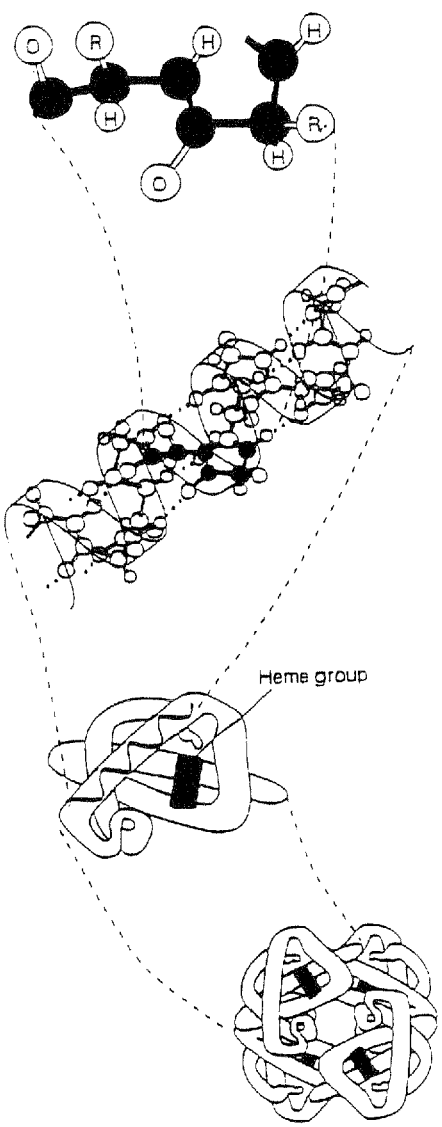

FIGS. 8A-C. Sequence of events involved in protein folding showing: A) primary sequence with black circles representing hydrophobic residues; B) collapse of the hydrophobic primary sequence to a compact structure containing minimal contacts resulting in secondary structure formation; and C) native formation, directed by obtaining a conformation with the maximum number of interchain hydrophobic contacts and by disulfide bond formation. Finally, the other forces, i.e. H-bonding, van der Waals forces and electrostatic interactions stabilize the native structure.

FIGS. 9A-B. Tables showing: A) relative probabilities of amino acid residue occurrence in different globular protein secondary structures—the pathogenic effect of structural changes that may be normalized; and B) Chou-Fasman rules for prediction.

FIGS. 10A-D. Sequence of events involved in protein folding: The 4 levels of protein structure: A) Primary structure; B) Secondary structure; C) Tertiary structure; and D) Quarternary structure. This summary of the structural levels of protein uses the HBG molecule, a tetramer of myoglobin-line chains (indicated in the bold parts of the figures).

Figure 11:
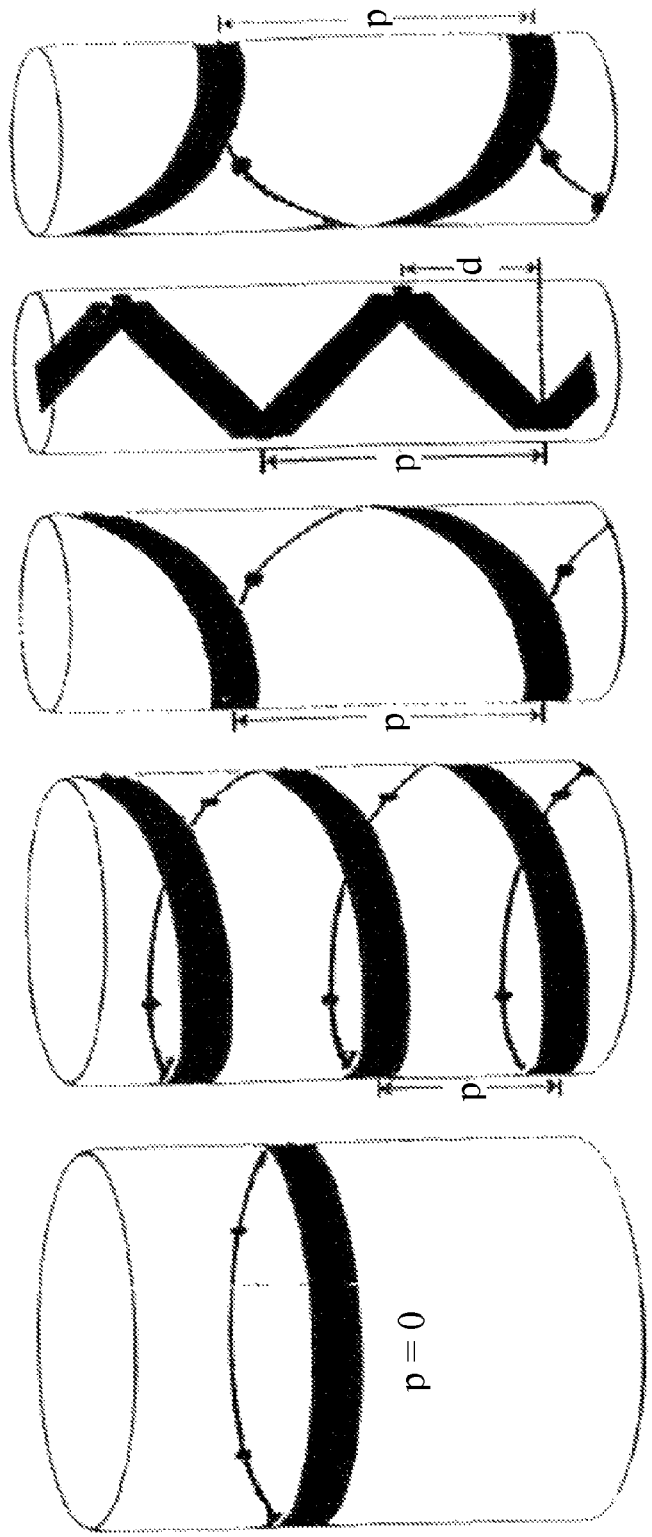

FIG. 11. Definitions of the pitch of a helix $P_1$ and the number of repeating units per turn, n. The rise along the helix axis per repeating unit is $d=p/n$. If the twists at every carbon atom are the same, then the chain falls naturally into a helix. Such helix of repeating subunits can be described by the number of units per turn of helix, n, and by the distance traversed parallel to the helix axis per unit, d. The product of these is the pitch of the helix, p. For a polypeptide chain of fixed dimensions, both n and d are determined.

FIG. 12. Minimum contact distances for non-bonded atoms. Top figure is from normally accepted van der Waals radii. Figures in parentheses are the absolute minimum values found by Ramachandran in small structures. Distances are in Å. This precision can be adapted in this liquid crystal medication system in providing therapeutic response.

Figure 13A:
Figure 13B:
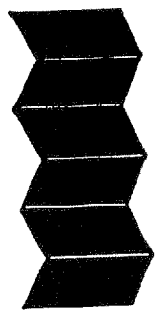
Figure 13C:

FIGS. 13A-C. Varieties of fibrous proteins. A) Alpha helix—The most familiar of the fibrous proteins are probably the keratins, which form the protective covering of all land vertebrates: skin, fur, hair, claws, nails, hooves, horns, scales, beaks and feathers. Equally widespread if less visible are the actin and myosin of muscle tissue. Epidermin is another skin component, and fibrinogen is the precursor of the blood-clotting mechanism. A second great class of proteins is the silks and insect fibers. A third class is the collagens of tendons and hides, which form connective ligaments within the body and give extra support to the skin where needed; B) Anti-parallel beta pleated sheets—These proteins are built up from three main structures: the alpha helix, the antiparallel beta pleated sheet, and the triple helix. The keratins are mostly alpha helix, with feathers in birds and some of the stiffer parts in non-mammals being a complicated form beta sheet. Myosin, epidermin, and fibrinogen are also alpha helical. The silks are the best example of the beta sheets sheet, and collagens use a characteristic triple helix; C) Collagen triple helix—Wool fibers form perhaps the best example of an alpha helical structure. They are flexible, and are extensible over a long range, up to twice their normal length. Yet they are elastic; when the tension is released, the fibers snap back again. It is just these properties that are responsible for the springiness and live feel of good wool cloth. On the other hand, the fibers are only moderately strong. The silk beta sheet structure is characterized by unusual strength, great flexibility, but low extensibility. If tension is applied to a silk fiber, rather than stretching, it resists elongation up to a point and then breaks. The collagen triple helix is quite strong, resistant to stretching and so relatively rigid. These molecular configurations of folding determine the tissue properties.

FIG. 14. Amino acid content of three typical fibrous proteins expressed in mole % of amino acids. Principal components are marked with an asterisk. Silk fibroin, wood keratin and collagen.

Figure 14A:
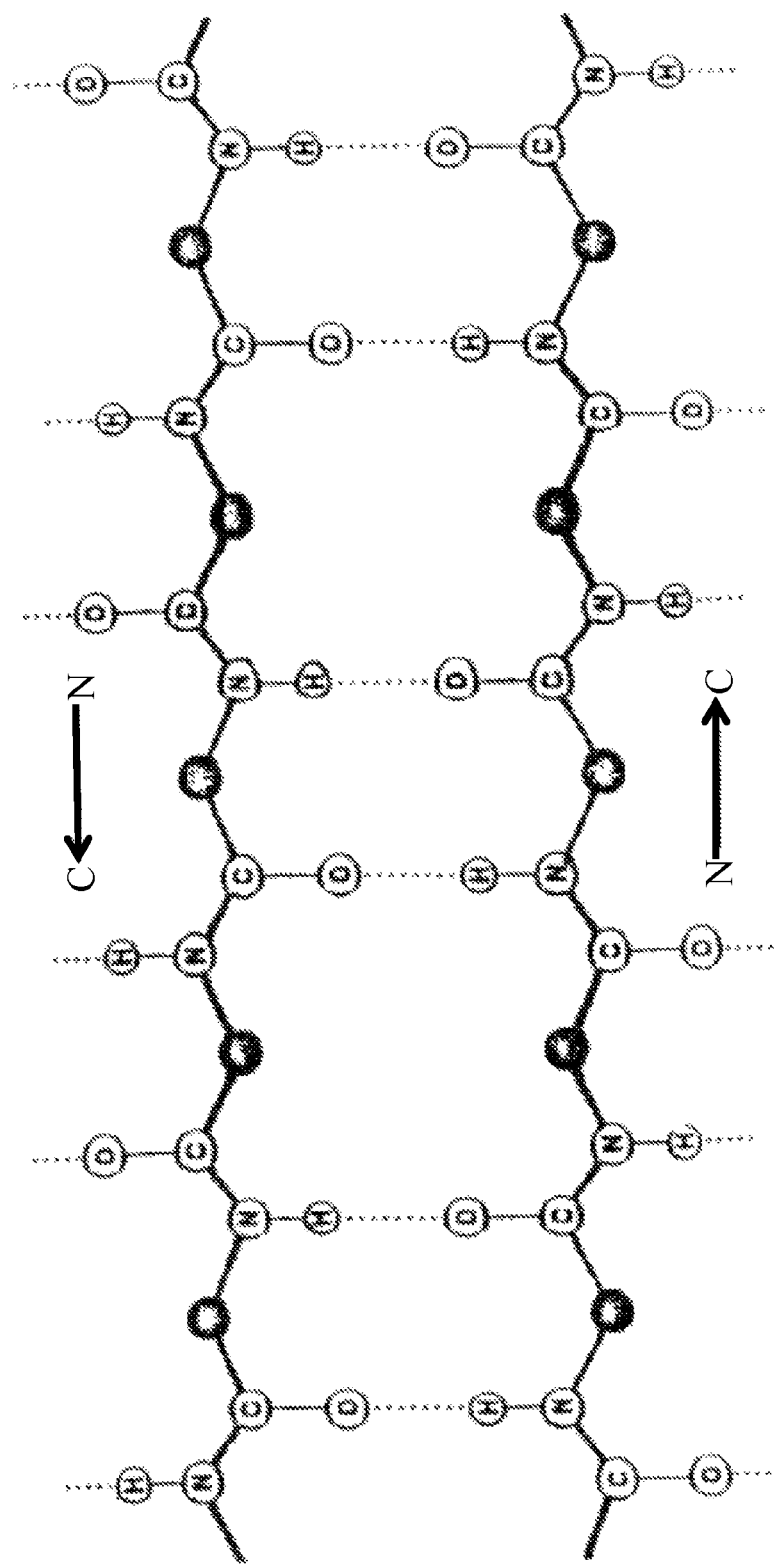

FIG. 14A. Silks and the beta sheet. Silks are built from extended polypeptide chains stretched parallel to the fiber axis, with neighboring chains running in opposite directions and hydrogen-bonded to form a sheet as shown. Pauling and Corey, 1951, called it the antiparallel pleated sheet. The need to make good hydrogen bonds keeps the chain from being fully extended. Hydrogen bonding within one antiparallel beta sheet is shown. Unterminated dotted lines are hydrogen bonds to neighboring strands in the sheet.

Figure 15:
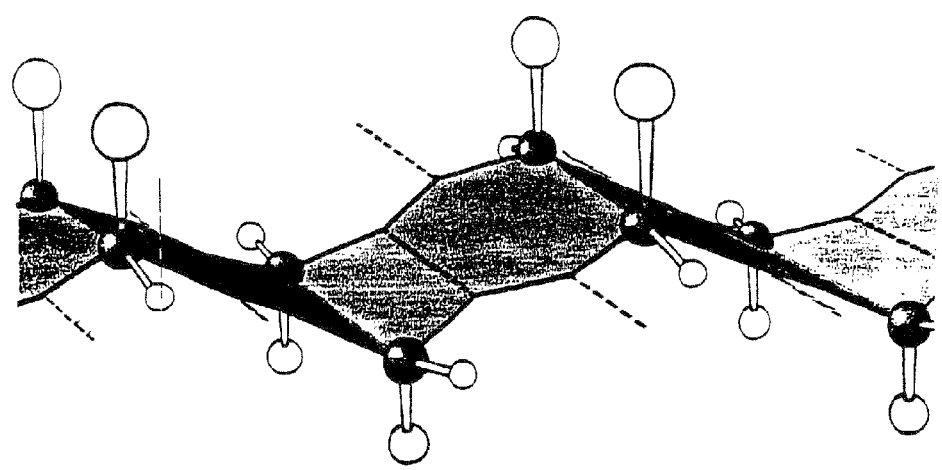

FIG. 15. Chemical sequence studies of digested silk have shown that basic six-residue unit repeats for long distances in the chain: (Gly-Ser-Gly-Ala-Gly-Ala). The result is a fiber that is very strong because the resistance to tension is borne directly by the covalent bonds of the polypeptide chain. It is not appreciably extensible, for the chain is already stretched as far as it can go without breaking the hydrogen bonds that hold the sheet together. But since the sheets themselves are held together only by van der Waals' forces between unbonded side chains, silk is quite flexible. The beta sheet is pleated or rippled, with alternate side chains extending out on either side. Dashed lines indicate hydrogen bonds.

Figure 16:
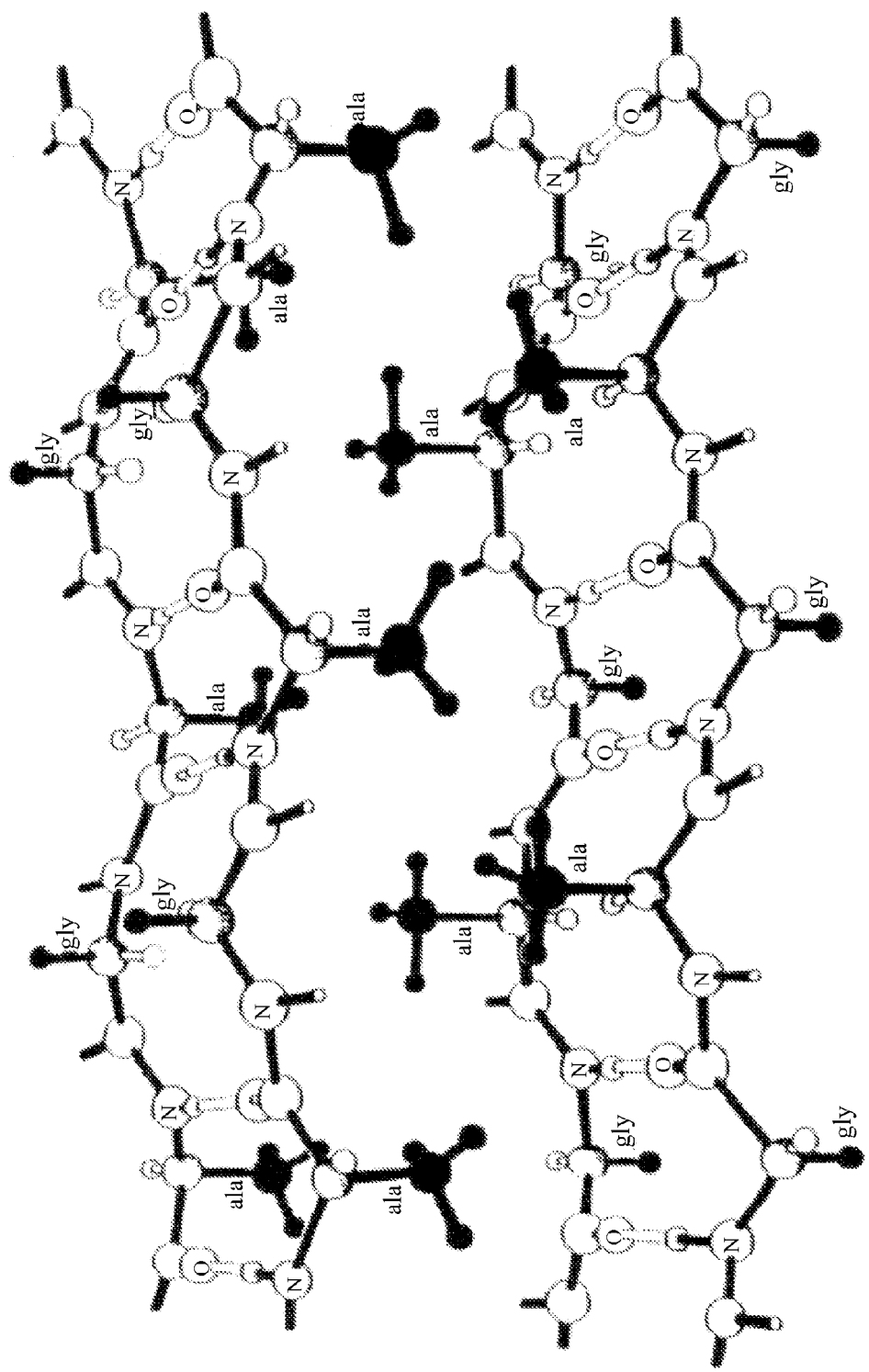

FIG. 16. The three dimensional architecture of silk. The side chains of one sheet nestle quite efficiently between those of neighboring sheets. The cut bonds extend to neighboring chains in the same sheet. There is no room in this regularity packed crystalline structure for bulky side chains such as tyrosine.

Figure 16A:
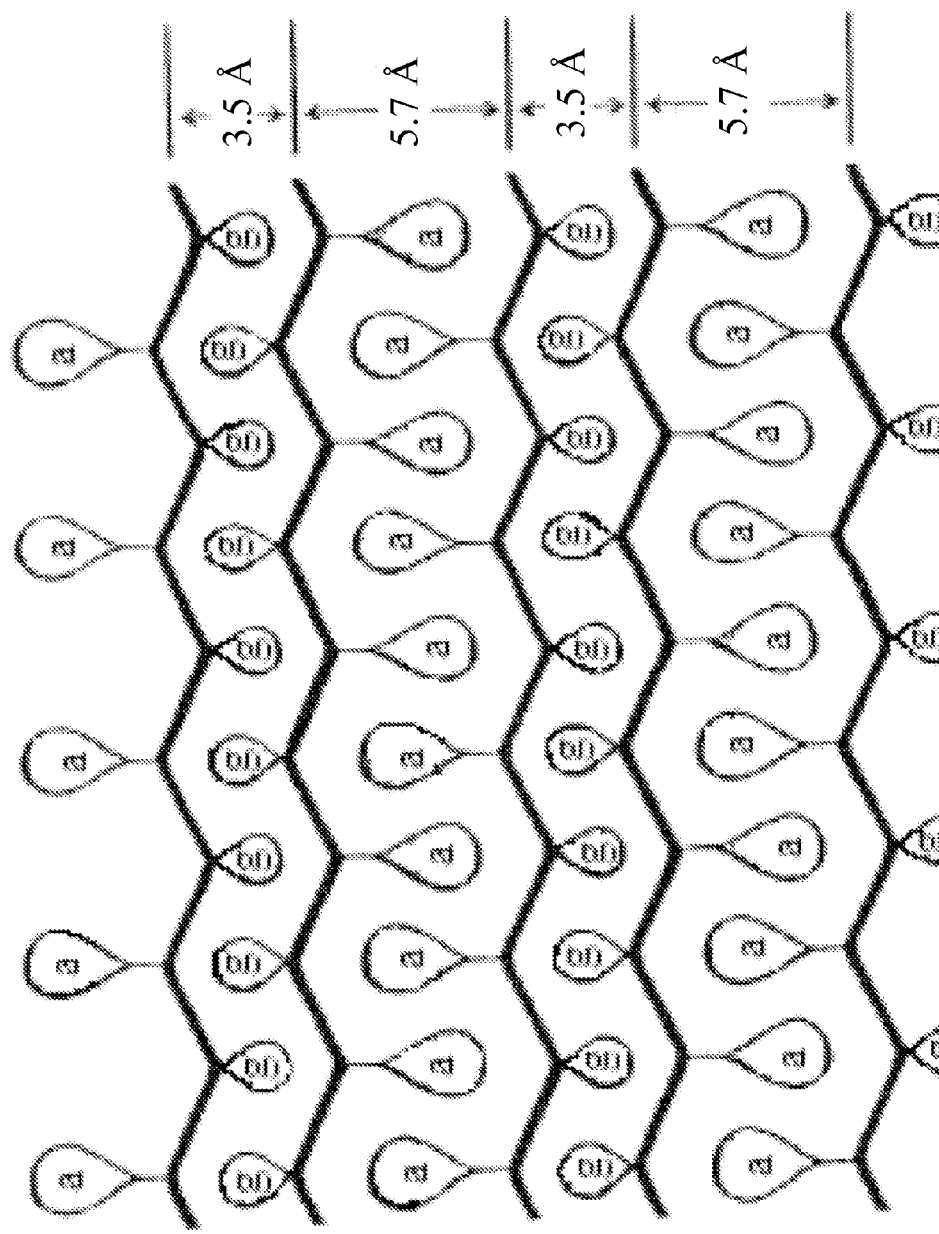

FIG. 16A. The sheets of silk are packed with ala against ala and gly against gly. The spacing between sheets therefore alternate between 5.7 Angstrom units (Å) and 3.5 (Å).

Figure 17A:
Figure 17B:
Figure 17C:
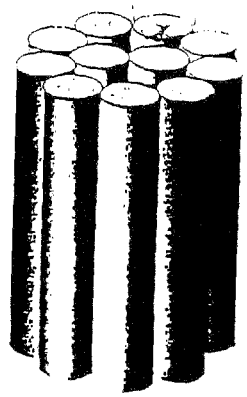

FIGS. 17A-C. Alpha ketatin and the molecular assemblage of hair keratin. A) Alpha helix; B) Protofibril; C) Microfibril. The first thoroughly studied alpha protein was the alpha keratin of wool. This commodity, of great commercial importance, prompted this analysis. The basic unit of hair keratin is an alpha helix, in about the same sense that the basic unit of a tapestry is a thread.

The weakest link is the gap between the x-ray and electron microscope evidence. The smallest features that can be seen in the best micrographs are tiny "protofibrils", 20 Å in diameter, running the length of the hair. The x-ray diffraction pattern shows that alpha helices must be present, yet these small protofibrils are too large to be alpha helices.

BACKGROUND OF INVENTION

In prior art, the treatment of disease centers around the position to "kill" as if we are trying to kill an infectious agent. This is exemplified by the discovery that platinum kills bacteria. Many of the leading cancer products of prior art are derivatives of platinum (or similar toxic products derive from the periodic table) such as but not limited to cis-platinum and carbo platinum.

It would be desirable to surmount the awesome challenges of disease treatment by restructuring diseased tissue with biochemical and biophysical components of normal tissue, which have the associated features of restructuring, healing and regeneration of organs and tissue to their normal status. This series of inventions mimic, in analog fashion, human tissue and thereby draws from normal molecular structured biochemicals with required biophysical function and from pharmacopoeia from major industrialized countries.

This has been so accomplished with results which include a therapeutic stem cell like composition which by simulating, accelerating and facilitating stem cell healing increases the tissue regeneration capacity of the patient's stem cells, thereby reversing diseases of great severity and complication. For example, organ failure can be reversed without resorting to such extreme measures of desperation and gravity, including organ transplant or tissue graft. As result of this unique focus and sourcing the associated risks and objections of dependency upon the use of human tissue and human embryonic tissue is not required.

This inventor has observed that tissue has a self healing effect promoting tissue healing and tissue regeneration. Not only does it maintain good health but also it has been observed that the patient's blood is withdrawn from patients with a leg ulcer and the blood is then applied to the ulcer the blood is shown to have healing qualities. Cartilage placed in a wound also promotes and accelerates wound healing, exemplifying the function of Component No. 3. The anabolic biochemical and biophysical essence and equivalence of tissue has been found in these embodiments to have the same healing and tissue regeneration pharmacologic qualities, when devoid of genetic DNA mismatch and other catabolic factors including the catabolic effects of microorganism overgrowth that lacks pro-biotic qualities. The healing efficacy of these tissue components gives us further appreciation of the protective action of human tissue over and above (and other than) the immune protective system or perhaps an integral component of the immune system.

The components are most effective when freely available to the metabolic stream and thereby overcome the disease producing debris of disease and crystal seeding effect obstructive and foreign to the metabolic stream. Mismatching is further assured by adherence to tissue equilibrium particularly applied here the hydrophilic/lipophilic balance HLB equilibrium. Therapeutically, through polar surface active lipid surfactants permits the tissue to maintain the unique required strata of alternation of hydrophilic with hydrophobic components such as lipids.

This strata is analog to the earth's strata exemplified by the hydrophobic nucleus surrounded by hydrophobic cytoplasm further surrounded by lipophilic cell membrane and the strata is finalized with a hydrophilic extracellular matrix. The same patterned alternate strata can be seen in the biomolecular macromolecules of proteins with the lipophilic central core derived primarily from the essential amino acids surrounded by the hydrophilic periphery of primarily non-essential amino acids further forming and attracting a clathrate cage of structured ordered non-random, non-liquid water accounting for the alpha helix or beta sheet folding and associated and dependent biologic structure and function.

It has been found in these embodiments that high HLB surfactant treatment alters the allergenicity of cat protein's 3-D structure and pathogenicity.

These same biophysical features provide the opportunity to use highly hydrophilic surfactants with their high surfactant packing parameters to provide, through hydrogen bonding, a clathrate cage of structured water and energy input and change in entropy that enhances refolding of the misfolded proteins and protein derangements and aggregates that are pathophysiologic and pathogenetic basis for diseases such as Alzheimer's disease, Parkinson's disease, Mad Cow disease and its human equivalent transmissible spongiform encephalopathy. It is this tissue essence and this biochemical and biophysical molecular engineering that has resulted in therapeutic efficacy combined with bio-safety offering therapeutic opportunities that have been otherwise not forthcoming.

The prior art teaches a passive relationship, between the genetic code and amino acid structures. However, the prior art does not teach the use of therapeutic compositions for actively enhancing and normalizing functional aspects of the cell nucleus and cytoplasm in disease to stimulate, facilitate, and accelerate protein synthesis in diseased organs and tissues.

Therapeutic stimulant, activator and substrate compositions that provide therapy for hereditary diseases and conditions of hereditary pre-disposition were disclosed in provisional Patent Application Ser. No. 60/149,338, filed Aug. 17, 1999 and are described in co-pending, U.S. patent application Ser. No. 10/269,613, filed Oct. 11, 2002 (each of which is hereby incorporated by reference in their entireties). As there disclosed, molecular monomers having alpha amino- and alpha carboxylic groupings similar in molar ratio of the component amino acid monomers in human tissue and in accordance with the specific code of the 20 amino acids of human tissue can be used for the treatment of diseases.

This unique drug discovery technology and characteristics of therapeutic synthetic stem cell-like composition is unique to the prior art is a healing tissue regenerative therapy and has been shown to be effective in averting organ graft in the replacement of disease ravaged tissue whether inflammatory, acute, chronically inflammatory, degenerative, neoplastic or genetic pathogenesis or etiologic on the basis of mimicking and analog model of human and mammalian tissue. This anabolic tissue copy basis is not only a biochemical copy, but also a functional bio-physical model copy of normal tissue function, with meticulous avoidance of catabolic components, derived from a unique biologic periodic table. The subject composition also permits reorganization as if the disease were analog to a "bankruptcy" major deficiency with replenishment not only of the tissue, but even of its trace elements, vitamins and minerals. Additionally the diseased organ or tissue secretions also represent a biochemical and biophysical copy for therapeutic normalization of these secretions.

In producing these copies we have also copied the fluidity of function by mimicking and preparing an analog copy and therefore normalizing the hydrophilic lipophilic (HLB)

equilibrium balance, with HLB (with intramolecular OH$_2$/CH$_2$ ratio of these embodiments exemplified by intramolecular composition Tween 80) surfactant energy input and associated change in entropy along with any defective human and mammalian tissue equilibria.

In so doing, not only the tissues, cells but even the microscopic and sub-microscopic structure and functions of the cell organelles undergo normalization of mitosis and apoptosis ideally characterized for anticancer therapy. The further normalization of mitosis includes the mitotic organizing centers of centrioles, peri-centriolar clouds, spindles, chromosomes and centromeres (kinetochores) of the chromosomes, acting like seeds of crystallization in conjunction with the microtubules and associated protein with tubulin tread milling polymerization. The mitotic associated tubulin protein of the microtubule has a double origin, the centriolar poles and the chromosome.

This nanogram and picogram pursuit of repair is all based on the atomic and molecular level of human tissue function as illustrated by Component Nos. 1, 2, 3, 4, and 5 of the composition of the subject invention.

We find sequential to the foregoing a bio-computer signaling system based on the semi-conductivity bio-computer inter-molecular, therefore intercellular and inter-tissue signaling system of all components of No. 1 and No. 2 and some components of No. 3. The functional biophysical overlapping of these three components is the polar surface active lipid surfactant intrinsic to these foregoing components of an emulsifier the expansion of biochemical surface area interaction by surfactant packing parameters and emulsion system, and most importantly thereby a control of fluidity, metabolic fluidity, metabolism electrochemical charge buildup and enhancement and signaling based on common semiconductor bio computer functionality and obviating, correcting, avoiding crossroads of disease. ECM component No. 3 offers the proteoglycans complex aggregate to support the colloidal system with similar architectural structural support of structured water, viscosity and lubricant effect of the synovial membrane joints and vitreous helping to hold the respective retina and umbilical blood vessels in place and unobstructed analog to the cell membrane phospholipids of component No. 2, with hyaluronidase serving as a "colloidifier" analog to a high HLB emulsifier to adjust or reduce and "thin" viscosity to enhance flow.

This fluidizing effect converts roadblocks of disease such as crystals of calcium, cholesterol, uric acid, pigment, disease debris and exogenous crystals such as, but not limited to, silica and asbestos, all acting as disease producing microscopic shards or 'thorns' sticking in the metabolic throat and sides of the patient's tissue.

The anti-inflammatory effects associated with all three components anti-inflammatory bio physiologic activities and accompany protein synthesis of components one and two (such as lysolecithin protein synthesis stimulus effects of PC of component two) as but not limited to the contrasting tetrahedral alpha amino acid non D, Levorotatory amino acids and non-chiral glycine with proteins tissue fits of these tissue 20 specific to the genetic code amino acids in sharp contrast to the aromatic benzene ring derivatives that do not fit with other anti-inflammatory drugs and therefore also interfere with protein synthesis. Medication side effects are less when co-used with subject composition. Enhancement of enzymatic activity associated with surfactant packing parameters and companion increase in vital zeta potential with use of high HLB surfactants.

The foregoing can be exemplified by non-intrusive, bio-safe, non-coalescent compositions comprise component No. 1, anabolic-non-dextrorotatory ("non-D" L amino acids, including but not limited to L-amino acids and non-chiral glycine); component No. 2 (one or more cell membrane components formed by self-vesiculating surface-active polar lipids such as but not limited to phosphatidyl choline (PC) that forms the double layer of the mammalian cell and nuclear membranes), and component No. 3 (extracellular matrix material such as collagen, proteoglycans, chondroitin sulfate, or mixtures thereof).

These therapeutic compositions are abundantly supplied and are formulated to contain amino acids in amounts that correspond to molar ratio of amino acids in a damaged organ, tissue, or protein. The amounts of each component can be adjusted to match the nature of the organ or tissue being treated. In reversing disease through this series of inventions, major side effects can be greatly minimized with co-use or sole use with these therapeutic compositions.

It is not only in the applied biochemistry and its associated biomolecular structures but also the biophysical surfactant functions including surfactant packing parameters and particle charge of these three component compartments and particularly the key to this fluid dynamics fluidizing and hydrophilizing therapy (also present in components one and three with the most concentrated surfactant function in two) can be poignantly modulated even with the challenge of modulating and thereby normalizing the abnormal mitosis of cancer through the biophysical function and structure of the polar surface active lipids in component number two along with maturation factor of ethylene oxide Tween 80 component never two. The amount of surface-active polar lipid to include in the composition can be determined by viscosity measurements. Tissue concentration can be measured by viscosity (as used in blood serum which normally is 1.12 to 1.22 centipoise with upper limit of three). In the case of the intermediate HLB 8 to 11 (as exemplified by PC phosphatidyl choline when so used) circulation is improved 25% however there is no change in viscosity or the red blood cell sedimentation rate at these HLB ranges because of the fact that biophysical functional effects is upon the cell membrane. With its use the red cell membrane becomes more plastic, and is made more pliable thereby enhancing circulation and oxygenation.

Providing a polar surface active lipid liquid crystal surfactant of extreme HLB to overcome the disturbed fluid balance and lack of fluidity of the biophysical inertia of the non metabolizable necrotic debris of the disease process results in a crystal (such as but not limited to calcium phosphate crystal where the phosphorylase enzyme which in turn releases phosphate to produce the insoluble salt deposit of calcium phosphate).

MRI crystalline calcium salts detected by MRI in the coronary artery may make stress testing not necessary. And biochemical models so derived from the crystallization requirements (as historically in the case out of the x-ray diffraction study of the DNA molecule) may lead to the biomolecular engineering model of life but the possibility of the disease variant of life (in contrast to normal model of life) must be given serious contrasting consideration.

Other intracellular and tissue body deposition responses include the lipid cholesterol crystal found in atherosclerosis and coronary artery disease whereby the lipid crystal has a melting point of 50 degrees higher than normal body temperature. Other solid crystal responses included poorly soluble uric acid crystal deposits derived from purine metabolic products or exogenous derived silica crystal and asbestos bodies and other difficult to process shards resistant to fluidity necessary for normal metabolic processing. These perpetuating foreign substances promote chronic inflammation, chronic granulomatous reactions, and in certain situations (such as but not limited to asbestos) may progress to cancer after a long period of deposition (which may be as long as 20 years). In this debris may included poorly attainable or derivable processing due to lack of metabolic tools (such as but not limited to in the case of a carbohydrate and glycogen trapped as polymerized glucose form of energy not obtainable from glucose because of the lack of insulin receptor response as in the case of Type II diabetes or deficiency of enzymes as in the case of "storage diseases"). In the case of trans fats, it has been observed to be associated with Type II diabetes with poor insulin receptor response even though production of insulin is adequate. Hereto it is likely that trans fat deposits, without adaptable trans fat enzymes, and again with 40 to 50 degrees melting point higher than body temperature may be amenable to dispersement of the fat with low HLB surfactant followed by further fluidizing the fat with the high HLB surfactant.

Protein, when misfolded, loses its biologic function in diseases such as Alzheimer's disease, Huntington's disease, and Mad Cow disease with resulting neuropathologic response of tangles, which also may be seen with lead poisoning and metals such as aluminum and zinc that are under consideration for their involvement with Alzheimer's disease.

The extracellular matrix material of Component No. 3 can include, in addition to collagen and elastin, cartilage derived from tracheal rings (of bovine or shark origin) and complex aggregates of very large macromolecule straight chain amino polysaccharide hyaluronic acid polymers of glucosamine and glucuronic acid covalently linked to (proteins and core proteins) and non-covalently linked to chondroitin sulfate.

The function of these extracellular matrix compounds include architectural integrity, imbibing of water as a biocolloid, serving as a lubricated surface (as exemplified by the synovial membranes (and rationale for a therapeutic application in regard to arthritis) and maintenance of viscosity analog to component number two the polar surface active lipids such as but not limited to phosphatidylcholine with an HLB of 10 to 11. Hyaluronidase has been looked upon in the body and therapeutically as a fluidizing, viscosity reducing, thinning enzyme with analog effect of high HLB (15 to 20) surfactants (such as but not limited to Tween 80 and sodium lauryl sulfate).

A 48 percent inhibition of calcium oxalate urinary tract stone formation was observed in a multi-center study of more than 120 patients given glycoaminoglycans sulfated polysaccharide. The remaining patients formed stones that were smaller and more readily removable in regard to crystal cell adhesion. Similar effects with ECM on blood rheology was noted as with extreme of HLB response with reduction of blood viscosity and lipids as well as anti-coagulant effects.

In other multi-center studies more than 100 patients showed significant improvement in wound healing with a 48% increase in tensile strength of healed wound. Similar effects were noted in controlled animal studies.

Optional components for the compositions of the subject invention, include, but are not limited to, non-hydrolysate-derived milk substitutes (free of catabolic products and D amino acids such as microorganism, derived sources). When used in patients with clinically suspected milk allergy or bronchial asthma respiratory tract allergy (such as nasal allergy and hay fever (documentation with allergy skin testing is usually nonproductive)), the patients respond to this therapeutic composition, which may in terms of therapeutic rationale and mechanism response, most probably also reside in the anti-inflammatory action, immune modulatory effects completely free of side effects such as commonly seen soporific effects of the antihistamines used for allergic rhinitis, or the side effects of antiasthmatic sympathomimetics and corticosteroids. Also as stressed when used in conjunction with these anti-asthmatic, anti-allergic medications side effects are greatly minimized. This is exemplified by the avoidance of common soporific side effects seen with antihistaminics. As with all these therapeutic applications, their co-use with medications lessens the dosage and the associated side effects.

Catabolic products are avoided or absent from the compositions, especially chiral amino acids and racemic mixtures containing amino acids in D form, as well as, e.g., cyclosporin oligopeptides and bacterial cellular walls. More severe complications of allergic and hypersensitivity diseases may include autoimmune disease such as lupus erythematosis and medication reaction induced false lupus. False lupus has responded to these therapeutic compositions including the collagen proteoglycan aggregate cartilage, chondroitin sulfate complex, thereby avoiding the risks of cortico-steroids, commonly required in these patients, particularly in those patients with the complication of pericardial infusion.

The compositions can also optionally incorporate material that includes stem cells or materials derived from after-birth tissue such as placenta and umbilical cord. The compositions can also include materials that correspond in amino acid composition to mother's milk or to other materials encountered during fetal and infantile development.

The compositions of the invention also mimic mother's milk or embryonal tissue. This embryonal tissue simultaneously mimics healing tissue, associated with such diseases as inflammation and tissue damage such as trauma, at the same time mimicking and being analogous to mammalian and particularly the human stem cell.

In addition, vitamin D supplied in this therapeutic stem cell subject composition and the case in toxic heavy metals would drive and sequester these heavy metals such as not limited to lead into the bones by their chelating; effects thereby greatly minimizing their neurologic toxic effects.

Additionally, vitamin D can optionally be added to further direct this enzyme therapy to the bone marrow involved in lysosomal storage disease encroachment on the bone marrow. If therapeutic replacement enzymes are not available, high HLB surfactant such as but not limited to Tween 80 or sodium lauryl sulfate 0.125% to 1% or 10% to 50% of the LD 50 in normal animals with normal HLBs.

In this therapeutic composition can further comprise phosphatidylcholine (PC), commonly derived from the soybean plant by degumming followed by acetone extraction. The highest concentrations of PC are present at birth during youth and young adult phases of life and then decreases progressively until old age. Premature infants are particularly prone to atelectasis or lung collapse, respiratory distress syndrome of the newborn and may be contrasted with full term infants that have adequate PC levels. The sudden rise in saturated PC at 34 to 36 weeks of gestation marks the development of fetal lung maturity. The phospholipids produced represent most of the lipid produced the majority of which is lecithin-saturated PC up to 85 percent of the lecithin, 60 percent of the lecithin is dipalmitoyl PC. Other lipids present are phosphatidylglycerol (PG), phosphatidylinositol (PI), phosphatidylethanolamine (PE).

Plant hormones, such as but not limited to, ethylene, abscisic acid (ABA), and gibberelic acid (GA3), a gibberelin, zeatin a (cytokine), auxins (indole-3 acetic acid, IAA) involved in chemiosmotic proton gradients, Zeatin (a cytokine) may be offered in the subject compositions for the prevention or reduction of premature births. The plant hormones may be added to highly hydrophilic surfactants in the modulation of mitosis adding to the management of cancer, and may be incorporated in therapeutic stem cell-like subject compositions, all with a high degree of bio-safety. This is also emphasized relating to other embodiments concerning modulation of mitosis.

Variants of Tween 80, a highly ethoxylated high HLB hydrophilic surfactant with 20 moles of ethylene oxide, can be ethoxylated further with 20-40 or more moles of ethylene oxide to increase the HLB. Obversely Myrj represents a low HLB surfactant with 8 moles of ethylene oxide moles to 1 mole of fatty acid such as stearic acid. Two carbon ethylene, (and multiplicity of ethylene oxide derived surfactants), function as a maturation factor, and may be combined with hydrophilic surfactant activity in these ethoxylated surfactants.

The compositions can be employed for local and systemic therapies and can be delivered by topical, oral, parenteral or intravenous routes. In the case of cancer, intralesional or even intra-arterially administration may be practiced. A more preferred route is oral administration, preferably by oral mucosal delivery in which the compositions are formulated into a lozenge or gum that is brought into contact with the oral buccal sublingual, or pharyngeal mucosal surface for a few to twenty minutes (or longer) until absorbed. The high HLB mediated oral mucosal delivery system is as efficacious as parenteral administration of such medications and prophylactic agents as vaccines (further documented by laboratory measured response in other embodiments). When an oral route of administration is used, the component concentrations can be lower than in intravenous routes, since the components do not pass through the liver. This oral mucosal delivery system can also be advantageously used with enzymes or hormones administration. The therapeutic compositions are preferably administered at a temperature slightly less than 100 degrees F., more preferably at or about 98.6 degrees F., to further enhance the synergism of, surfactant and enzymatic activity.

The compositions offer protective effect including but not limited to the chelating protective effect of the macromolecules such as, but not limited to, DNA and their protection from toxic chemicals such as heavy metals as well as antioxidant protection from radiation. The exemplary antioxidants for optional addition to the subject compositions include, but are not limited to vitamin A in the form of beta-carotene, 10,000 units per day; D-alpha tocopherol 400 units ideally chelated 200 micrograms of selenium to the methionine per day; and/or ascorbic acid preferably in capsule form 500 milligrams to 8 g (particularly when uric acid levels are elevated and functioning as a natural antioxidant), in divided dosages. The effects of the compositions can be long-lasting, with benefits extending for six months or more after therapy is discontinued.

The pharmacodynamic basis for successful unexpected therapeutic results with the compositions of the invention include (a) hydrogen bonding, (b) anionic charge, (c) electrostatic polar forces, (d) van der Waal forces, and (e) zeta potential associated with the non-covalent interactions with the macromolecules.

In addition to having anti-inflammatory and tissue healing activities, the compositions provide a biochemical environment in accord with the law of mass action that can activate inactive genomic components and increase expression of one-third or more of the genome thereby potentially countering disease including hereditary conditions. This can counter a genetic imbalance and can therefore overwhelm disease-producing genes, even those produced by hereditary changes.

In addition the pharmacodynamic basis for the effects of genetic therapy non-chiral function in a self-perpetuating mode through the L tetrahedral 3D fit of L-amino acids and glycine non-covalent biochemical macromolecular binding to D polysaccharides such as but not limited to the genetic system macromolecules DNA, RNA, ribosomal RNA and ribosomes and their respective polymerases furthered by the law of mass action mediated by progressive therapy with synthetic therapeutic stem cell-like subject composition of L-amino acid and glycine. Thereby, in addition, these pharmacodynamic effects of genetic therapy function in a self-perpetuating mode through the biochemical law of mass action mediated by progressive therapy with synthetic therapeutic tissue and stem cell-like subject composition of L-amino acid and glycine, polar surface-active lipids and optional inclusion of extracellular matrix scaffold.

L-tetrahedral fit; Surfaces and Tetrahedral fit of each alpha amino acid. Surface magnification of molar ratio (protein) and reactive moieties and tetrahedral fit in protein synthesis and as therapeutic anti-inflammatory healing therapy, The C2 through C6 twenty L amino acids and non chiral glycine including the 8 C3 propionic acid derivatives are analog to such C3 propionic acid derivative, and $C_4$ butyric acid derivative, anti-inflammatory medications and their reactive moieties. In contrast the routine anti-inflammatories listed in the PDR are benzene ring containing compounds from which many medications and anti-inflammatory drugs are derived, lacking the L alpha amino acid and glycine 3D tetrahedron fit in protein synthesis, actually interfere with protein synthesis, (a non-tetrahedral 3D planar gliding action is present in anti-inflammatory medication).

The compositions can also be employed for metabolic diseases and conditions such as Type 1 with insulin deficiency wherein the molar ratio of the protein insulin may be incorporated into subject composition to stimulate the production of insulin as well as replacing suspected trace element deficiency such as but not limited to chromium or type 1 diabetes and the diabetic state where there is adequate insulin but with inadequate insulin receptor response which may be modified with high HLB therapy.

The therapeutic compositions may also be specifically applied to addiction by mimicking normal tissue metabolism and normal tissue including the L-amino acid glycine molar ratio of endorphin to metabolically stimulate and in fact coerce the body to produce this hormone. These same principles and therapeutic components have been applied in normalizing, as noted in a prior embodiment's dependency or withdrawal symptoms such as, but not limited to, the use of drugs in controlled substances, alcohol and/or drug and tobacco addiction in the medical patient or veterinary practice or experimental conditions such as the animal or tissue culture. Therefore these compositions form a clinical bridge beyond other advanced technologies that have not to date found a clinical application. Examples of suitable therapeutic uses include the treatment of Crohn's Disease, and in particular Pediatric Crohn's Disease (PCD), a chronic, relapsing, unremitting disease with grave, guarded prognosis for which conventional treatment includes high-risk immune suppressants such as corticosteroids at high doses. In many cases, particularly in pediatric cases, major surgical intervention is required within five (5) years of initiation of observation, with resection of up to several hundred grams of diseased organ tissue. Surgical intervention effectively arrests disease complications but has no effect on the clinical course of the disease. In fact, many patients require repeated surgical intervention. The use of these therapeutic stem cell-like subject compositions reduces or eliminates long-term corticosteroid use in these patients along with reducing side effects including but not limited to the interference and prevention of healing (so important in the management of Crohn's disease or Pediatric Crohn's disease) in these patients.

When these tissue normalizing principles and therapeutic subject compositions have been used in allergic asthmatic disease, therapeutic benefits have included: minimizing emergency use of corticosteroids, or possibly excluding the need for bronchodilator medication effect of sympathomimetic medication such as the beta sympathomimetic agonists. Further minimizing emergency use of sympathomimetic medications and their vicious cycle, of rhinitis medicamodosa or asthmatic bronchitis or potential bronchopulmonary equivalent asthmatic medicamentosa side effects seen with the past inhalation overuse of isoproterenol as the locked lung syndrome).

Additionally, transplantation or other surgery can be averted in congenital biliary atresia (CBA), a disease that is usually fatal if left untreated surgically. Even though CBA has an incidence of 300 cases occur annually in the U.S. this disease represents the most common rational for liver transplantation in the pediatric age group.

The co-use of subject composition with the many medications available and prescribed from the PDR extend synergistic pharmacodynamics of these subject compositions and may be integrated with the successful bio-efficacy of the therapeutic effects of the compositions, exemplified by:

(1) reinstitution of organ and tissue function regardless of organ and tissue involved and regardless of etiology, such as but not limited to trauma;

(2) diseases of inherited predisposition such as, but not limited to, lysosomal storage diseases and deficiency diseases such as but not limited to enzymatic deficiency including for example, lysosomal storage disease in addition to specific enzyme deficiency replacement, residual tissue and organ dysfunction due to encroachment of distended lysosomes may be further treated with these subject compositions. This includes HLB modulation with the added advantage of the polar surface active lipid surfactant high HLB packing parameter to synergize, facilitate and accelerate small amounts of enzyme that may be present. This is accomplished by increasing surface area, not only of the deficient enzyme, but also of its substrate to maximize the enzyme's metabolic activity. By these methods, the genetic profile and pattern predisposing to disease in treatment will be minimized and normal genetic function become more dominant. Include as exemplified here but not limited to even the recessive lysosomal storage diseases.

Diseases and the syndrome of diseases may be viewed here as being analog to an insoluble crystalline 'thorn in the side' of the patient's tissue and metabolic processes whether diseases such as obesity with insoluble fat particles, atherosclerosis with cholesterol crystals, cancer, genetic diseases lacking enzymes to fluidize and hydrophilize these lysosomal deposits, or other insoluble crystal like structures such as asbestos or silicosis. The liquid crystals provided in this discovery characteristic of the polar surface active lipids thereby reverses these disease mechanisms structures and functions whether by the highly hydrophilic polar surface active lipid surfactant and/or by the initial addition in Component No. 2 to disperse the fat with highly lipophilic polar surface active lipid surfactant.

The added advantage offered by these surfactants is that by making these crystalline or crystalline like non-soluble metabolites randomly dispersed thereby changing entropy, energy is also provided at the same time equivalent to energy of metabolizing fat such as palmitic acid (or the combustion of paper) with the release of energy to complete the metabolism of these disease causing crystalline structures.

Current medication in the public domain emphasizes the use of (as exemplified in cancer) of platinum and cis-platinum and other allied anti-cancer therapeutic agents. These agents were originally noted to be lethal to infectious microorganisms and this concept was further translated to the therapy of cancer.

Singular and novel to the prior art is therapy for infectious disease or for cancer that is not dependent on its lethality to tissue and its associated disease but is dependent upon the principle that human tissue can be facilitated and synergized to assume the function and structure of replicating itself, thereby replacing the vicious cycle of disease. This averts major side effects difficult to accept that are associated with therapeutic lethality concept, thereby normalizing human tissue using compositions that mimic and are analog to human tissue not only in structure but also in function.

Such compositions can be used to treat neoplasms as in cancer or infectious diseases, in overcoming antibiotic sensitivity, or inactivation without damaging or killing human tissue. In the case of infectious disease, the same high HLB polar surface active lipid surfactant composition as in the anti-cancer therapeutic components as in No. 2 (which may be used alone or in concert with synthetic stem cell containing and components Nos. 1, 2, and 3) are used to counter such microorganism invasive modalities as lipid A, LPS (lipo-polysaccharide as in toxic shock syndrome) that were formerly antibiotic resistant. A similar dual mechanism as with platinum, however without major side effect concerns.

In inflammation and degenerative diseases without giving up imperative protein synthesis in healing associated with the existing anti-inflammatory drugs, synthetic therapeutic stem cell containing components Nos. 1, 2, and 3 can be used.

Congenital and genetic diseases can be treated using a composition of a "synthetic stem cell" containing therapeutic component Nos. 1, 2, and 3 without assuming life threatening entree through the portal vein and infectious microorganism carrier agents. For example, oral mucosal administration can be used, (thereby bypassing portal vein delivery) in these so targeted applications.

Trauma management can be performed with the local and systemic use of a synthetic stem cell composition containing component Nos. 1, 2 and 3, while greatly minimizing additional trauma and salvaging tissue by minimizing the requirement of debridement. This provides a sutureless wound closure using progressive approximations with steri strips and inactivation of collagenase which has been activated by cortico-steroids, (which has become more commonly used in the management of chronic diseases).

These foregoing treatments combined as one therapeutic unit but administered as a single dosage or two to 4 times daily divided dosages may be given locally, systemically including intravenous administration and oral mucosal delivery system companion to this series of inventions.

SUMMARY OF THE INVENTION

Compositions of the subject invention can comprise three, four, or five of the following components:

Component No. 1: 10 to 25 grams of molar ratio amino acids such as but not limited to Neocate (SHS, Liverpool, U.K.).

Furthered by the law of mass action coercing the protein assemblage system three to four times a day, L amino acids and glycine non-covalently bond and fit with the dextrorotatory pentose macromolecules of the protein assemblage system's template DNA and RNA those messenger and transfer RNA and ribosomal macromolecules.

Component No. 2: Polar surface active lipid, Phosphatidylcholine (PC) 0.9 g administered one to three times daily, (American Lecithin, Oxford, Conn.) or available in component No. 1 in L Neocate; Phosphatidylserine (PS) 100 mg contained in a 500 mg complex capsule administered 1 to 3 times daily, (Serinaid, Springfield, Utah); anti-inflammatory Omega 3 fatty acids, 1000 mg per 2 capsules, 2 capsules two to three times daily; 100 mg D-alpha tocopherol antioxidant, antirancidity fish oil complex, with active ingredients 180 mg EPA, 125 mg DHA and/or seed oil flaxseed oil (250 mg, organically grown replacing 100 mg of DHA). High HLB polar surface active lipid surfactants such as Tween 80 may be used alone or with Component Nos. 1, 2, and 3 for: (a) modulation of mitosis (>normal), as a normal progression; or (b) normalizing mitosis of cancer.

In cancer with the therapeutic use of highly hydrophilic surfactant such as Tween 80 with its hexagonal geometric format microscopically analog to normal mitosis, as shown in other embodiments may now be used to fluidize and normalize to the normal metaphase and anaphase stages of mitosis to progress to 2 normal daughter cells instead of being arrested or 'stuck', in an analog fashion as an old phonographic record might be stuck at the mitosis organization center MOTC at which site and transitional time a crystallization like seeding in the growth of crystals effect occurs with regard to the tread milling polymerization of tubulin and microtubulin with new tubulin molecules added at the growing advancing end of the microtubules whereas others are lost in depolymerization at the opposite microtubulin end (at anaphase depolymerization at this end of the microtubules occurs) until the analog player needle is advanced or normalized as in the case of cancer with high HLB surfactants. This high HLB anticancer activity has been shown in foregoing and in prior embodiments.

This normal function of normal progression of mitosis may be further envisioned as clasped hands which progressively separate at metaphase and the fingers of the clasped hands completely separate and endow each daughter cell with the equal quantitative and qualitative complement of DNA to continue their genetic activity. A maturation factor is also contained in the same Tween 80 molecule in the form of ethylene oxide (20 moles), resulting in normal progression resulting in apoptosis followed by new cellular regeneration. The hydrophilicity is further increased not only by the 20 oxygen atoms as $OH_2$ in the 20 moles of ethylene oxide and six atoms of oxygen in the one mole of sorbitol but also by the central double-bond of one mole of oleic acid interrupting the 17 consecutive $CH_2$ found in the more hydrophobic stearic acid as an analog "elbow" joint (c) Reduction in abnormal mitosis and cancer cells, approximately 50% histopathologically, after Tween 80, 0.125% of exposure after 24-48 hours, as well as 76 to 83%% cancer cell inactivation in vitro breast cancer tissue culture monitored by inactivation of cancer cell mitochondria, (d) progression of cellular maturation resulting in apoptosis with ethylene oxide, a maturation and ripening factor for fruit in agriculture (an analog structural function in cell physiology not taught in the prior art), a monomer of Tween 80 which contains 20 moles of ethylene oxide.

All of the surfactants may be used as the equivalent weight volume dosage as the 0.125 percent dosage in these embodiments; or may be used with a therapeutic dosage of 10 to 20 to 50% of the LD 50. For example Tween 80 (with a dosage of 20 to 50% of the LD 50) LD 50 in the experimental animals (rats and mice) is 7.5 ml per kilogram (identical to highly lipophilic surfactant PGPR) with a Tween 80 or PGPR dosage of 10 to 50% of the LD 50. In a 70 kilogram patient the starting total daily dosage would be 50 to 100 ml, further divided into three to four dosages daily. It must be noted that the LD 50 is based upon studies in normal animals with normal hydrophilic/lipophilic equilibrium balance HLB. This specialized use is for patients with abnormal HLB requiring significant hydrophilic surfactant dosage. Therefore this latitude expanding the dosage in these patients is therapeutic in contrast to the LD 50 studies of normal HLB animals that did not require HLB modulation. The LD 50 for sodium lauryl sulfate is 1288 mg per kilogram in the experimental animal, (rats orally) with or 900 to 1800 mg, further divided into three to four dosages daily Tween 80. Low HLB polar surface active lipid lipophilic surfactant PGPR polyglycerol polyricinolate 0.3% mother range of 0.01 to 0.05% to 10% may be used in any of these applications as a thrust mechanism to disperse and mobilize the hydrophobic tissue components at 4 to 12 hours before use of foregoing high HLB surfactant.

Antioxidants such as D-alpha tocopherol 400 units, ascorbic acid 500-1000 milligrams spansule, beta-carotene 10,000 units, along with the L amino acids and glycine of this therapeutic composition giving non-covalent DNA macromolecular protection also helpful in this anti-cancer therapeutic application of subject composition.

Component No. 3: The extracellular matrix can be given in the form of 740 mg capsules, 4 to 6 capsules 3 times daily. The capsules comprise a proteoglycan aggregate complex of cartilage, chondroitin sulfate covalently bonded to core proteins, further non-covalently linked to macro molecule of hyaluronic acid and collagen (see for example, Cartilade, BioTherapies, Inc., Fairfield, N.J.). Component No. 3 is therapeutically used along with component No. 2 self-vesiculating phosphatidylcholine with HLB of 10 to 11 and will further protect the cell and tissue.

This therapeutic formulation will further protect from radiation damage as in radiation therapy of cancer and/or radiation in regard to bio-terrorism attacks and nuclear plant accidents and in this protective function joins component No. 1 in radioprotection. Observations regarding amino acid amino groups and SH groups of cysteine should not exceed 1 g per day, however in the case of cancer, larger dosages to be considered such as 1 to 2 grams daily, indicate that the SH group is further protected by other phosphate groups as in phosphatidylcholine of component No. 2, or by the addition of adenosine diphosphate with the effect of promoting differentiation so important in countering the most aggressive anaplastic aspects of cancer. CSF cytostatic factor may also be added synergistically to compositions for this anti-cancer therapy. This may be derived from the cytoplasmic sap of the unfertilized egg and has similar differentiation promotion factors that are anti-cancer. This unfertilized egg CSF cytostatic, cytoplasmic factor may be sourced and derived from any unfertilized ovum including fish eggs, including sourcing as low allergenic risk potential frogs and/or ostrich eggs since derived from a source where exposure and sensitization has not (or only rarely) occurred (see Example 13).

The compositions offer protective effects including but not limited to the chelating protective effect for macromolecules including but not limited to DNA and their protection from toxic chemicals such as heavy metals as well as antioxidant protection from radiation. The optional addition of antioxidants, such as but not limited to vitamin A (in the form of beta-carotene 10,000 units per day) D-alpha tocopherol, 400 units, ideally chelated to 200 micrograms of selenium to the methionine, per day, ascorbic acid preferably in capsule form 500 milligrams to 8 g in divided dosages is also contemplated by the subject invention.

The inter-biochemical radio-protection of these components of synthetic stem cell therapeutic composition is analog to the protection of aminophostine without the very sickening side effects of nausea and vomiting of aminophostine which may be further minimized (as the case in optional co-use with any therapy with major side effects) by this synthetic stem cell therapeutic subject composition when these three components and specific dosages of subject composition are used.

Further to the use of the extra cellular matrix component No. 3 for the management of cancer the addition of ECM component No. 3 helps to (1) complete the copy of human tissue; (2) it also adds 50% additional healing capacity to a wound or disease; and (3) it is of great value in correcting the healing deficiency of many patients requiring corticosteroid therapy.

An anabolic medicament is also provided which is involved in tissue healing and tissue regenerative which along with mimicking the molar ratio of the 20 free non D-amino acids specified in the genetic code of human tissue protein. The composition also mimics all the other essential components of human tissue including the polar surface active lipid phospholipids, such as phosphatidylcholine, omega-3 fatty acid essential fats, as well as the extracellular matrix composition comprising: (1) fibrous structural proteins such as collagen and elastin, (2) adhesive glycoproteins such as laminin and fibronectin, and (3) proteoglycans and hyaluronan consisting of a core protein and polymers of aminated disaccharides which are also sulfated polysaccharides and glycosylated proteins (glycoproteins).

The sulfated polysaccharides include, but not limited to chondroitin sulfate and proteoglycan complexes of cartilage wherein chondroitin sulfate are covalently linked to extended core protein molecules which in turn are non-covalently linked to a huge hyaluronic acid polysaccharide glycosaminoglycans polymer molecules with the aid of link proteins. The subject compositions also provide a therapeutic correction of the major complicating multiple metabolic component deficiencies to synergistically continue the therapeutic correction of diseases such as Crohn's disease and pediatric Crohn's disease and specific in the management of regional ileitis characterizing Crohn's disease in that the ileum is normally the sole site of vitamin B12 absorption and uniquely here whose vitamin B12 levels are less than ten percent of normal: of statistical significance joining a less than ten percent of normal vitamin A level (retinol) correction of which locally and systemically corrects healing deficiency in this disease associated with long-term steroids along with a less than ten percent vitamin D level, vitamin D, E (D-alpha tocopherol) and prothrombin time in contrast to less than 20% of normal levels of red cell folate, copper, less than 30% zinc, serum folate, plasma ascorbate, less than 50% plasma selenium and hemoglobin other trace elements and minerals and vitamins and enzyme study such as less than 90% serum and plasma glutathione peroxidase, ferritin of a total of 15 studied components) due to the ravages of disease (such as but not limited to progressive severe gastrointestinal disease such as the chronic granulomatous inflammatory disease such as Crohn's disease which specifically in its pathogenesis targets the ileum and its associated negative nitrogen balance (primary to the disease per se and secondary to malabsorption and enzymatic deficiency and chronic recurrent severe diarrhea)) and even further complications which include therapeutic side effects such as but not limited to the side effects of corticosteroids which include growth retardation and interference with pubertal development.

Inclusive in this response of 450 patients collated as a multi-center study is in response to foregoing therapy and is further inclusive of a response to vitamin, mineral, and trace element replacement therapy. It may be looked upon therapeutically as mimicking these normal components and quantitative levels of vitamins and minerals and trace elements of human tissue.

Each disease group will be studied for deficiencies which will be corrected as exemplified by components No. 4 and No. 5 to complete the mimicking and analog structure of normal tissue in the normal replication of human tissue, normalizing its structure and function in order to bring about the arrest of the vicious cycle of diseases and their pathogenic mechanisms.

Component No. 4: The 4th component in helping to complete and attain mimicking and analog to normal human tissue comprises vitamins, minerals, and trace elements. Utilizing documented deficiencies of vitamins, minerals and trace elements from available studies or performing pilot study guide lines. Exemplary deficiencies in Crohn's disease are documented in the examples presented. Vitamins, minerals and trace elements can be provided in various concentrations. For example, vitamin B12 (100 micrograms), vitamin A (as beta-carotene 10,000 units), vitamin D, vitamin E, D-alpha tocopherol, Selenium 200 micrograms chelated with methionine as sodium selenomethionine (or to sulfur containing cysteine).

Component No. 5 comprises Phytozyme, (Life Plus Int'l, Batesville Ark.), Amylase 50 mg., Bile 45 mg., Bromelain 30 mg., Lipase 25 mg., Pancreatin 6× (NF.) 100 mg., Pancrelipase 110 mg., Papain 30 mg., Pepsin 70 mg., Betaine HCl 100 mg., and Probiolic Blend 20 mg tablet.

Ingredients: Betaine, HCl, Pancrelipase, Pancreatin 6× (N.F.), Pepsin, Dicalcium Phosphate, Amylase, Bile, Bromelain, Papain, Lipase, L-Glutamic Acid, (ProBio Tx), Stabilized Probiotic Blend (Each dosage: 200,000,000 probiotic micro-flora including *Lactobacillus acidophilus* DDS-1, *Bifido-bacterium bifidum, Lactobacillus bulgaricus, Lactobacillus salivarius*), vegetable and fruit concentrates. Deficiencies of pancreatic enzymes are readily available in exampled disease, Crohn's disease, along with cystic fibrosis. Therefore, corrected here in the therapeutic component formulations to normalize not only human tissue but its secretions. Reversal to normal flora with pro-biotic also readily available and, therefore, used here for the same therapeutic rationale of normalization of tissue, its symbiotic surface bacteria and associated secretion contents of enzymes.

This detailed therapeutic replication of normal human tissue secretions, deficient in such diseases as Crohn's disease and cystic fibrosis, (and therefore synergizes further complete reversal of disease tissue). By including therapeutic component Nos. 4 and 5 and secretions of the tissue and the normalization of the micro-organism flora with associated normalization of function of this gastrointestinal Crohn's diseased tissue has made possible for this patient for the first time to further reduce from one tablet of the corticosteroid that this three component therapy has permitted to use ½ tablet instead (Triamcinalone, generic) for the first time in three decades. The side effects this patient has sustained from long-term corticosteroids has been worsening of osteoporosis documented by two successive bone scans two years apart, recurrent bruising and failure to heal including two threats of the need for skin graft which this subject composition stem cell-like treatment has prevented.

In the case of the gastrointestinal tract in diseases such as, but not limited to, Crohn's disease, the addition of enzymatic therapy of component No. 5 and the addition of pancreatic and enzymatic replacement of deficiencies present herein normalizes the gastrointestinal secretion component and byproduct of human tissue. The addition of pro-biotic microorganism therapy such as, but not limited to, *Saccharomyces boulardii* helps normalize the abnormal microflora that the disease gastrointestinal tract such as but not limited to Crohn's disease predisposes to thereby even further normalizing abnormal microflora (which this vicious cycle chronic granulomatous Crohn's disease has fostered) the gastrointestinal microflora, tissues and secretions.

An extension of treatment of the synthetic stem cell therapy subject composition in the same patient as Ex. 1 with the addition of component No. 4 presented in detail in Ser. No. 09/639,859 and therapeutic component No. 5 enzyme and pro-biotic 0.9 g tablets two tablets daily to three times a day preferably before meals of enzyme replacement and pro-biotic microflora normalizing factor. These favorable conditions make it more and more difficult for the diseased tissue, such as but not limited to chronic granulomatous disease, as in Crohn's disease and thereby reversing the vicious cycle of this disease and other diseases such as but not limited to Crohn's disease. This has proved itself clinically in the embodiment example cited here wherein digestive enzyme formulation containing pancreatic enzyme replacement, (as well as bile which has also been incriminated as deficient in Crohn's disease) along with pro-biotic micro-organism resulted in flora normalization. The probiotic in this case was *Lactobacillus acidophilus, Bifidobacterium bifidum, Lactobacillus bulgaricus, Lactobacillus salivarius* use of in this addition and completion of the normalization therapeutic stem cell-like repair kit formulation.

Most importantly component steps are analogous to a team or corporate approach to the anabolic reconstructive reversal of the pathogenesis of a complex vicious cycled catabolic destructive disease further analog to the underlying pathogenetic mechanisms and the basis of the former refractory state of disease. Crohn's disease and many other diseases with such analogous pathogenetic destructive componential mechanisms, associated deficiencies and medication side effects can be treated with the subject composition. Preferably to best address this disease state, all components of synthetic stem cell like subject composition formulations are contained in the molar ratios of human tissue.

The human tissue normal molar ratios of these foregoing components include such as, but not limited to, non D-amino acids of the 20 amino acids specified in the human genetic code, polar surface active lipids such as, but not limited to, cell membrane components, extracellular matrix components, vitamins, minerals, trace elements are herein defined as being at least 90% of the composition by weight and 10% by weight or less of composition that is not in conformance with the molar ratios by weight of human tissue. Preferably the human tissue molar ratio of composition of these components are at least 95 percent by weight and five percent by weight or less not strictly corresponding to the molar ratio of human tissue, and most preferably the human tissue molar ratio component composition corresponding to over 99% by weight and 1% or less not strictly corresponding to the molar ratio of human tissue.

The prior embodiments documented such as but not limited to the reversal of the need for skin graft in wound treatment of a Crohn's patient (exemplified by adding deficient vitamin A locally to anabolic counter collagenase stimulated by long-term corticosteroids along with wound healing anabolic zinc in the form of zinc oxide in the local and systemic anabolic therapy using locally and systemically subject to position synthetic stem cell-like medicament. Resulting in mechanisms also associated with the successful reduction in the need for long-term corticosteroid observer, in 85 percent of the 450 patients studied (multicenter studies).

The subject composition also provided for a marked reduction in the necessity for major abdominal surgery (excisional bowel surgery and correction of fistulization is required in 70 percent of pediatric Crohn's disease patients in a period of conventional therapy five year care (data provided by the Ileitis Foundation of America) as exemplified by a 60 percent reduction in the need for correction of fistula by surgical care. In the 40 percent remaining that require major abdominal bowel surgery this therapy offers a further 55 percent reduction in surgical mortality.

Pediatric Crohn's disease is a disease of hereditary predisposition. However, if this specific anti-inflammatory treatment is discontinued after one month of therapy (as might occur in the management of children considering stomach tube administration in the past), the absence of recurrence is noted to be as long as six months in those that discontinued treatment (70 percent fortunately do not recur in 7 to 12 months of further observation after discontinued treatment). This is suggestive of a genetic therapeutic component associated with this treatment.

The therapeutic application of the subject compositions also provide anti-inflammatory therapeutic responses without the usual associated complication of impairment of tissue protein synthesis and thereby further aggravation of negative nitrogen balance.

Documented studies here showed that further correction of these deficiencies added to any therapeutic plan added significantly to the prevention of this disease's significant predisposition for recurrences. Also included were enzymatic therapy and essential omega-3 EPA fatty acid fats with their contribution to this anti-inflammatory therapy as well as the addition of extracellular matrix (ECM), and reversal of impaired healing (associated with pediatric Crohn's disease and long-term steroids).

The addition of these deficiency corrections would further add to the management of this formerly intractable vicious progressive chronic granulomatous disease, pediatric Crohn's disease in the growing child. Potentially contributing to the 15% of patients (vs. the 85%) that were not able to replace corticosteroids.

The components of the subject invention can, in some embodiment, be combined to form compositions. For Example, components No. 1 and No. 3 can be useful for anti-inflammatory or healing. Component No. 1 can be used to aid in protein formation and component No. 2 can be used to replace damaged cell membranes. Component No. 3 increases tensile strength of wound by 48% in more than 100 patients multi-center and double-blind, as well as in controlled animal studies and component No. 2, modified PC lysolecithin triggers onset of protein synthesis working synergistically with component No. 1.

Liquid crystal high HLB surfactants HLB>13 specifically 15-16 to 20 with a high packing parameter of less than ½ and contributing a high repulsive of charge zeta potential along with an increase in surface area and thereby synergize enzymatic activity of enzyme in association with a substrate, (thereby synergizing component No. 5) and as an anti-cancer agent also down modulating mitosis (in vitro documentation in prior embodiments) and especially in the use of Tween 80 containing 20 moles (or more) of ethylene oxide a maturation factor highly useful in the stimulation of apoptosis, a highly useful anti-cancer feature. The anti-cancer therapeutic features may be used alone or in conjunction with components 1, 2 and 3 as well as components one, two, three, four and five.

These subject compositions may be administered orally or parenterally or locally and in special applications as in anti-cancer may even be administered intra-arterially as therapy used in conjunction with routine medications to reduce side effects and synergize these companion medications and thereby lessen the dose required of routine medications.

In simulating all stem cell biochemical biophysical features simulated results as evidenced by averting need for an organ transplant while avoiding key stem cell side effects:

(1) Bioethics independent of use of human embryonic tissue, but can build and rebuild thereby enhancing tissue healing, protein synthesis on existing tissue and in vitro recombinant DNA tissue culture, (2) Avoiding the risk of transmission of such diseases as AIDS and Hepatitis and even cancer cells (incipient), (3) Avoiding the risk of rejection reaction and the need for HLA cross matching, (4) Adding a significant anti-tumor anti-cancer effect, (5) Sourcing has avoided the risk of allergic reaction by avoiding protein or substances that would cross match the patient's genetic code, (6) May be used freely with other medication to reduce their significant risk and dosage of medication.

In certain embodiments of the subject invention, a composition comprising: a) at least one glycosaminoglycan, proteoglycan aggregate complex of hyaluronic acid, extracellular matrix protein and chondroitin, extracellular matrix compound in an amount effective in the damaged tissue as an anti-neo-inflammatory and anti-neo-angiogenetic agent; b) about one to three grams of at least one polar surface active lipid selected from the group consisting of phosphatidic acid, phosphatidylethanolamine, lecithin, phosphatidylserine, phosphatidylinositol, 2-lysolecithin, plasmalogen, choline plasmalogen, phosphatidylglycerol, diphosphatidylglycerol, sphingomyelin, and any combination of 2, 3, 4, 5, 6, 7, 8, 9, 10 or of said polar surface active lipids; c) a plurality of enantiomerically pure D-amino acids and glycine of about 9 to 25 grams; d) a component selected from the group consisting of polyoxyethylene Sorbitan Monooleate (TWEEN 80), Sorbitan monooleate, grape seed extract, grape extract, and combinations thereof; and e) vitamins, minerals or trace elements selected from the group consisting of Vitamin B12, Vitamin E, selenium, zinc, and combinations thereof is provided. Compositions of the subject invention can further comprise a compound generally accepted as safe (GRAS) selected from the group consisting of aspartame perfluorocarbon resins, perfluorocarbon cured elastomers. [alpha]-Amylase enzyme preparation from *Bacillus stearothermophilus*, benzoic acid, bromelain, catalase (bovine liver), lactic acid, linoleic acid, potassium acid tartrate, propionic acid, stearic acid, tartaric acid, diacetyl tartaric acid esters of mono- and diglycerides, ammonium bicarbonate, ammonium carbonate, ammonium chloride, ammonium hydroxide, ammonium citrate, dibasic, ammonium phosphate, monobasic; ammonium phosphate, dibasic; bacterially-derived carbohydrase enzyme preparation; bacterially-derived protease enzyme preparation; bentonite; benzoyl peroxide; n-Butane and iso-butane; Calcium glycerophosphate; Calcium lactate; Calcium pantothenate; Calcium propionate; Calcium stearate; Carbon dioxide; Beta-carotene; Cellulase enzyme preparation derived from *Trichoderma longibrachiatum*; Clove and its derivatives; Cocoa butter substitute; Copper gluconate; Copper sulfate; L-Cysteine; L-Cysteine monohydrochloride; Dextrin; Diacetyl; Enzyme-modified fats; Ethyl alcohol; Ficin; Glucono delta-lactone; Corn gluten; Wheat gluten; Glyceryl monooleate; Glyceryl behenate; Glyceryl palmitostearate; Helium; Inositol; Insoluble glucose isomerase enzyme preparations; Isopropyl citrate; Animal lipase; Magnesium carbonate; Magnesium chloride; Magnesium hydroxide; Magnesium oxide; Magnesium phosphate; Magnesium stearate; Magnesium sulfate; Malt; Malt syrup (malt extract); Manganese chloride; Manganese citrate; Manganese gluconate; Manganese sulfate; Microparticulated protein product; Mono- and diglycerides; Monosodium phosphate derivatives of mono- and diglycerides; Niacin; Niacinamide; Nickel; Nitrogen; Nitrous oxide; Peptones; Pancreatin; Papain; Pectins; Pepsin; Potassium bicarbonate; Potassium carbonate; Potassium chloride; Potassium hydroxide; Potassium lactate; Propane; Pyridoxine hydrochloride; Rennet (animal-derived) and chymosin preparation (fermentation-derived); Riboflavin; Riboflavin-5'-phosphate (sodium); Sodium benzoate; Sodium carbonate; Sodium hydroxide; Sodium hypophosphite; Sodium lactate; Sodium metasilicate; Sodium propionate; Sodium sesquicarbonate; Sodium tartrate; Sodium potassium tartrate; Starter distillate; Stearyl citrate; Thiamine hydrochloride; Thiamine mononitrate; [alpha]-Tocopherols; Triacetin; Tributyrin; Triethyl citrate; Trypsin; Urease enzyme preparation from *Lactobacillus fermentum*; Vitamin A; Vitamin B12; Candelilla wax; Carnauba wax; Bakers yeast extract; Zein; Sulfamic acid; Clay (kaolin); Ferric oxide; Iron oxides; Japan wax; Tall oil; Alfalfa; Allspice; Almond, bitter (free from prussic acid); Ambrette; *Angelica* root; *Angelica* seed or stem; Angostura; Anise; Asafetida; Balm; Balsam of Peru; Basil; Bay leaves; Bay; Bergamot (bergamot orange); Bois de rose; Cacao; Camomile (chamomile); *Capsicum*; Caraway; Cardamom seed (cardamon); Carob bean; Carrot; Cascarilla bark; *Cassia* bark, Chinese; *Cassia* bark, Padang or Batavia; *Cassia* bark, Saigon; Celery seed; Cherry, wild, bark; Chervil; Chicory; Cinnamon bark, Ceylon; Cinnamon bark, Chinese; Cinnamon bark, Saigon; Cinnamon leaf, Ceylon; Cinnamon leaf, Chinese; Cinnamon leaf, Saigon; Citronella; Citrus peels; Clary (clary sage); Clove bud; Clove leaf; Clove stem; Clover; Cocoa; Coffee; Cola nut; Coriander; Corn silk; Cumin (cummin); Curacao orange peel; Cusparia bark; Dandelion; Dandelion root; Dill; Dog grass (quackgrass, *triticum*); Elder flowers; Estragole; Estragon (tarragon); Fennel, sweet; Fenugreek; Galanga (galangal); Garlic; Geranium; Geranium, East IndianGeranium, rose; Ginger; *Glycyrrhiza*; Glycyrrhizin, ammoniated; Grapefruit; Guava; Hickory bark; Horehound (hoarhound); Hops; Horsemint; Hyssop; Immortelle; Jasmine; Juniper (berries); Kola nut; Laurel berries; Laurel leaves; Lavender; Lavender, spike; Lavandin; Lemon; Lemon balm (see balm);

Lemon grass; Lemon peel; Licorice; Lime; Linden flowers; Locust beanLupulin; Mace; Malt (extract); Mandarin; Marjoram, sweet; Mate 1; Menthol; Menthyl acetate; Molasses (extract); Mustard; Neroli, bigarade; Nutmeg; Onion; Orange, bitter, flowers; Orange, bitter, peel; Orange leaf; Orange, sweet; Orange, sweet, flowers; Orange, sweet, peel; *Origanum*; Palmarosa; Paprika; Parsley; Pepper, black; Pepper, white; Peppermint Peruvian balsam; Petitgrain; Petitgrain lemon; Petitgrain mandarin or tangerine; Pimenta; Pimenta leaf; Pipsissewa leaves; Pomegranate; Prickly ash bark; Rose absolute; Rosa; Rose; Rose buds; Rose flowers; Rose fruit (hips); Rose geranium; Rose leaves; Rosemary; Rue; Saffron; Sage; St. John's bread; Savory, summer; Savory, winter; *Schinus molle*; Sloe berries; Spearmint; Spike lavender; Tamarind; Tangerine; Tannic acid; Tarragon; Tea; Thyme; *Triticum*; Tuberose; Turmeric; Vanilla; Violet flowers; Violet leaves; Violet leaves absolute; Wild cherry bark; Ylang-ylang; and; Zedoary bark, or any combination of said compounds. Any combinations of the compounds GRAS can be used in formulating compositions of the subject invention. In some embodiments, the composition further comprises a flavorant that can be a fruit juice, such as tomato juice.

The following sections of Title 21 of the Code of Federal Regulations are hereby incorporated by reference in their entireties (with respect to materials generally recognized as safe (GRAS)): §§5, 25, 170, 172, 173, 177, 182, 184, 186, 570, and 582.

I have discovered the basis for a dependent unifying medicament composition of matter which serves the basis for synergistic healing tissue regeneration activity analog to and mimicking not only embryonic stem cell but adding concentrated adaptive components to provide further therapeutic synergy when used alone or in combination with stem cell therapy.

This composition comprises (1) L-amino acids and glycine; (2) cell membrane components; and (3) ECM, which also includes the colloid matrix tissue water imbibing, additionally unique combination of colloidal factors and emulsifying factors, was not anticipated in the prior art. I have not found that those skilled in the art of emulsion technology (who also practice the art of colloid technology), let alone the incorporation and integration of bio-chemistry, bio-physics, clinical medicine, therapeutics and drug discovery required for this integration into a vital tissue therapeutic efficacy. All this has been accomplished without any of the major concerns and breaches of bioethics.

(1) polar surface active lipids of anabolic tissue components comprising (and endowing the healing and tissue regeneration components of normal tissue representative of tissue) in their normal ratio including components to contribute, produce and maintain the vital colloidal and emulsion systems of the body. All components in accordance with the genetic code and stem cell tissue without standing features of promoting tissue healing and tissue regeneration;

Embodiments of molar ratios of human tissue include fibrinogen, endorphin, breast tissue and its holocrine gland equivalent breast milk, may include muscle protein such as myoglobin which may be calculated as listed in biochemical text references containing in this case 153 L-amino acids and glycine (SEQ ID NO: 1): GLSDGEWQLVLNVWGK-VEADIPG HGQEVLIRLFKGHPETLEKFDKFKHLK-SEDEMKASEDKKHGATVLTALGGILKKKGHHEAET KPLAQSHATKHKIPVKYLEFISECIIQVLQSKHPGDF-GADAQGAMNKALELFRKDMASNYKE LGFQG, from which amino acid list molar ratios are readily calculable.

(2) The foregoing synthetic stem cell-like therapeutic subject composition must be prepared free of catabolic components and factors (that counter the maintenance of required equilibrium such as hydrolipophilic/lipophilic equilibrium balance factors that maintain the body's emulsion and colloidal states and that are antagonistic to anabolic tissue components and further unwanted synergism contributory to disease mechanisms) such as, and not limited to stereo three-dimensional misfits including D-amino acids, and disease response products of debris (that extending disease mechanisms by seeding of crystallization and causing crystalline matter that promotes foreign body reactions of disease) and protein or DNA not in accordance with the genetic code and without any protection for protein misfolding that promotes crystal shard formation and foreign body rejection reactions of disease. Composition components are optionally inclusive of extracellular matrix post translational protein which is not contrary to the genetic code. Catabolic products further to be excluded: Microorganisms intact or killed as in pasteurized products such as milk and dairy products (such organisms can be excluded via ultrafiltration).

Bringing protein synthesis as a means of anti-disease therapy where the molar ratio of the component protein amino acids not only satisfies normal human tissue but also approaches the formation of fetal human tissue is a goal of the subject invention. This protein synthesis also thereby more readily and synergistically satisfies another equilibrium of protein synthesis, and thereby reverses the negative nitrogen balance equilibrium characteristic of disease. This positive nitrogen balance equilibrium satisfies the law of mass action by offering these pre-formed monomeric components of human tissue protein to synergistically expedite complete tissue protein synthesis resulting in a more feasible drug dosage with more patient compliance. For example, compositions of the subject invention can contain a dosage of 50 to 100 grams of L-amino acids and/or glycine in contrast to an 80% to 90% larger dose of 500 grams per day which is no longer considered an acceptable dosage for medication.

Additionally, monomeric amino acids of the subject composition can be substituted with other monomeric amino acids. For example: tyrosine (P) (with two hydrophilic hydroxyl groups) is a potential substitute for phenylalanine (F) (with only one hydroxyl group). Similar conservative substitutions include: glycine (G) for alanine (A); methionine (M) for isoleucine (I); glycine (G) for valine (V); aspartic acid (D) for glutamic acid (E); isoleucine (I) for valine (V); serine (S) for threonine (T), arginine (R) for lysine (K). Of course, the reverse of these amino acid substitutions can also be performed at the discretion of the practitioner.

We have thus countered two disruptive equilibrium of disease: (1) the negative nitrogen balance and (2) the disrupted hydrophilic lipophilic balance equilibrium. In so doing we have (1) expanded the genomic environment thereby adding therapeutic elements while minimizing genetic pre-disposition estimated to be present in ⅔ of all diseases, and (2) we have corrected the gastrointestinal and subsequent tissue environment initiating the disturbance in the HLB balance.

This therapeutic composition of matter incorporates the pivotal strategic components that maintain and form these emulsion and colloidal micellar charged particulate matrix states as an anabolic organized structural and functional cell and its cytoplasmic, nuclear and organelle components along with tissue and organ states that are analog and mimic the component factors and forces of the tissue healing regenerating stem cell. This is in sharp contrast to disease and its associated components factors and forces that contribute to disorganized clumps of cells and their organelle and nuclear contents that not only lack these required unifying forces in disease states but are also catabolic and disruptive to the state of normalcy and health that stem cell therapy contributes.

(3) Furthermore to this therapeutic end, the synthetic stem cell-like subject composition of each of component 1, 2 and 3 serving as emulsion forming and thereby unifying liquid crystal micellar polar surface active lipid with components of No. 3 also contributing to the unifying colloidal state all analog to and mimicking in a unitary modus operandi through biomolecular engineering of the bio function and structure of the stem cell. It is this unique strategized fit with specialized variations (countering through these embodiments specific dysfunctional disease groups), that gives this synthetic stem cell like therapeutic composition the capacity to mimic and be analogous to the naturally occurring stem cell. Component No. 2 contains self-vesiculating essence of HLB 8 to 11 or 12, ideally 10 to 11, cell membrane forming and repairing liquid crystal phosphatidylcholine (PC), thereby increasing pliability of the red cell, blood vessel and endothelial membrane enhancing circulatory function by 25%. Component No. 2 optionally contains high HLB surfactants with packing parameters that not only enhance biologic function and efficiency of protein enzymes and their substrate but also promotes protein refolding and thereby normalizing biologic function. This helps to normalize the biologic function of disease promoting protein structures of Alzheimer's disease, Parkinson's disease, and Mad Cow disease. The high HLB (13 to 20, preferably HLB of 15 to 20) liquid crystal surfactants will also enhance fluidity thereby countering debris of disease, and respective seeding of crystallization with reversal of existent crystals. This may be documented by normal viscosity (Du nuoys of 1 to 3 centipoises). The same therapeutic component modality has been successfully used in-vitro to modulate mitosis with added maturation factor molecular component promoting apoptosis thereby normalizing cancer cells, highly unique, without any prior art anticipation that this polar surface active lipid surfactant would have any anti-cancer effect. These same HLB modulating requirements are used therapeutically here in these embodiments to counter clinically associated diseases such as, but not limited to obesity, atherosclerosis, and coronary artery diseases. In all these therapeutic applications of subject composition (in fluidizing with high HLB surfactant(s)) optional pretreatment with (or administration of) low HLB surfactant(s) to disperse the fat phase can be performed to initiate the fluidizing that high HLB surfactant(s) will finalize in 4 to 12 hours.

Additional discoveries include that these selective concurrent components with the foregoing specific exclusion features not only allow but facilitate, accelerate and synergize tissue healing and tissue regeneration. When combined with component No. 3 (collagen-cartilage) these unique synergistic features permit components No. 1 and No. 2, with L-amino acid and glycine in molar ratios that mimic human tissue, to be used effectively at reduced daily dosages of 10% to 20%, (50 to 100 grams) facilitate patient compliance and do not require hospitalization for intravenous or stomach tube administration. This is contrasted with daily dosages of 500 grams of amino acids in elemental feeding, which are formulated as nutritional food replacement feedings and are met with poor compliance that often require hospitalization for intravenous feedings or stomach tube administration.

This therapeutic composition is directed to the protein assemblage synthesis system and additionally includes all the polar surface active lipid surfactants and L-amino acids and non-chiral glycine (the lipophilic of which is primarily comprised of essential amino acids and constitutes the hydrophobic core of proteins). The hydrophilic components, primarily non-essential amino acids surround and form the periphery of the folded protein macromolecule. These polar surface active lipid surfactant forces are responsible for the final folded protein and its biologic activity associated with zeta potential charged clathrate thereby providing the intra-molecular bonding, electrostatic bonding and van der Waal forces with associated energy and entropy forces.

Cell nuclear and organelle membranes with HLB of 8-12 are comprised of polar surface active lipid liquid crystal surfactants, thereby utilizing the same intra-molecular inter-molecular foregoing bonding forces and associated energy and entropy forces, further comprising the omega 3 fatty acid fats (lipase activated in-vivo in the intestinal tract only to be further activated in the cellular membranes as a biologic antagonistic of highly inflammable chemokine mediator prostaglandin two) and the high 13-20 HLB surfactants and the fat dispersing low 1 or 2 to 7 HLB surfactants.

Extracellular matrix polar surface active lipids surfactants further comprising glypicans, utilize the same intra-molecular inter-molecular foregoing bonding forces and associated energy and entropy forces with the associated beneficial function and structure to further modulate vital organelle with particular reference to maintaining the normalcy of mitosis and thereby therapeutic anti-cancer function.

All foregoing polar surface active lipids provide the basis of charged and bonding forces and mechanisms with the unique synergistic component of hydrogen bonding in the clathrate cage structure non-liquid water format.

These bonding features maintain life through its colloidal matrix mediated more so by hyaluronic acid a macromolecule central to the proteoglycan aggregate complex cartilage (imbibing large amounts of water forming a viscous hydrous colloidal gel which gives shock absorbing and lubricant effects, particularly in synovial membrane joint cartilage connective tissue ECM, proteoglycan aggregate complex particularly so with macro molecular bio efficacy of hyaluronic acid biomolecular centrality in cartilage of component No. 3 and component No. 2 emulsion oil and water matrix systems with pivotal effect of the liquid crystal surfactants polar surface active lipids and their highly effective surfactant packing parameters increases surface area and zeta potential hydrogen bonding electrostatic forces and van der Waal forces) and thereby prophylactically and therapeutically lead therapeutic "combat" in normalizing the forces of disease that promote the breakdown of the systems representative of disease, liver disease or skin death. Without these components we would be "only a lump of cells (Robbins, Harvard edition pathology text).

These three component of therapeutic synthetic stem cell like subject composition polar surface active lipids surfactant component share semiconductor signaling systems with extracellular matrix component (ECM) component No. 3 (comprising collagen, fibronectin, laminin, and integrins, associated growth factors and protein aggregates including vinculin, talin, alpha actinin) and various combinations thereof signaling protein synthesis (associated with component No. 1), a cell growth and differentiation and motility by collectively initiating and integrating intracellular and intranuclear messages and nuclear signals.

In addition, the liquid crystal high HLB component No. 2 prevents and reverses non metabolizable debris of disease seeded crystals of cholesterol crystals, calcium phosphate crystals, uric acid crystals, pigmentation debris exogenous disease causing crystal shards such as silica and asbestos. The relation of inflammation and cancer can be illustrated by the unfortunate pathologic ending to asbestosis of cancer, mesothelioma, with the clinical therapeutic applications herein of this science and therapeutic synthetic stem cell-like subject composition.

Component No. 3 can further include all the hydrophilic components of extracellular matrix such as, but not limited to, the proteoglycan aggregate complex of cartilage containing hyaluronic acid covalently bonded to extracellular matrix protein and further non-covalently bonded to sulfated GAG such as, but not limited to, chondroitin sulfate.

(1) The subject composition also provides a "unique and novel and exciting in that therapeutic product and action in the patient is dependent upon the completion of the final activity and activation steps and in a sense, the final touches of "manufacturing" steps of this therapeutic product occurs in vivo in the patient";

(2) The subject invention completes the therapeutic composition to make non-healing tissue heal and regenerate;

(3) Prior to the subject invention, those skilled in the art were unable to use Periodic Table as utilized in PDR pharmaceutical and chemical plant whose manufacturing action is complete per se and only in vivo processing primarily concerns excretion and prior inaction;

(4) The subject invention uses pre-made (until available synthetically as in the analog case historically and in the case of past drug discovery and pharmacognosy of thyroid and insulin made available from the major meat packing houses) biologic chemical components with the practicality and safety of GRAS components significantly expediting and maximizing the practicality of new product discovery and development making these products readily available for market and patient use; components No. 1 and No. 2 contain essential components and that the body cannot synthesize (e.g., essential amino acids); component No. 2 contains essential lipids including omega 3 fatty acids (which become activated by lipase pancreatic enzyme in the small intestines and alkaline medium and which are inactive until hydrolyzed into fatty acid and glycerin as exemplified by documentation in heart muscle cells in vitro) in normalizing and preventing fatal dysrhythmia); and component No. 3 contains polar surface active ECM lipid glypicans (one of the three major classes of proteoglycans GAG with its lipid foot anchor on the adjacent (primarily lipid) cell membrane).

(5) Stem cell-caused healing and tissue regeneration can be maintained if contact associated with component No. 3 highly hydrophilic extracellular matrix components along with foregoing glypocans in toto as analog and stimulating the activation of the stem cells in other organs, (specifically exemplified by ECM basement membrane component=Heparan Sulfate GAG a sugar polymer highly polar negatively charged surface effect in common with polar surface active lipids permitting the maintenance of activation of the stem cells of the skin in normal spontaneous skin repair and regeneration after injury). This extracellular matrix basement membrane surface effect in maintaining stem cell character includes interaction with collagen, with several ECM macromolecules illustrating the rationale of the extracellular matrix and component No. 3 stem cell-like subject composition therapeutic effect characteristic including the glycoprotein laminin, the highly sulfated glycoprotein entactin as well as heparan sulfate GAG, extracellular matrix components included in other embodiments. These foregoing proteoglycan are noncovalent electrostatic interaction charged bonds between the negatively charged GAG and positively charged extracellular matrix proteins. Cartilage cells or chondrocytes in a similar ECM contact fashion also remain differentiated only as long as they are in contact with collagen.

(6) Additionally, a similar surface stimulus effect was noted in Steri-strip suture less wound approximation and healing (in view of suture intolerance and breakdown because of prolonged steroid use) wound edges contact approximation, repairing the rift in the basal epithelial proliferating cells and associated stem cells and their stem cell basement membrane maintenance contact with ECM collagen, proteoglycan aggregate complex which stimulated skin cell differentiation accelerating healing, the absence of scar formation, and stopped proliferation and migration of epidermal cells in conjunction with local and systemic therapeutic stem cell like composition.

(7) In further keeping with the synthetic stem cell-like synergistic formulation component collagen and its associated proteoglycans, the therapeutic stem cell-like composition has been found: (1) to maintain the stem cell activity, (2) to be one of the first substances to be formed after cleavage of the fertilized ovum again showing its importance in the stem cell activity), (3) stem cell activity is again seen when collagen-cartilage is added to a wound and thereby stimulates healing, and increase the hill disease or wound tensile strength by more than 48 percent, (4) directing the L-amino acid and glycine to stem cell tissue protein formation is synergized by analoging molar ratios of human tissue profiles (focused in continuation of fetal and embryonic analog to breast milk and breast tissue best directed and utilized in and the specialize in these are the developing embryonic fetus and neonate with the largest population of stem cells). These stem cells activated efficiently with significantly more focused on stem cell tissue protein synergistic through these synthetic stem cell therapeutic subject compositions thereby providing lower effective dosage requirement associated with maximal bioefficacy and biosafety and patient compliance for tissue healing and tissue regeneration than in the nutritional form.

(8) All components, and potential further added components for special disease groups, provide for therapeutic application of the subject technology that when co-used maximize efficiency and therefore lessen the required dosage of each component through their synergy (directed to this stem cell-like therapeutic subject composition dedicated to stimulate, facilitate and accelerate in-vivo the patient's stem cells thereby promoting this tissue healing tissue regeneration effect). This in turn, through progressive intermediate steps, finalizes in-vivo the ultimate activated therapeutic pharmacodynamic medication.

(9) The body's further action on components Nos. 1, 2 and 3 with the optional addition of further components as outlined in these embodiments including components No. 4 and No. 5 to products is devoted to excretion and metabolic degradation that precedes excretion of these products.

(10) I have in conclusion further unexpectedly discovered through these series of inventions many medicaments to help reverse groups of diseases through the medium of this stem cell-like therapeutic composition. The further basis of which is extracellular matrix representation as mesodermal and future mesenchymal tissue which has the ability intact to maintain stem cell activity of the skin. For example, if the skin basal epidermal stem cell layer is separated or severed or broken as in a wound from the underlying collagen proteoglycan aggregate complex of basement membrane stem cell surveillance that healing tissue regeneration is arrested. Molecular embryologic studies prove if the mesoderm and its future extracellular matrix are removed from its normal intermediate contact position these ectodermal and endodermal surfaces degenerate.

(11) Variants of these components with further specialized biologic effect can be found in the developing fetus with the largest population of stem cells, and sourcing from various species so provides representative biomolecularly "origin of species" also seen fetus provides these specialized functions and therapeutic opportunities. For example, the allantoic stage of the developing fetus produces readily soluble allantoin as to animals and birds a product of purine metabolism in its urinary tract, whereas the adult excretes highly insoluble uric acid making some adults prone to gout. By deriving enzymes such as uricase, from such animals, the soluble stage of allantoin can be achieved thereby alleviating the metabolic disability of gout. This analog sourcing of enzymes or synthetic models for synthesis offer many other such examples of therapeutic application.

For example, in addition to shark and cow tracheal cartilage, none of the cartilage at this specified level has proceeded to bone formation. For specialized therapeutic indication and application in impending amputations, such as, but not limited to, the use of stone crab, starfish, (echinoderm biologic class) and newt (salamandridea family, an amphibian), extracellular matrix (or cartilage), with multiple enmeshed growth and de-differentiation biologic factors, from an animal that can replace its own amputated limb and is in the activated biologic process of so doing can be utilized. This initially can be administered as a food and then ultimately desiccated and pulverized in accordance with the state of the art of production of biologic extracts. This de-differentiation extracellular matrix mechanism added to ECM component No. 3 (synthetic stem cell like therapeutic composition comprising components No. 1, 2, 3) a starting dosage of 1 to 2 grams ideally taking compositely and synergistically with the other three components but optionally may be used alone three times a day could prove of significant value in a patient such as a soldier suffering from impending phases of traumatic amputation on the battlefield. A dosage range 1-50 grams, added to ECM of component No. 3, specializing and varying these options according to the challenging needs of the disease in question.

(12) This may be further exemplified by drawing from the functional advantages of cellular membrane CM component No. 2 with the use of polar surface active lipids liquid crystal high HLB surfactant such as but not limited to Tween 80 in a cancerous group of diseases to modulate functionally than the nuclear organelle in mitotic organizing center mitosis and apoptosis to normalize the cancer cell. This subject therapeutic composition of matter opportunity can be further maximized by comparing therapeutic response results with esterifying the ethoxylated grouping with an additional 20, 40 and 60 or more moles of esterified ethylene oxide to achieve the results desired. Again this therapy may be used alone but ideally further synergized as part of a component No. 2 of the entire three component synthetic therapeutic stem cell-like subject composition. Additional synergistic efficacy of the subject compositions in expanding, synergistically, the genome (potentially mutated) can further normalize DNA along with antioxidants vitamins E, C, and A and synergistically broadening this unique composition for use in anti-cancer activity. Other enzymes otherwise normal but deficient such as but not limited to polymerases may be activated, facilitated, stimulated and synergized by the packing parameter efficiency and increase of surface area by the same polar surface active lipids liquid crystal surfactants. The foregoing are representative of medicaments and drug discovery application technology in therapeutic compositions unanticipated in the prior art.

(13) The same foregoing therapeutic, biomolecular pharmacodynamic application technology may be applied to the proteinopathy pathogenesis of Alzheimer's, Parkinson's, Mad Cow disease and associated human transmissible diseases resulting from mis-folded proteins from Alpha Helix random coil, to abnormal beta sheet, and reverse the folding mechanism with the foregoing high HLB surfactants.

Captured in this medicament are all of the vital healing and tissue regeneration forces of the living stem cell, unanticipated in the prior art, not only strategized, in biomolecular engineering as such but also established bio-efficacy as such. The achievement of this goal with such a degree of bio-efficacy and safety was not only unanticipated by the prior art but this degree of excellence of reproducing the vital force and effect of live tissue was not anticipated by the inventor. It is only through this extension of strategized vital tissue that this healing tissue regeneration therapeutic factor with all its components and bioefficacy can be extended for further continued replication into the tissue itself, an unanticipated accomplishment in therapeutic agents to date.

For example, fetal neonate tissue (whose amino acids molar ratios are analogous to and mimic the tissue and its properties of tissue healing, tissue restoration and regeneration) with further unique combined properties of protein synthesis coupled with anti-inflammatory activity as well as a genetic factor not found in anti-inflammatory medicaments of the prior art. Additionally not found in the prior art is the selective choosing (from the biologic period table) of amino acids in medicament dosage form synergistically adapted to the human stem cell function (in contrast to the multiplicity of nutritionally based elemental feedings used as a medical food rather than a medicament.

I have additionally discovered and utilized a unifying cell and tissue composition that is analogous to and mimics the structure and function of the stem cell emulsion and colloidal bonding force and matrix that extends itself to the tissues. The composition can be given, not only parenterally, but more importantly, orally, with further benefit of the oral mucosal delivery system. These bonding forces are liquid crystal surfactant micelle polar surface active lipids incorporate the zeta potential, hydrogen bonding and clathrate structured, non-liquid, water cage, thereby, extending and disseminating this tissue structure bonding and unifying force to the patient's tissues.

Most important of all in this therapeutic breakthrough, unanticipated in the prior art, is the anti-cancer activity, independent of all the prior strategy of killing the cancer as if it were an infectious microorganism, but instead adopting a normalizing factor in the treatment of cancer: modulation and normalizing mitosis using highly hydrophilic liquid crystal micelle surfactant fluidizing (with an ethylene maturation factor) and normalizing the cell and tissue with its progression of maturation to apoptosis.

In regard to pathogenic microorganism antibiotic resistance and testing for same in vitro the addition of component 2 alone, and in toto combination with the subject composition may counter microorganism pathogenic components such as lipid A and LPS lipopolysaccharide.

Omega 3 oils and Vitamin E (100 units), can be added as a synergistic antioxidant and anti-rancid component further with the omega-3 fish and seed oil synergistic to the anti-inflammatory efficacy of the component 1. In vivo activated, further promulgating and synergizing anti-inflammatory activity without disrupting the essential tissue replacement component of protein synthesis, not found or anticipated in all prior art and anti-inflammatory compounds.

Extracellular matrix (ECM)—only animal tissue of these components—non mammalian thereby any DNA would be unique enough so that not recognized as potentially damaged DNA that could bring about unwanted mutations from which catabolic disease producing factors could be antagonistically derived.

In allergic anaphylactic type rejection like reactions in regard to multiple severe food allergies distant biologic components sourced from non-mammalian animals (such as amphibian derived foods have been found to serve as a universal food donor) can be used. Extracellular matrix components additionally can, preferably, be utilized in this therapeutic composition in the encapsulated powered form, in contrast to a compressed tablet.

This continuity of proliferating cellular contact with extracellular matrix collagen proteoglycan aggregate complex as exemplified by, but not limited to the basement membrane and the ECM collagen contact supportive maintenance of the active skin stem cell layer, similar observations have been made in the cartilage cells or chondrocytes correlating ECM contact with similar stem cell activities in cartilage tissue. Similar correlation has been noted with regard to cartilage placed in a wound with activation of stem cells accounting for the stimulation of wound healing associated with about a 48 percent increase in tensile strength of healed wound.

The same therapeutic and prophylactic concept can be used in the unfortunate possibility of a bioterrorism attack (mediated by nuclear, microorganism, or biochemical agents). Therapeutic composition of the subject invention can also be used in the treatment of soldiers on the battlefield.

These anabolic components may be derived from a "biologic periodic table" with available biochemical formulations of tissue polypeptides and tissue polypeptide proteins from which molar ratios may be readily calculated (sources include the Merck index, the Code of Federal Regulations (CFR 21), and public databases that provide the amino acid sequences of known proteins and polypeptides.

Component No. 1—the anabolic amino acids in molar ratio of embryonic fetal neonatal human tissue in the monomeric amino acid form of breast milk and breast tissue. This synergistic human tissue molar ratio synergizing and expediting through the mechanism of the law of mass action the final polymerized stem cell tissue protein along with its significant anti-inflammatory activity through amino acids that are analog to C 2, 3, 4, 5 and 6 anti-inflammatory medications.

Component No. 2 can be used independently of, and synergistically with component No. 1 and provides polar surface active lipid liquid crystal micelle with biochemical essences of cell membrane (CM). Component No. 2 can include phosphatidyl choline (PC), omega-3 fish oil, and seed oils.

These highly hydrophilic polar surface acting lipid surfactants also may be utilized therapeutically in treating diseases mediated by mis-folded proteins, including Alzheimer's disease, Parkinson's disease, Mad Cow disease and its human transmissible equivalent.

Component No. 3 comprises extracellular matrix (ECM), glypicans, and/or fibronectin, collagens, proteoglycan, glycosaminoglycans, fibrinogen, and fibrin.

Fibronectin may also be used in conjunction with other structural glycoproteins such as osteonectin SPARC secreted proteins rich in cysteine, osteopontin and osteocalcin in addition to tenascin present in stem cell containing tissue such as periosteum. These component compounds may be used in dosages in this therapeutic subject composition, of one half to 2 grams with a range of 1 to 50 grams preferably of fibronectin laminin structural glycoproteins in addition to collagen and associated proteoglycan aggregate complexes when possible derived from ECM of amphibian animals such as reptiles and crabs (stone).

This tissue healing tissue regeneration therapy can be used in conjunction with many other therapies that have dramatic therapeutic effects and high incidence of side effects that has heretofore minimized their popularity and value. Administration of this synthetic stem cell like subject composition to these patients can protect them from these side effects and the side effects can be greatly minimized. The same therapeutic and prophylactic concept can be used in the unfortunate possibility of a bioterrorism attack, (mediated by nuclear material, microorganisms, chemical agents) or in speeding tissue healing and tissue regeneration of soldiers on the battlefield.

Innovative Bio-Pharmaceutical Countermeasures to a CBRN Attack.

Statement of the Problem being Addressed:
  A major concern in dealing with the nation's newest enemies, that have already carried out terrorist attacks on both our military forces and civilian populations, is that they will momentarily escalate their assault on the U.S. to include the use of chemical, biological, radiological and nuclear (CBRN) attacks, for which, at present, only inadequate countermeasures or remedies exist.
  Research personnel in the medical, biological and physical sciences, who have a track record of successfully undertaking multidisciplinary programs that result in novel, cost effective solutions to vital national problems, are here today to offer DARPA a bold, highly innovative, bio-pharmaceutical therapeutic advance, as a countermeasure to potential chemical, biological, radiological and nuclear terrorist attacks.

Brief Summary of the State of the Art:
  A commonly utilized reference book for physicians is the "Physician's Desk Reference" (PDR), that contains a section entitled PDR Guide to Biological and Chemical Warfare Response, as well as a section on Nuclear Radiation.
  The PDR contains information for a wide range of bacteriological agents including, for example, anthrax, and for various chemical agents. It describes the clinical effects that are commonly observed, and indicates what treatments may be helpful.
  Unfortunately, in too many instances, including nuclear radiation, no active treatment is offerable that can save the patient.

Proposed New Technical Approach:
  In general, medicine's approach to disease processes, including:
    malignant processes
    infectious processes and agents
    abnormal proteins
    pathogenic processes abnormal mis-folding of protein in the form of beta sheets in contrast to normal alpha helix and random coil has been to target attacking the diseased cell, with the pharmacological approach of eliciting a cure by cell death, either direct or indirect.

The above pharmacological technological approach using these lethal agents has been initially dose-calibrated by LD50 tests of animals to assess their lethality and relative biosafety.

Another approach to countering disease processes can be correlated with the 21$^{st}$ century breakthrough of stem cell therapy included in oncologic therapy.

Looking into the environment surrounding each cell, we discovered a colloidal microcosm that we know is representative of our synthetic stem cell-like liquid crystal formulation.

This synthetic stem cell-like medication which is analog and mimics the stem cell and its tissue in its component structure and function, as well as based upon bio-emulsion and bio-colloidal structural formulations, and further mimicking human tissue is additionally unique in that it does not require human tissue for its preparation.

This proposed new bio-medical approach:
  stimulates, accelerates and facilitates the patient's own stem cells with bio-safety and the bio-efficacy of the stem cell and augments any form of stem cell therapy
  makes it possible therapeutically for the first times to encounter disease in cooperation and in conjunction with, offering therapeutic medication which is incorporated in-vivo with the patient's own tissue resulting in healing and tissue regeneration.

This new approach to pharmaceutical healing in disease management is representative of 20 successive filed patent application inventions including an anti-inflammatory medication inclusive of stimulation of protein synthesis and an anti-cancer therapeutic medication, while preventing multiple side effect risks of existing therapeutic agents.

This new technical approach is based on:
  A synthesis of clinical experience including multi-center studies of more than 450 patients and 150 clinical controlled studies with an 85% efficacy in both groups, and in vitro anti-cancer controlled studies including modulation and normalization of mitosis.
  Studies thus far have included:
    normalization of the body's inflammatory response and associated protein synthesis
    mitosis modulation effects
    anti-cancer activity of this synthetic stem cell-like medication
    effects of minimizing radiation and chemotherapeutic dosages.
  Diagnostic procedures utilized in studying the comparative microscopic geometric morphology have included:
    polarizing microscopy
    X-ray diffraction techniques.

These studies have produced exciting results in which it could be discerned that under specific test conditions:
  The type of liquid crystalline phase aggregation of the component surfactants with a low packing parameter revealed reverse hexagonal phase rods of water surrounded by emulsifier, which correlates morphologically with the abnormal mitosis of cancer.
  The macroscopic appearance of this phase of bio-emulsion and bio-colloid configuration revealed lumps of emulsifier in equilibrium and a surplus of water.
  Use of the surfactant packing parameter formula indicated the least surfactant packing parameter, and associated least repulsive particle charge.
  It is noted that the patent pending stem cell repair kit bio-colloid and bio-emulsion format and composition is normally present in human tissue but is not derived therefrom.
  Furthermore, this liquid crystal technology intrinsically provides for and allows the three-dimensional macromolecular structure, as well as intra-molecular folding. The presence of this liquid crystal also allows continuous surveillance and maintenance to keep the cell normal.

Our preliminary conclusions are:
  The patent pending liquid crystal formulation and concept allows us to rethink our approach as to how cells or macromolecules such as proteins maintain normalcy.
  Our patent pending medications were derived by utilization of custom tailoring of the components of this liquid crystal formulation to more specifically targeted therapeutic requirements of the disease process.
  Remarkable bio-safety has been observed in the research to-date.

Expected Results:
The new operational capability that would be provided:
  Biologically safe, efficacious, therapeutic compound, readily taken orally or by injection.
  Heightened immunity when taken in advance of a terrorist chemical, biological, radiological or nuclear (CBRN) attack.
  Accelerated healing when taken following a terrorist CBRN attack.
  Protection of the entire population at risk of infliction of a terrorist CBRN insult, by mitigation of lethal morbidity (by prevention of sickness) and lessening of mortality (by prevention of death).
  Dosage in proportion to body mass.

Cell Biochem Stem Cell Repair Kit, a Liquid Crystal Formulation and its Role in Reduction of Pathogenesis In general, medicine's approach to disease processes, whether they be malignant, processes, infectious processes and agents or such as an abnormal protein or other pathogenic processes that have been correlated with progressively newer findings of disease processes such as the association of the abnormal mis-folding of protein in the form of beta sheets in contrast to normal protein of alpha helix and random coil, (i.e., Alzheimer's disease, Parkinson's disease, Mad Cow Disease and its human transmissible encephalopathy, abnormal Prion (sc) Disease) have been targeted by attacking the diseased cell with the pharmacologic approach of eliciting a cure by cell death either direct or indirect.

With pharmacologic technologic approach using these lethal agents have been initially dose calibrated by $LD_{50}$ tests of animals to assess their lethality and relative biosafety.

Another approach to countering disease processes can be correlated with the 21$^{st}$ century breakthrough of stem cell therapy included in oncologic therapy.

Looking into the environment surrounding each cell we discovered a colloidal microcosm that we now know is representative of our synthetic stems cell like liquid crystal formulation. This synthetic stem cell-like medication which is analog and mimics the stem cell and its tissue in its component structure and function as well as based upon bio emulsion and bio-colloidal structural formulations, and further mimicking human tissue is additionally unique in that it does not require any human tissue for its preparation. This medication stimulates, accelerates and facilitates the patient's own stem cells with bio-safety and bio-efficacy of the stem cell and augments any form of stem cell therapy. Thereby, making it possible therapeutically for the first time, to encounter disease in cooperation and in conjunction with, offering therapeutic medication which is incorporated in vivo with the patient's own tissue resulting in healing and tissue regeneration. This epitome of pharmaceutical healing in disease management is representative of 20 successive filed patent application inventions: an anti-inflammatory medication inclusive of stimulation of protein synthesis and an anti-cancer therapeutic medication, while preventing multiple side effect risks of existing therapeutic agents.

This medical product is a synthesis of clinical experience including multi-center studies of more than 450 patients and 150 clinical controlled studies with an 85% efficacy in both groups. In vitro studies include anti-cancer controlled studies including modulation and normalization of mitosis.

Having studied and normalized the body's inflammatory response and associated protein synthesis with this medication, other responses such as the cancer response were then studied. It was noted that this medication had a mitosis modulation, anti-cancer activity of this synthetic stem cell-like medication and its effect in minimizing radiation and chemo-therapeutic dosages was observed progressively as follows:

1) The comparative microscopic geometric morphology including studies of polarizing microscopy and X-ray diffraction that the type of liquid crystalline phase aggregation of these component surfactants with a low packing parameter revealed reverse hexagonal phase rods of water surrounded by emulsifier, which correlated morphologically with the abnormal mitosis of cancer. It was also noteworthy that the macroscopic appearance of this phase of bio-emulsion and bio-colloid configuration revealed lumps of emulsifier in equilibrium and surplus of water. Further characterized by the surfactant packing parameter formula indicating the least surfactant packing parameter >1 Ns (inversely proportionate to the surfactant packing parameter) and associated least repulsive particle charge. This is in sharp contrast to the other phases of this medication and tissue analog.

This formulation is explained in detail for a unique use in the normalization of the cellular environment (both internal and external structural support) by supplying this colloid and emulsion system to the cellular environment which was weakened, offering further protection to the cell from free at radical or radiation damage (see Example 13).

2) Putting this thesis to the test, in vitro, it was further found that the bio-emulsion and bio-colloid system components that favored the hexagonal micelle small spherical aggregate configuration with clear solution macroscopic appearance. This was noted incubating breast tissue in-vitro culture system with ¼ to ½% of the foregoing resulted in normalization of mitochondrial metabolic activity and histopathologically 50% reduction in the abnormal cancer cells histopathologic morphology including similar reduction in cells with their characteristic abnormal mitotic figures.

With the above formulation in mind several effects upon the milieu of the cell are as follows:
1) effect of colloidal surrounding water molecule This patent pending stem cell repair kit bio-colloid, and bio-emulsion format and composition is normally present in human tissue but not derived therefrom. This includes liquid crystalline bio-robotic components which are also semiconductor signaling mechanisms derived in accordance with the code of federal regulations from a patent pending bonding of biopharmaceutical biomolecular periodic table derived components. The bio-efficacy of these liquid crystalline components is measured by the following formulation of surfactant number and packing parameter strongly hydrated surface with structured water in contrast to liquid water and associated strong particle hydration.

2) The strong particle hydration and surfactant packing parameters result in highly repulsive forces of structured clathrate water in contrast to liquid water (with effect inverse to the surfactant packing parameter number) and equals <½. This Ns is derived from the formula v×l divided by $a_o$ in accordance with the formula wherein v and l represent the volume and length of the hydrocarbon chain. $C_2$, $C_3$, $C_4$, $C_5$, $C_6$, and $a_o$ is representative of the area of the amphiphilic molecular structure of these surfactant hydrophilic head groups of component #1, (10 to 25 grams loosely packed encapsulation tid).

Component #2 cell membrane composition includes liquid crystalline bio-robotic components that are also semiconductor biocomputer signaling mechanisms. The bio-efficacy of these liquid crystalline components is measured by the following formulation of surfactant number and packing parameter which equals ½-1 and is derived from the formula v×l divided by $a_o$ in accordance with the formula wherein v and l represent the volume and length of the hydrocarbon chain. $C_{16}$ and $C_{18}$ and $a_o$ is representative of the area of the amphiphilic molecular structure of these surfactant head groups component #2, (dosage 1-2 grams tid).

Component #3, extracellular matrix (ECM) glypicans, in the only extracellular membrane component with a liquid foot anchor with a C16 to 18 hydrocarbon chain with the same formulation and surfactant number and packing parameter which equals ½-1 is dependent upon chain length C16 to C 18 and volume of the respective hydrocarbon chain and $a_o$ is representative of the area of the amphiphilic molecular structure of these surfactant head groups of component #3, (dosage 1-2 grams tid).

The foregoing components #1, #2 and #3 are dependent upon in vivo entrapment of clathrate of structured water with reduced entropic energy forces.

The remainder of component #3, the bio-colloid component structure and function are dependent upon in-vivo non-covalent bonding of water (dosage 1-2 grams tid).

This liquid crystal technology intrinsically provides for and allows the 3-D macro-molecular structure such as proteins as well as intra-molecular folding. The presence of this liquid crystal also allows continuous surveillance and maintenance necessary to keep the cell normal.

Conclusion:

This patent pending liquid crystal formulation and concept allows us to rethink our approach as to how cells or macro molecules such as proteins maintain normalcy.

Patent pending therapeutic medications thereby resulted, by utilization of custom tailoring of the components of this liquid crystal formulation to more specifically targeted therapeutic requirements of the disease process.

1. Components #1, #2 and #3 comprise liquid crystal polar surface active lipids amphiphilic compounds that mediate the bio-emulsion water entrapment.

2. Component #3 also comprises non-amphiphilic bio-colloid water bonding compounds providing tissue turgor.

3. According to conclusions 1 and 2, mammalian, e.g. human tissue comprises 65% to 75% water structurally and functionally held as human bio-emulsion entrapped water or bio-colloid bonded water.

4. According to conclusion 3, mammalian, e.g., human tissue comprises cells, cell membrane and extracellular matrix providing cell and tissue structure other than a "clump of cells."

5. According to conclusions 1-4, bio-emulsion component surfactant packing number Ns is inversely proportionate to the packing number.

6. According to conclusion 5, the surfactant packing number relates polar surface active lipid surfactant amphiphilic molecular structure mathematically derived from the formula Ns is equal to V divided by $L \times A_o$ wherein L is the length of the liquid crystal surfactant polar hydrocarbon chain and V equals the volume of the surfactant hydrocarbon chain. $A_o$ equals the area of the hydrophilic head component of this amphiphile.

7. Non-catabolic medication components 1, 2 and 3, are tissue components of cellular, cell membrane, extracellular matrix and cell tissue mathematically expressed and dependent upon the mathematical formulations expressed in accordance with conclusion 6.

8. According to conclusion 7, these bio-chemical and bio-physical components mimic and are analog to human tissue but are not dependently derived from human tissue.

9. These components are derived from a biologic periodic table according to the code of Federal Regulations CFR21 with tissue healing and tissue regeneration capacity.

10. The non-catabolic tissue healing tissue regeneration capacity does not inhibit the protein synthesis of tissue healing because of the tetrahedral fit of the alpha carbon in the polypeptide protein chain.

11. According to conclusion 10, compositly therefore represent the components of the human stem cell according to the foregoing conclusions and conclusion 1 unite therapeutically in-vivo as cellular, cell membrane, extracellular matrix, cell and tissue analog and mimicking human tissue, resulting in the formation and regeneration of healed human tissue.

12. According to conclusion 1, the intrinsic interactive interplay of hydrogen bonding electrostatic forces and van der Waal forces and C2 to C6 amino acids result in a protein molecular folding characterizing the bio-activity of macromolecules as protein resulting from its template action of DNA upon RNA upon ribosomes.

Pharmacology and Pharmacodynamic Rationale Sourcing of Q101 KC for Crohn's Disease and Pediatric Crohn's disease.

Q101KC:

In summary, the synergistic anti-inflammatory effects of components of #1, 2, and 3 are:

component 1: 80% reduction of inflammatory chemonikines component 2: Biologic competition countering prostaglandin (PG2)

component 3: Reduction of new blood vessel angiogenesis thereby reducing inflammatory response Summary of the tissue healing and regeneration effects of Component Nos. 1, 2, 3, 4 and 5 are:

Component No. 1: tissue protein synthesis and cell membrane repair

Component No. 2: cell membrane repair and replacement

Component No. 3: 48% increase in tensile strength

Component No. 4: 90% reduction and risk of sepsis (Balanced B complex including B2 and B12)

Component No. 5: implantation symbiotic probiotic bacterial flora to perpetuate the prevention of tissue damage and replacement of deficient enzymes which together perpetuation the effects of Component No. 1.

The bio-science of Q101KC is based upon a series of patent pending non-covalently bonded inventions serving as therapeutics of CD (Crohn's Disease). As seen here, particularly important in a chronic disease such as CD, the failure of healing is the basis of the chronicity of the disease. Therefore this is the basis of the direction of this treatment. This can be best appreciated by realizing that disease, as well as wound healing and tissue regeneration, represent an integral part of inflammation. Therefore, the same components that are crucial for providing molecular embryonic development may also serve as a 'stem cell repair kit.'

Once can now readily see why the stem cell (or its equivalent here) addresses these therapeutic needs. The development and sourcing of components of this CD therapy mimic human tissue in its structure and function.

The family of anti-inflammatory drugs, best exemplified by aspirin (ASA) and 5 ASA dramatically reverse inflammation. However, they also significantly impede tissue healing and tissue regeneration. These anti-inflammatory drugs impede healing and tissue regeneration through inhibition of protein synthesis; a therapeutic cost that a patient with a chronic disease such as CD cannot afford.

This molecular basis of Q101KC focuses on tissue healing and tissue regeneration, mimicking human tissue in all of its structures and functions. This molecular basis of therapeutics, presently directed toward Crohn's disease, utilizes non-covalent bonding along with the electrostatic charged particle potential of colloids, a significant feature of human tissue and also synergistic to healing and tissue regeneration. This treatment has been developed as a new patent pending, cost-effective drug discovery technology.

Q101KC facilitates, accelerates and synergistically reestablishes normal human tissue in accord with the intact colloidal domain of all tissues from the ECM (Extracellular Matrix). This proteoglycans complex binds large amounts of water forming a viscous hydrate gel, which gives connective tissue the ability to resist compression. The resulting resilience and lubricity and associated electrostatic charge increase tensile strength of disease tissue and improve wound healing by 48%.

The same advantages are endowed in the emulsion technology features of Component Nos. 1, 2, and the lipid anchor of glypicans of Component No. 3. Component No. 1 encompasses the 20 alpha amino acids of the human genetic code for tissue protein formation which is so imperative in the healing process. Component No. 2 provides for cell membrane regeneration in disease tissue by self vesiculation of PC** (phosphatidyl choline) in addition to the healing of cell membrane aided by the glycine amino acid component of #1, and also provides cell membrane-focused omega 3 antiprostaglandin, a potent anti-inflammatory factor. Working simultaneously and synergistically with Component No. 2 is Component No. 3, an ECM proteoglycans complex, which further normalizes human tissue and counters lipid prostaglandin's most profound inflammatory mechanism. Component Nos. 2 and 3 simultaneously and synergistically provide tissue healing and tissue regeneration.

The gel hydrate of the colloidal domain is remarkable and unique to this new drug discovery technology and Q101KC. Component Nos. 1, 2 and part of Component No. 3 with its lipid cell membrane anchor glypicans are similarly effectual in tissue regeneration and healing. The liquid crystal of all these forgoing components of emulsion technology aid in their liquid crystal alignment effects in the healing of diseased tissue as in CD.

Description of the Rare Disease or Condition, Proposed Indication, and Reason for Therapy.

Description of the Disease or Condition:

PCD, like Crohn's disease, is an idiopathic, chronic, transmural inflammatory process of the bowel that can affect any part of a child's gastrointestinal tract. The small bowel, and particularly the terminal ileum, is most commonly affected, although the colon, small intestine alone, stomach, and esophagus may also be affected. PCD is believed to result from an imbalance between pro- and anti-inflammatory mediators. PCD often presents itself with abdominal pain, weight loss, and diarrhea, which may be complicated by intestinal obstruction and/or fistulization.

The inflammation of tissue in PCD patients causes numerous complications. The most common complication is intestinal blockage. Intestinal blockage results from a thickening of the intestinal wall from swelling and scar tissue, which, in turn, narrows the intestinal passage. Although the obstruction in PCD patients is initially caused by edema of the mucosa and associated spasm of the bowel, and can be treated by anti-inflammatory agents (such as mesalamine), the obstruction can become chronic and cause scarring, luminal narrowing, and stricture formation, which require more serious intervention. PCD may also cause sores or ulcers that tunnel through the affected area into surrounding tissues, such as the bladder, vagina, or skin (enteroenteral, enterovesical, enterovaginal, or enterocutaneous fistulization). The fistulas in PCD patients often become infected and must be treated with antibiotics or surgery.

PCD patients also commonly have nutritional complications, such as protein, caloric, and vitamin deficiencies. These complications may be caused by inadequate dietary intake, intestinal loss of protein, or malabsorption resulting from the underlying disease. Other complications associated with PCD include arthritis, skin problems, inflammation in the eyes or mouth, kidney stones, gallstones, or other hepatic conditions. PCD has important features that distinguish it from adult Crohn's disease, including growth retardation (usually attributed to steroid therapy),[1] a high prevalence of osteopenia,[1] and several social and psychological factors.[1]

PCD's etiology is poorly understood, and is largely unknown. The scientific literature postulates myriad causes, including genetic, microbial, immunologic, dietary, environmental, vascular, and even psychosocial factors. PCD affects males and females equally, but appears to affect Caucasians more than other races, and the Jewish population more than other ethnic groups.

Unfortunately, there is no currently approved medication to cure PCD, and for some patients, intestinal surgery offers only a brief benefit before other areas of the intestine are affected again. There are several pharmacotherapeutic options that reduce PCD morbidity, prevent complications, and maintain a patient's nutritional status.

Proposed Indication:

This orphan drug designation request is for Q101KC (levorotatory amino acids; essential fatty acids; collagen; vitamin/mineral/trace element complex; probiotic complex) for the treatment of patients with PCD.

Reason for Therapy:

The current treatment options for PCD patients are less than optimal. While most available therapeutic options available to PCD patients are palliative in nature, Q101KC stimulates the synthesis of protein and cell membrane formation in PCD patients. This, in turn, repairs the tissue in the affected areas and reduces inflammation, and, in effect, reverses the PCD disease process. Q101KC thus offers a therapeutic option that is different from currently available options. Without such an option, PCD patients are left with few options, including the possibility of surgery and the lifetime use of potentially toxic drugs.

Product Composition and Formulation:

Q101KC includes five primary components: (1) levorotatory amino acids; (2) a complex of essential fatty acids (consisting of phosphatidyl choline, omega 3 eicosapentaenoic acid ("EPA"), and docosahexaenoic acid ("DHA")); (3) collagen; (4) a complex of vitamins, minerals, and trace elements of human tissue; and (5) a complex of probiotics (namely *lactobacillus acidophilus, bifidobacterium bifidum, lactobacilis bulgaricus*, and *lactobacillus salivarius*).

Rationale for the Use of Q101KC for the Treatment of Patients with PCD:

The rationale for the use of the three primary Q101KC components is to synergistically stimulate the synthesis of protein and cell membrane formation in patients with PCD. In effect, Q101KC regenerates affected (inflamed) tissue so that it can no longer have the effects on the body that it would otherwise have. Because tissue is regenerated, the need for anti-inflammatory intervention and/or surgery is significantly reduced.

Component 1—Levorotatory amino acids: to increase favor protein synthesis by altering the balance of free L amino acids.

Component 2—Essential fatty acids (e.g., phosphatidyl choline, EPA, and DHA): to correct cell membrane damage and to enhance the body's production of anti-inflammatory prostaglandin 3 and prostaglandin 1.

Component 3—Collagen/ECM [extracellular matrix] components: to stimulate the immune system and for tissue repair and anti-inflammatory anti-neogenesis.

Component 4—Vitamin/Mineral/Trace element complex: to stimulate tissue repair blocked by the underlying disease.

Component 5—Probiotic complex: to normalize abnormal microflora, tissue, and secretions.

Clinical Experience

Clinical experience with the components of Q101KC demonstrates that this product can safely and effectively treat patients with PCD.

Components 1 & 4—Levorotatory amino acids & Vitamin/Mineral/Trace element complex Several articles[1-10] show that elemental diets reversed growth failure, increased weight in children with Crohn's disease, and generally acted to reverse the symptoms of Crohn's disease comparable to steroid-treated patients resulting in significant clinical improvement.

Component 2—Essential fatty acids (e.g., phosphatidyl choline, EPA, and DHA)

Several articles—[1-4] show that essential fatty acids administered to Crohn's patients are an effective treatment for chronic inflammatory disorders such as PCD. Essential fatty acids reverse the inflammatory process and have been shown to maintain periods of Crohn's disease remission.

Component 3—Collagen/ECM [extracellular matrix] components:

Published literature[1-4] shows that collagen acts as an anti-inflammatory and repairs damaged tissue. Using collagen to treat patients with PCD should have similar effects and would also serve to wean patients off of the use of potentially toxic drugs.

Component 5—Probiotic complex

Bleichner, et al.[1] concluded that *Saccharomyces boulardii* prevented diarrhea in certain critically ill patients with risk factors for diarrhea, such a PCD. It is reasonable to conclude that other probiotics would have similar effects on PCD patients.

PCD, like Crohn's disease, is a type of inflammatory bowel disease ("IBD"). It is our understanding that FDA's Office of Orphan Products Development recognizes PCD as a distinct disease. Nonetheless, we note that Q101KC is specifically formulated for use in pediatric patients. Furthermore, the various side effects of current therapies (especially steroids, which have been attributed to growth retardation unique to pediatric patients and osteopenia) means that PCD patients require a treatment option without such significant side effects, like Q101KC.

Size of Patient Population

Although there is some variation among the published literature as to the precise prevalence of PCD, it is recognized as an orphan condition. In fact, In January 2003, FDA designated Alimentary Health Limited's *bifidobacterium longum* infantis for the treatment of PCD. The following prevalence figures are calculated using a United States population estimate of 288,368,698 residents (of which 81,022,584 are zero to 19 years old), as reported by the United States Census Bureau on Jul. 1, 2002.[1]

Cosgrove[24] reported an incidence of PCD in South Glamorgan, United Kingdom of 16.6 per 100,000 children under 16 years old. Although these data are from the UK, the population of the UK is presumably similar to that of the United States. As such, Cosgrove's incidence figure is relevant to calculating the prevalence of PCD in the United States. Using Cosgrove's incidence of 16.6 per 100,000 children and using an estimated United States juvenile population of 81,022,584, the prevalence of PCD in the United States is estimated to be 13,450.

Hildebrand et al.[25] reported an incidence of 21.5 per 100,000 children under 16 years old with IBD, including incidence figures of 2.7 per 100,000 for PCD and probable PCD, in a study conducted in southwestern Sweden. As with Cosgrove, the Hildebrand study was not conducted in the United States. Nonetheless, the study population may be representative of PCD in the United States. Assuming that all 2.7 per 100,000 children have PCD, and using an estimated United States juvenile population of 81,022,584, the prevalence of PCD in the United States is estimated to be 2,188. Even assuming that all 21.5 per 100,000 IBD children have PCD, and applying this incidence figure to an estimated United States juvenile population of 81,022,584, the prevalence of PCD in the United States is estimated to be 62,524.

Pharmacology and pharmacodynamic rationale sourcing of Q101 KC for Crohn's disease and Pediatric Crohn's disease (Patent Pending). So that the physician and health care professional can thereby logically and physiologically derive therapy.

Q101KC:

The bio-science of this new drug discovery is based upon a series of patent pending non-covalently bonded inventions serving as a Q101 KC therapeutics of CD (Crohn's Disease) As seen here, particularly important in a chronic disease such as Crohn's, as well as wound healing and tissue regeneration represent an integral part of inflammation (separated only heretofore didactically); while the same using components that are also crucial for providing molecular embryonic development therefore also serving as stem cell repair kit.

In the application of molecular embryology metabolic factors and enzymes maybe sourced at equivalent in this new drug discovery technology stage of animal development. This sourcing further corresponds to embryologic and molecular embryology and human embryologic development.

Therefore, while keeping with developmental inducing stem cell activity along with the genetic code (all sourced from non-human tissue, medical food sources) as plant or animal tissue derived biochemicals analog and bio-chemically equivalent to human tissue sourcing of Q101 KC is in accordance with GRAS code of federal regulations CFR21 all making possible foregoing file patent pending application of a new bio-scientific periodic table sourcing for new drug discover (In sharp contrast to covalently bonded elements of Mendeleev's periodic table requiring years to decades of trial and perfection, economic challenge that is not possible for major companies and the public to meet). Medically as well as economically advantageous: in that this gentle approach results in new medication with note worthy absence of side effects—bio safety companion to bio efficacy.

This molecular basis of therapeutics of disease such as Crohn's disease developed as a new patent pending cost worthy drug discovery technology not only featuring non-covalent bonding whose effects are synergistic to the electrostatic charged particle potential of colloid therapeutic domain.

Component Nos. 1 and 2 are of small molecular composition, Component No. 3 primarily of large molecular composition representing approximately 10% of Q101 KC (70% a absorbed intact) Component No. 3 ECM. The development and sourcing of components of this CD therapy are always conformant to the genetic code, mimicking human tissue in it's structure and function (ECM post translational modifications) and are also represented here as a progressive series of in utero organ tissue molecular embryologic developments with stem cell inducing activities.

All the foregoing new drug development such as Q101 KC therapeutics of CD permit the facilitating, accelerating and synergizing the healing and tissue regeneration. Therefore reestablishing disease tissue to normal human tissue in accord with the intact colloidal domain of all tissues from the ECM (Extracellular Matrix). The proteoglycans complex binding large amounts of water forming a viscous hydrate gel which gives connective tissue ability to resist compression therefore resilience and lubricity and associated electrostatic charge resulting in increase tensile strength of disease tissue and wound healing by 48%, Component No. 3 as provided in shark cartilage 0.74 gram/capsule also includes collagen and chondroitin sulfate as 5 capsules 3.7 grams BID to TO cartilade, Fairfield, N.J.

The same advantages are endowed in the emulsion technology features of components 1, 2 and lipid anchor of glypicans of Component No. 3 ECM proteoglycans complex, being part lipid, which impede electrical conduction these components are also signaling systems (semiconductors) further normalizing human tissue they significantly counter the lipid prostaglandin's most profound inflammatory mechanism mediator via Component No. 2 while simultaneously and synergistically providing tissue healing and tissue regeneration. Wherein, Component No. 2 also provided for cell membrane regeneration in addition to the healing of cell membrane aided by the glycine amino acid Component of No. 1. While Component No. 1 encompasses the 20 alpha amino acids of the human genetic code provided for tissue protein formation which is so imperative in the healing process.

(The liquid crystal of all these foregoing components of emulsion technology aid in their liquid crystal alignment effects in the healing of diseased tissue as in CD. Exemplified by the chiral liquid crystals Component No. 1 who's living polymerization result in the formation of normal tissue protein in the healing process can be seen to be analogue to the synthesis of synthetic fabrics such as nylon*. These synthetic fabrics are made from liquid crystals that are also synergized by the law of mass action). These liquid crystals polymerize as synthetic fibers. This has been referred to as living polymerization being analogue to protein synthesis in human tissue.

Component No. 2 in a similar robotic like action provides for the production and reproduction of new cell membrane in disease tissue by self vesiculation of PC** (phosphatidyl choline) along with also providing cell membrane focused omega 3 antiprostiglandin Component No. 2 additional potent anti-inflammatory factors. Remarkably and unique to this new drug discovery technology and Q101 KC as the gel hydrate of the colloidal domain Component Nos. 1 and 2 and part of Component No. 3 of emulsion technology with its lipid cell membrane anchor glypicans are similarly effectual in tissue regeneration and healing. These components are dependent mathematically upon calculation and ratio molecular length expressed as I representing molecular length C2 to C6 in Component No. 1 and C16 to C18 in Component No. 2 and volume of this lipid surfactant component expressed as v for volume of this lipid moiety versus this surfactant hydrophilic head group area expressed as ao with a formula Ns the surfactant packing parameter=ao/vl. This may also be expressed as HLB hydrophilic lipophilic ratio. In fact the HLB of all these new medication discoveries may require additional HLB modulation with high HLB surfactants 0.25°/a to ½% to 1% of such as sodium lauryl sulfate or polysorbate 80 (Tween 80) have been found to reduce pathogenic potential. Additionally in correlation again in reduction of pathogenic potential the 3D geometry of the charged particle as measured by X Ray diffraction, NMR (with it's 30,000 molecular weight limitation) may be correlated with polarizing light microscopy and further correlated with histopathologic findings in other successful new product developments as measured by reversal to normal of pathogenicity further correlated with successful in-vitro models computer disease and therapeutic computer response models may also be developed.

The integrated self help synergy of these components can be seen in glycine of Component No. 1 which can also patch a 100 angstrom diseased cell membrane holes correcting these diseased induced lesions. This further illustrates the robotic self assembly* of tissue protein* in the early stages of molecular embryology while awaiting DNA polymerase formation as well as DNA, RNA and Ribosome formation.

Additionally the first stimulant of L-amino acid glycine resulting in the first initiation of protein synthesis occurs in the ovum 15 minutes after fertilization by the sperm (also referred to as the stem cell) through the release of phospholipase A2 resulting in the protein synthesis stimulant lysolecithin formation. Therefore lysolecithin requires the substrate PC** of Component No. 2 phospholipase A2 also may be utilized in the enzymatic portion of Component No. 5. The anti-inflammatory tissue healing non-covalently bonding associated with increase in electrostatic potential particle charge of the colloidal domain all mimicking normal human tissue in structure and function all singularly and synergistically unique to the anti-inflammatory family of medications. The electrostatic potential particle charge is readily measured with zetameter as zetapotential and adds to vital measurements of human tissue vitality.

In CD a disease with genetic predisposition the medical food Q101 KC therapeutic composition comprising Component Nos. 1, 2 and 3 permit the genomic DNA expansion by as much as ⅓rd thereby normalizing the genomic expression. All mediated in directly through the patients own existing DNA. Thereby normalizing and expanding the DNA genomic expression. This concept has been hypothesized and the hypothesis has been based on pre-clinical observations, but not taught in the prior art in the therapeutics of patients as with CD. This genetic response without the direct use of DNA as a therapeutic agent was stressed as a first time patent pending multi center study along with product claims. Further it was noted that patients found to stop Component No. 1 (#2) after 1 month were found to have no CD flare ups for 6 months. Additionally only 30% of these patients had flare ups even though no medication was taken for one year.

Q101 KC is also formulated to reduce mortality risk up to 90% by preventing the greatest CD complication sepsis. CD sepsis is secondary to translocation of the enteric bacterial flora such as $E.$-$coli$. This morbidity and mortality therapeutic effect is coordinated and integrated in Component No. 4 through the administration of Riboflavin B2 50-100 mg in a balanced B 50 complex formulation. Synergistically combining the balanced B complex beneficial effects along with the replacement in CD of poorly absorbed B12 with 500-1000 mcg. Pathophysiology the primary site of B12 absorption is in the ileum. Because of the inflammation the mucosal damage of the ileum B12 absorption is blunted and must be supplemented here.

B2 is an antioxidant and added to antioxidants as 1-2 grams of absorbic acid; 200 to 400 units of vitamin E as d-alpha Tocopherol, 5000 to 10,000 units vitamin A as Beta-carotene, up to 200 mcg of Selenium and Zinc 15 mg as in embodiment case report #3 in therapeutic subject composition Component No. 4.

Another case example of a gentle, side effect free, economic drug discovery derived from this new drug discovery technology and new periodic table. Case #1 is being treated for gout. Patient is intolerant to cyclo-oxygenase Cox 1 anti-inflammatory drugs such as ASA even in small dosages. Intolerant side effects of severe fatigue interfere with daily activity. The patient was also found to be intolerant to Cox 2 inhibitor Bextra 20 mgm unanticipated side effects was pyrosis of almost 1 weeks duration whereas the antioxidant ascorbic acid as 8 grams 16 capsules'/gram each of time release ascorbic acid granules (Carlson Lab, Arlington Heights, Ill.). The time released granules was used avoid similar upper GI symptoms (family history of a bleeding ulcer) this 8 gram course of ascorbic acid was repeated once or twice in 4-8 hrs was associated with complete relief of acute and severe gouty arthritis symptoms (uric acid blood levels of 8-10 g %). Such large dosages of ascorbic acid have been repeatedly reported as harmless.

Thereby this new drug discovery therapeutics for gout was again stored from medical foods and proves to be bio-safe, free of side effects and economically derived. This is in sharp contrast to such highly effective but high risk medications such as Allopurinol with such severe side effects that include a mortality risk. This risk is particularly pertinent in patients such as case#1 with multiple severe drug reactions that threaten vital organs such false lupus drug reactions.

Uric acid is a anti-oxidant that is replaced by the innocuous antioxidant ascorbic acid.

The anti-oxidant ascorbic acid can be synthesized by the animal kingdom where as the anti-oxidant in uric acid is not present in animals helpful comparative biology in drug development.

The bio-science of this new drug discovery as a medical food on first glance Q101 KC appears as 5 building blocks on closer review we instead now see 5 gemstones. Carefully and individually selected, hewn and polished, presented and displayed here as a magnificent therapeutic mosaic converting CD from its formally recalcitrant recurrent clinical presentation as a disease with life threatening flare ups and guarded prognosis. Thereby also countering the interference with activities of daily living e.g. pediatric Crohn's disease, growth retardation and puberty delay all additionally responsive to the therapeutic effects Q101 KC and its components. Expanding the Clinical Application Efficacy of Subject Composition Crohn's Disease Therapy to the Major Intestinal Diseases.

Expanding the clinical application efficacy of subject composition Crohn's disease therapy to the major intestinal disease extensive clinical research has been carried out. This research was based on 5 component subject composition therapy of Crohn's Disease and Pharmaco-dynamic rationale further details (enclosed in several embodiments). To broaden comparative clinical applicability of this research, similar research was performed regarding the following most common intestinal diseases:

Diverticulitis: a very common disease in the elderly affecting ⅓ of people in their 60's and more than ½ of people in their 80's. Irritable Bowel Syndrome. The Inflammatory Bowel diseases: Crohn's Disease and Ulcerative Colitis affects 1 million people. Bowel Cancer is a common complication of Ulcerative Colitis. Bowel Cancer and Cancer were also included is this comparative disease review. This review includes 14 to 25 nutritional components. Statistically significant observation was made in this review of medical foods nutritional components in the essential category.

Therapeutic Component No. 4 Balanced B50 with 50 mgm each of: Thiamine, Riboflavin, Folic Acid 400 mcg, vitamin B12 50 mcg, Biotin 50 mcg was listed 5 of 6× (balanced B Complex also stressing here folic acids and vitamin B12).

Therapeutic Component No. 5 was listed 4 of 6× (a clinical first requirement in Crohn's Disease based on my further clinical experience also in this nutritional medical foods overview.

Therapeutic Component Nos. 2 and 3 of 5 were classified essential.

The prior art has not distilled a final therapeutic composition of 3 or 5 components. The use of these components synergistically praticalizes and maximizes medical food compliance in this therapeutic composition All 5 were listed across the board if the desirable or helpful categories were added with 1 single component omission in Diverticulitis and Crohn's of therapeutic Component No. 3. These 2 diseases with the absence of therapeutic Component No. 3 indicates that these 3 or 5 therapeutic subject composition components embodiments are not in the prior art.

Therapeutic Component No. 4 listed in Bowel Cancer with pre-clinical dose related protection in Bowel Cancer, ascribed primarily to folic acid 400 mcg in cancer. Clinically cancer prevention the folic acid maybe further synergized with the added protection of balanced B complex. All these B complex components are 50 to 100 mgm Thiamine, Riboflavin, Niacin, B6, Pantothenic Acid, Folic Acid 400-800 mcg, B12 12.5-25 mcg and Biotin 50-100 mcg. This anti-cancer treatment increased folic acid 2-3 fold.

The balanced formulation prevents an increase in 1 or 2 of vitamin B-Complex components such as B6, folic acid or B12* from resulting in a paradoxical reduction of other B-Complex members such as B2 Riboflavin which is also an antioxidant.

Coenzymes involved primarily in mediating and providing activation of turning on the metabolic ignition switch" of the amino acids as in therapeutic Component No. 1 and the metabolism of these amino acids and or nucleotides. These cofactors include: 1. Pyridoxal phosphate, the cofactor for transamination and many other reactions of amino acid metabolism, 2. Folic acid contains the amino acid glutamine (as in Component No. 1) and may contain multiple glutamate residues as in triglutamate as in pteroyl gamma triglutamate, coenzymes which transfer single-carbon functional groups in synthesizing nucleotides and certain amino acids. 3. The B12 or cobalamin, coenzymes which participate in the synthesis of methionine in-vivo. Therefore it is not unexpected in the treatment of Crohn's Disease there factors take therapeutic pre-eminence.

Therapeutic rationale the inflamed ileum of Crohn's Disease (the normal site of B12 absorption is the ileum) In ileitis because of the inflamed ileum this vitamin B12 absorption is blunted. Therefore, 500-1000 mgm of B12 should be here prescribed. In the case report embodiment oral administration concurrent with IN. antibiotics for *E. coli* sepsis this balance B complex therapy was used. The use was prompted by the findings of a inflamed magenta red tongue which resulted from the large IV antibiotic dosage required for *E. coli* sepsis which suppressed the symbiotic bowel flora. It was noticed clinically within 1 hour of the use of the balanced B complex the severe weakness from sepsis and the post-operative state greatly improved clinically. This treatment was maintained for more than 6 weeks post operatively. The glossitis promptly cleared. A correlation was found in pre-clinical animal data of decreased mortality by 90% with use of IV Riboflavin B2 in these *E. coli* sepsis mice. This was reported in the Japanese literature in March 2004. This balance B2 treatment fits well in the treatment of colitis and enteritis (small bowel) as a group where disease changes of mucosa can bring on increased morbidity and mortality risks due to translocation of bacteria such as *E. coli* with resulting sepsis.

Also as we inspect the formula of folic acid we find a similar but less extensive polymer of a highly hydrophilic amino acid with HLB of 15 to 16 in L-glutamine coupled with lipophilic pteridine nucleus similar to pyridine and lipophilic PABA-para-amino benzoic acid. In this regard folic acid is analog to Tween 80 HLB 16 in vitro to normalized in vitro breast cancer tissue functioning as an anti-cancer therapy. Using clinically 5×s the concentration of P.C. with HLB 10 to 11 efficacy of Tween 80 0.25% was achieved. This 1.2% P.C. was used in conjunction with essential lipids as 20% soy bean oil. 500 cc of this formulation was used IN. daily ×5 for 5 days in cancer patient care. Excellent clinical response was achieved with such mild measures in cancer with a very poor outlook (squamous cell cancer of the tonsil). This is a very encouraging result in a disease so resistant to the most high risk chemotherapeutic and radiation measures.

Cardiovascular application of therapeutic Component No. 2 Omega 3 fish oil, essential fatty acid fats provides a natural statin effect with its significant anti-inflammatory activity so important in countering atherosclerosis. This is exemplified in other embodiments. Also clinically demonstrated by a 30% reduction in blood cholesterol levels in a 60 year old male. This patient responded to Omega 3 fish oil EPA 350 mg and DHA 250 mg of a total of 750 mg of fish oil Omega 3 phospholipids in a 2 gram capsular dosage (Carlson Lab, Arlington Heights, Ill.) whose blood cholesterol was 150°/a mg pretreatment. This was reduced to 110 mgm % without any risk of muscle weakness as with statins, with further added advantage of prevention of fatal arthythemia (dysrhythmia) as documented by Leaf pre-clinically J. Clinical Nutrition 2003.

Neurologic application The P.S. (phosphatidylserine) is the neurologic equivalent of P.C. (phosphatidylcholine) therapeutic Component No. 2 P.S. 100-300 mgm TID and P.C. in lecithin or purified P.C. 0.9 g or 45% powered lecithin (both American Lecithin products, Oxford Conn.) with 1 to 2 grams TID coupled with Omega 3 essential fatty acid fats both EPA and DHA 2 grams BID as 2 capsules 2× daily derived from northern salmon from deep cold waters of Norway salmon as used above as statin equivalent. This subject composition stain equivalent is analog to statins. As statins have anti-inflammatory effects as ASA, they therefore have been shown to have significant ant Alzheimer effect. Therefore, the scientific rationale for using all the foregoing three components (or optionally P.S. and Omega 3 essential fatty acid) of therapeutic Component No. 2 as anti-Alzheimer therapy. Such protein molecule normalization such as high HLB Tween 80 in prior embodiments may be utilized the abnormal beta sheet amyloid protein (in contrast to the normal neural alpha helix random coil protein) of Alzheimer's and join the foregoing components as synergistic anti-Alzheimer's Therapy. Therefore this therapeutic regime must be considered in countering suspected contributory or causative factors of Alzheimer's disease. As well as Parkinson's disease, mad cow disease and its human equivalent and ALS.

The balance B complex and particularly folic acid and B6 and 1312 also as the amino acids of Component No. 1 cofactors provide coenzyme N metabolism. Also these B vitamin coenzymes also function as chelation agent as the non D-amino acids Component No. 1. Component Nos. 1 and (1 & 2) as in Neocate 10 to 25 grams non D-amino acids of genetic code such as human tissue such as stem cell such as Neocate infant formulas SHS North America, Liverpool, UK (#1&2) serving as a synthetic stem cell subject composition. Also serving as chelating regarding potential suspected toxic metals as aluminum and or mercury. Therefore, a therapeutic rationale for inclusion as in anti-Alzheimer management joining the foregoing 2 or 3 components of therapeutic Component No. 2.

These Nitrogen metabolism coenzymes are also surfactant particularly the L-glutamine of the folic acid residue is analog to the hydrophilic HLB 16 of Tween 80. Also hydrophilic HLB Tween 80 analog to polymerized glutamine of the triglutimate folic acid residue suggestive of an HLB of about 15 to 16. This HLB can be more persistently determined by the use of DuNuoys tensionmeter and the HLB can thereby be calculated. P.C. contain phosphocholine has an HLB of 10-11 is also hydrophilic (being above 7 to 8) with phosphocholine serving as an analog surfactant component of B6 pyridoxal phosphate. The therapeutic rationale for these surfactant components serving as a anti-cancer mechanism.

Additional New Drug Discovery Principles

Histopathologic changes with pathologic stains such H & E (hematoxylin and eosin) identification are highly dependant on the HLB index. Exemplified by lipophilicity H staining the hydrophobic nucleus, and eosin staining the hydrophilic cytoplasm. Therefore these staining HLB characteristics serve as the histopathologic guide to the foci of new drug discovery. Wherein therapeutic Component No. 1 is applicable to tissue protein healing and anti-inflammatory effects with Component No. 1 glycine patching cell membrane disease damage as great as 100 Angstrom units. Therapeutic Component No. 2 heals cell membrane as P.C. (self vesiculating robotic cell membrane formation) with therapeutic HLB flexibility. Component No. 3 ECM extra cellular matrix therapeutic to ECM with anti-neo angiogenetic, anti-inflammatory, anti cancer, and therapeutic activity. Therapeutic Component No. 4 normalizes N metabolism of protein and DNA. Therapeutic Component No. 5 normalizes cell surface disease such as but not limited to such broad applicability to the intestinal diseases and associated intestinal mucosal surface damage as illustrated in foregoing embodiments.

To maximize hydration in this colloidal domain and emulsion technology domain it is recommended that 6 to 8 glasses of water be consumed daily with the utilization of therapeutic subject compositions.

Using this pathophysiology as the mechanical principles of cell and tissue repair in the management of disease the physician now through these modalities can better provide rationale based therapeutics through subject composition Cellbiochem Stem Cell Repair Kit™, Serial number for Trademark application Ser. No. 76/573,604.

An anabolic composition is also provided, which comprises at least one amino acid, at least one extracellular matrix compound, and at least one surfactant, wherein the concentration of surfactant in the composition is about 1% or greater with respect to the total composition. All percentages disclosed herein refer either to weight to volume (if a liquid composition) or weight to weight (if a solid composition).

Any biocompatible surfactant can be used in the composition. Such surfactants are known to those of skill in the art, and representative examples are included in Table 1 below. In addition to the surfactants listed in Table 1, suitable surfactants for use in the composition include lipids (for example phospholipids such as phosphatidylcholine, phosphatidylserine, phosphatidylinositol, phosphatidylethanolamine, phosphatidic acid and phosphotidyl glycerol); essential lipids (which can contain linoleic and linolenic acids), DHA, EPA, sphingolipids; sphingomyelin; glycolipids; cerebrosides; gangliosides; cephalin; lipovitellin; glycosphingolipids; and combinations thereof, monoglycerides, diglycerides, lipoproteins; polyglycerol polyricinolate; polysorbate 80; polysorbate 65 and sodium lauryl sulfate; and combinations thereof.

The total amount of surfactant present in the composition can be in an amount of about 1% or greater; for example between about 1.2% and about 20%. Suitable amounts of surfactant in the composition include about 1.2%, about 1.3%, about 1.4%, about 1.5%, about 1.6%, about 1.7%, about 1.8%, about 1.9%, about 2%, about 3%, about 4%, about 5%, about 6%, about 7%, about 7.5%, about 8%, about 9%, about 10%, about 11%, about 12%, about 13%, about 14%, about 15%, about 16%, about 17%, about 18%, about 19%, about 20%. Amounts of surfactant greater than about 20% (e.g., about 25%, about 30%, about 35%, about 40%, about 45% or about 50%) are contemplated.

In some embodiments, the composition can comprise phosphotidylcholine in amounts of about 19% (to mimic human red blood cell membrane), about 10% (to mimic myelin membrane), about 39% (to mimic heart mitochondrial membrane). In some embodiments, the composition can comprise phosphotidylethanolamine in amounts of about 18% (to mimic human red blood cell membrane), about 20% (to mimic myelin membrane) and about 27% (to mimic heart mitochondrial membrane). In some embodiments, the composition can comprise phosphotidylinositol in amounts of about 1% (to mimic human red blood cell membrane), about 1% (to mimic myelin membrane) and about 7% (to mimic heart mitochondrial membrane). In some embodiments, the composition can comprise phosphotidylserine in amounts of about 8% (to mimic human red blood cell membrane), about 8% (to mimic myelin membrane) and about 0.5% (to mimic heart mitochondrial membrane). In some embodiments, the composition can comprise phosphotidylserine in amounts of about 18% (to mimic human red blood cell membrane), about 20% (to mimic myelin membrane) and about 27% (to mimic heart mitochondrial membrane). In some embodiments, the composition can comprise sphingomyelin in amounts of about 17.5% (to mimic human red blood cell membrane), about 8.5% (to mimic myelin membrane) and about 0% (to mimic heart mitochondrial membrane). In some embodiments, the composition can comprise glycolipid in amounts of about 10% (to mimic human red blood cell membrane), about 26% (to mimic myelin membrane) and about 0% (to mimic heart mitochondrial membrane). In some embodiments, the composition can comprise phosphatidic acid in amounts of about 1.5% (to mimic human red blood cell membrane), about 0.5% (to mimic myelin membrane), about 0% (to mimic heart mitochondrial membrane). In some embodiments, the composition can comprise phosphotidylglycerol in amounts of about 0% (to mimic human red blood cell membrane), about 0% (to mimic myelin membrane), about 0% (to mimic heart mitochondrial membrane). In contrast, the *E. coli* cell membrane has 0% phosphotidylcholine, 0% phosphotidylinositol, 0% phosphotidylserine, 0% sphingomyelin, 0% glycolipid, 0% phosphatidic acid, 18% phosphotidylglycerol and 65% phosphotidylethanolamine.

The at least one surfactant in the composition can have hydrophilic/lipophilic balance ("HLB") of less than about six (e.g., about 1, about 2, about 3, about 4, about 5), or an HLB of about six or greater (e.g., about 7, about 8, about 9, about 10, about 11, about 12, about 13, about 14, about 15, about 16, about 17, about 18, about 19 or about 20). In one embodiment, the surfactant has an HLB value of about 13.

TABLE 1

Exemplary Surfactants

| Name | MFR.* | Chemical Designation | Type† | HLB†† |
|---|---|---|---|---|
| Span 85 | 1 | Sorbitan trioleate | N | 1.8 |
| Arlacel 85 | 1 | Sorbitan trioleate | N | 1.8 |
| Atlas G-1706 | 1 | Polyoxyethylene sorbitol beeswax derivative | N | 2 |
| Span 85 | 1 | Sorbitan tristearate | N | 2.1 |
| Arlacel 65 | 1 | Sorbitan tristearate | N | 2.1 |
| Atlas G-1050 | 1 | Polyoxyethylene sorbitol hexastearate | N | 2.6 |
| Emcol EO-50 | 2 | Ethylene glycol fatty acid ester | N | 2.7 |
| Emcol ES-50 | 2 | Ethylene glycol fatty acid ester | N | 2.7 |
| Atlas G-1704 | 1 | Polyoxyethylene sorbitol beeswax derivative | N | 3 |
| Emcol PO-50 | 2 | Propylene glycol fatty acid ester | N | 3.4 |
| Atlas G-922 | 1 | Propylene glycol monostearate | N | 3.4 |
| "Pure" | 6 | Propylene glycol monostearate | N | 3.4 |
| Atlas G-2158 | 1 | Propylene glycol monostearate | N | 3.4 |
| Emcol PS-50 | 2 | Propylene glycol fatty acid ester | N | 3.4 |

TABLE 1-continued

Exemplary Surfactants

| Name | MFR.* | Chemical Designation | Type† | HLB†† |
|---|---|---|---|---|
| Emcol EL-50 | 2 | Ethylene glycol fatty acid ester | N | 3.6 |
| Emcol PP-50 | 2 | Propylene glycol fatty acid ester | N | 3.7 |
| Arlacel C | 1 | Sorbitan sesquioleate | N | 3.7 |
| Arlacel 83 | 1 | Sorbitan sesquioleate | N | 3.7 |
| Atlas G-2859 | 1 | Polyoxyethylene sorbitol 4.5 oleate | N | 3.7 |
| Atmul 67 | 1 | Glycerol monostearate | N | 3.8 |
| Atmul 84 | 1 | Glycerol monostearate | N | 3.8 |
| Tegin 515 | 5 | Glycerol monostearate | N | 3.8 |
| Aldo 33 | 4 | Glycerol monostearate | N | 3.8 |
| "Pure" | 6 | Glycerol monostearate | N | 3.8 |
| Atlas G-1727 | 1 | Polyoxyethylene sorbitol beeswax derivative | N | 4 |
| Emcol PM-50 | 2 | Propylene glycol fatty acid ester | N | 4.1 |
| Span 80 | 1 | Sorbitan monooleate | N | 4.3 |
| Arlacel 80 | 1 | Sorbitan monooleate | N | 4.3 |
| Atlas G-917 | 1 | Propylene glycol monolaurate | N | 4.5 |
| Atlas G-3851 | 1 | Propylene glycol monolaurate | N | 4.5 |
| Emcol PL-50 | 2 | Propylene glycol fatty acid ester | N | 4.5 |
| Span 60 | 1 | Sorbitan monostearate | N | 4.7 |
| Arlacel 60 | 1 | Sorbitan monostearate | N | 4.7 |
| Atlas G-2139 | 1 | Diethylene glycol monooleate | N | 4.7 |
| Emcol DO-50 | 2 | Diethylene glycol fatty acid ester | N | 4.7 |
| Atlas G-2146 | 1 | Diethylene glycol monostearate | N | 4.7 |
| Emcol DS-50 | 2 | Diethylene glycol fatty acid ester | N | 4.7 |
| Atlas G-1702 | 1 | Polyoxyethylene sorbitol beeswax derivative | N | 5 |
| Emcol DP-50 | 2 | Diethylene glycol fatty acid ester | N | 5.1 |
| Aldo 28 | 4 | Glycerol monostearate (self-emulsifying) | A | 5.5 |
| Tegin | 5 | Glycerol monostearate (self-emulsifying) | A | 5.5 |
| Emcol DM-50 | 2 | Diethylene glycol fatty acid ester | N | 5.6 |
| Atlas G-1725 | 1 | Polyoxyethylene sorbitol beeswax derivative | N | 6 |
| Atlas G-2124 | 1 | Diethylene glycol monolaurate (soap free) | N | 6.1 |
| Emcol DL-50 | 2 | Diethylene glycol fatty acid ester | N | 6.1 |
| Glaurin | 4 | Diethylene glycol monolaurate (soap free) | N | 6.5 |
| Span 40 | 1 | Sorbitan monopalmitate | N | 6.7 |
| Arlacel 40 | 1 | Sorbitan monopalmitate | N | 6.7 |
| Atlas G-2242 | 1 | Polyoxyethylene dioleate | N | 7.5 |
| Atlas G-2147 | 1 | Tetraethylene glycol monostearate | N | 7.7 |
| Atlas G-2140 | 1 | Tetraethylene glycol monooleate | N | 7.7 |
| Atlas G-2800 | 1 | Polyoxypropylene mannitol dioleate | N | 8 |
| Atlas G-1493 | 1 | Polyoxyethylene sorbitol lanolin oleate derivative | N | 8 |
| Atlas G-1425 | 1 | Polyoxyethylene sorbitol lanolin derivative | N | 8 |
| Atlas G-3608 | 1 | Polyoxypropylene stearate | N | 8 |
| Span 20 | 1 | Sorbitan monolaurate | N | 8.6 |
| Arlacel 20 | 1 | Sorbitan monolaurate | N | 8.6 |
| Emulphor VN-430 | 3 | Polyoxyethylene fatty acid | N | 9 |
| Atlas G-1734 | 1 | Polyoxyethylene sorbitol beeswax derivative | N | 9 |
| Atlas G-2111 | 1 | Polyoxyethylene oxypropylene oleate | N | 9 |
| Atlas G-2125 | 1 | Tetraethylene glycol monolaurate | N | 9.4 |
| Brij 30 | 1 | Polyoxyethylene lauryl ether | N | 9.5 |
| Tween 61 | 1 | Polyoxyethylene sorbitan monostearate | N | 9.6 |
| Atlas G-2154 | 1 | Hexaethylene glycol monostearate | N | 9.6 |
| Tween 81 | 1 | Polyoxyethylene sorbitan monooleate | N | 10.0 |
| Atlas G-1218 | 1 | Polyoxyethylene esters of mixed fatty and resin acids | N | 10.2 |
| Atlas G-3806 | 1 | Polyoxyethylene cetyl ether | N | 10.3 |
| Tween 65 | 1 | Polyoxyethylene sorbitan tristearate | N | 10.5 |
| Atlas G-3705 | 1 | Polyoxyethylene lauryl ether | N | 10.8 |

TABLE 1-continued

Exemplary Surfactants

| Name | MFR.* | Chemical Designation | Type† | HLB†† |
|---|---|---|---|---|
| Tween 85 | 1 | Polyoxyethylene sorbitan trioleate | N | 11 |
| Atlas G-2116 | 1 | Polyoxyethylene oxypropylene oleate | N | 11 |
| Atlas G-1790 | 1 | Polyoxyethylene lanolin derivative | N | 11 |
| Atlas G-2142 | 1 | Polyoxyethylene monooleate | N | 11.1 |
| Myrj 45 | 1 | Polyoxyethylene monostearate | N | 11.1 |
| Atlas G-2141 | 1 | Polyoxyethylene monooleate | N | 11.4 |
| P.E.G. 400 monooleate | 6 | Polyoxyethylene monooleate | N | 11.4 |
| P.E.G. 400 monooleate | 7 | Polyoxyethylene monooleate | N | 11.4 |
| Atlas G-2076 | 1 | Polyoxyethylene monopalmitate | N | 11.6 |
| S-541 | 4 | Polyoxyethylene monostearate | N | 11.6 |
| P.E.G. 400 monostearate | 6 | Polyoxyethylene monostearate | N | 11.6 |
| P.E.G. 400 monostearate | 7 | Polyoxyethylene monostearate | N | 11.6 |
| Atlas G-3300 | 1 | Alkyl aryl sultanate | A | 11.7 |
|  |  | Triethanolamine oleate | A | 12 |
| Atlas G-2127 | 1 | Polyoxyethylene monolaurate | N | 12.8 |
| Igepal CA-630 | 3 | Polyoxyethylene alkyl phenol | N | 12.8 |
| Atlas G-1431 | 1 | Polyoxyethylene sorbitol lanolin derivative | N | 13 |
| Atlas G-1690 | 1 | Polyoxyethylene alkyl aryl ether | N | 13 |
| S-307 | 4 | Polyoxyethylene monolaurate | N | 13.1 |
| P.E.G. 400 monolaurate | 6 | Polyoxyethylene monolaurate | N | 13.1 |
| Atlas G-2133 | 1 | Polyoxyethylene lauryl ether | N | 13.1 |
| Atlas G-1794 | 1 | Polyoxyethylene castor oil | N | 13.3 |
| Emulphor EL-719 | 3 | Polyoxyethylene vegetable oil | N | 13.3 |
| Tween 21 | 1 | Polyoxyethylene sorbitan monolaurate | N | 13.3 |
| Renex 20 | 1 | Polyoxyethylene esters of mixed fatty and resin acids | N | 13.5 |
| Atlas G-1441 | 1 | Polyoxyethylene sorbitol lanolin derivative | N | 14 |
| Atlas G-7596J | 1 | Polyoxyethylene sorbitan monolaurate | N | 14.9 |
| Tween 60 | 1 | Polyoxyethylene sorbitan monostearate | N | 14.9 |
| Tween 80 | 1 | Polyoxyethylene sorbitan monooleate | N | 15 |
| Myrj 49 | 1 | Polyoxyethylene monostearate | N | 15.0 |
| Atlas G-2144 | 1 | Polyoxyethylene monooleate | N | 15.1 |
| Atlas G-3915 | 1 | Polyoxyethylene oleyl ether | N | 15.3 |
| Atlas G-3720 | 1 | Polyoxyethylene stearyl alcohol | N | 15.3 |
| Atlas G-3920 | 1 | Polyoxyethylene oleyl alcohol | N | 15.4 |
| Emulphor ON-870 | 3 | Polyoxyethylene fatty alcohol | N | 15.4 |
| Atlas G-2079 | 1 | Polyoxyethylene glycol monopalmitate | N | 15.5 |
| Tween 40 | 1 | Polyoxyethylene sorbitan monopalmitate | N | 15.6 |
| Atlas G-3820 | 1 | Polyoxyethylene cetyl alcohol | N | 15.7 |
| Atlas G-2162 | 1 | Polyoxyethylene oxypropylene stearate | N | 15.7 |
| Atlas G-1471 | 1 | Polyoxyethylene sorbitol lanolin derivative | N | 16 |
| Myrj 51 | 1 | Polyoxyethylene monostearate | N | 16.0 |
| Atlas G-7596P | 1 | Polyoxyethylene sorbitan monolaurate | N | 16.3 |
| Atlas G-2129 | 1 | Polyoxyethylene monolaurate | N | 16.3 |
| Atlas G-3930 | 1 | Polyoxyethylene oleyl ether | N | 16.6 |
| Tween 20 | 1 | Polyoxyethylene sorbitan Monolaurate | N | 16.7 |
| Brij 35 | 1 | Polyoxyethylene lauryl ether | N | 16.9 |
| Myrj 52 | 1 | Polyoxyethylene monostearate | N | 16.9 |
| Myrj 53 | 1 | Polyoxyethylene monostearate | N | 17.9 |
|  |  | Sodium oleate | A | 18 |
| Atlas G-2159 | 1 | Polyoxyethylene monostearate | N | 18.8 |
|  |  | Potassium oleate | A | 20 |
| Atlas G-263 | 1 | N-cetyl N-ethyl morpholinium ethosulfate | C | 25-30 |
|  |  | Pure sodium lauryl sulfate | A | App. 40 |

*1 = Atlas Powder Company, 2 = Emulsol Corporation, 3 = General Aniline & Film Corporation, 4 = Glyco Products Company, Inc., 5 = Goldschmidt Chemical Corporation, 6 = Kessler Chemical Company, Inc., 7 = W.C. Hardesty Company, Inc.
†A = Anionic, C = Cationic, N = Nonionic.
††HLB values, either calculated or determined, believed to be correct to ±1.

The composition can comprise one or more other components, such as amino acids; extracellular matrix components; electrolytes, minerals, vitamins or trace elements; and probiotics. In some embodiments, the composition can further comprise vitelloprotein.

Any amino acid or combination of amino acids can be used in the composition. For example, the 20 naturally-occurring L amino acids (and glycine, which has no stereospecificity) can be used, as the L-stereoisomer is what the mammalian body naturally makes and uses. The L amino acids can be optically pure form. "Optically pure" as used herein means having at least about 90% by weight of one stereoisomer and about 10% by weight or less of one or more other stereoisomers. For example, the L amino acids can be at least about 95% by weight of the L isomer and about 5% by weight or less of the D isomer, such as greater than about 99% by weight of the L isomer and about 1% or less by weight of the D isomer. Optically pure L amino acids are commercially available and are preferred, and also are readily obtainable by methods known to those of skill in the art, for example, by synthesis from an optically pure intermediate.

The amino acids used in the composition can comprise one or more essential amino acids. As used herein, "essential amino acids" are those amino acids that must be supplied in the diet because an organism cannot synthesize sufficient quantities of them. Essential amino acids for adult humans are arginine, histidine, isoleucine, leucine, lysine, methionine, threonine, tryptophan, and valine. Essential amino acids for other groups of human patients or other organisms are known to those of skill in the art.

The amino acids used in the composition can comprise one or more free amino acids, or can be supplied as part of a peptide or protein. As used herein, "free amino acids" are those amino acids that are not part of a peptide or a protein. Free amino acids can be in acid or salt form.

Amino acids for use in the composition can be derived from natural sources or can be synthetically produced. Suppliers of suitable amino acids include Ajinomoto USA of Torrance, Calif. and Tanabe USA Inc. of San Diego, Calif. One exemplary source of amino acids is Neocate® elemental diet, sold by SHS of Liverpool, UK, which contains inter alia essential and non-essential amino acids, dried glucose syrup, fat, minerals, trace elements and vitamins.

The amount of amino acid(s) comprising the compositions can be those daily amounts recommended as an elemental diet for infants or others suffering from gastrointestinal problems. For example, the total amino acid amount in the compositions can be less than about 20 grams, such as about 15 grams or about 10 grams. A suitable amount of amino acid(s) in the composition can comprise 1-2 grams amino acids administered as part of the composition three to four times daily, for a total amount of three to eight grams daily.

Greater or lesser amounts of amino acids in the composition are contemplated, for example about 0.5 to about 0.9 grams daily.

Other suitable amino amounts comprising the composition can be within the following weight ranges, for daily administration:

L alanine: about 0.5 to about 12.5 grams, for example about 5 to about 9 grams.

L arginine: about 0.05 to about 12.5 grams, for example about 1 to about 9 grams.

L asparagine: about 0.05 to about 12.5 grams, for example about 0.5 to about 9 grams.

L aspartic acid: about 0.05 to about 6 grams, for example about 0.5 to about 6 grams.

L cysteine: about 0.1 to about 1 gram, for example about 0.5 to about 1 gram.

L cystine: about 0.5 to about 12.5 grams, for example about 0.5 to about 9 grams.

L glutamine: about 0.5 to about 12.5 grams, for example about 0.5 to about 9 grams.

L glutamic acid: about 0.5 to about 6 grams.

Glycine: about 0.5 to about 12.5 grams, for example about 0.5 to about 9 grams.

L histidine: about 0.5 to about 12.5 grams, for example about 0.5 to about 9 grams. L isoleucine: about 0.5 to about 12.5 grams, for example about 1 to about 9 grams.

L leucine: about 0.5 to about 12.5 grams, for example about 0.5 to about 5 grams.

L lysine: about 0.5 to about 12.5 grams, for example about 0.5 to about 9 grams.

L methionine: about 0.5 to about 12.5 grams, for example about 0.5 to about 9 grams.

L phenylalanine: about 0.5 to about 12.5 grams, for example about 0.5 to about 9 grams.

L proline: about 0.5 to about 12.5 grams, for example about 1 to about 9 grams.

L serine: about 0.5 to about 6 grams.

L threonine: about 0.5 to about 12.5 grams, for example about 0.5 to about 9 grams.

L tryptophan: about 0.5 to about 6 grams.

L tyrosine: about 0.5 to about 12.5 grams, for example about 0.5 to about 9 grams. L valine: about 0.5 to about 5 grams, for example about 0.5 to about 3 grams.

L taurine: about 0.5 to about 12.5 grams, for example about 0.5 to about 9 grams.

L carnitine: about 0.5 to about 12.5 grams, for example about 0.5 to about 9 grams.

The composition can also comprise one or more essential lipids in addition to the surfactants discussed above. As used herein, "essential lipids" are those lipids that must be supplied in the diet because an organism cannot synthesize them in sufficient quantities. For mammals, the essential lipids include linoleic and linolenic acids. Essential lipids for use in the composition can be obtained, for example, from flaxseed, soy, safflower or sesame oils.

The composition can also comprise one or more extracellular matrix components. Suitable extracellular matrix components include glucosamines, glycosaminoglycans, collagens, cartilage, chondroitin sulfates, hyaluronic acid, hyaluronan mucopolysaccharides, glycoproteins, and proteoglycans. Where shark cartilage is used, the composition can comprise about 700 mg to about 2500 mg, for example about 740 to about 1480 mg, administered 1, 2, 3, 4 or 5 times daily as part of the total composition. Shark cartilage can be obtained in powder form, and typically contains cartilage with 12% chondroitin sulfate and collagen. Suitable shark cartilage is sold under the name of Cartilade from BioTherapies, Inc., Fairfield N.J. Bovine cartilage can also be used, for example that which is available from Phoenix Biologics, Inc. (Vista, Calif.), such as administered in a dose of about 750 mg administered 1, 2, 3, 4 or 5 times daily as part of the total composition. Combinations of the shark and bovine cartilage can be used. When hyaluronic acid and hyaluronan mucopolysaccharides are used, the source may be human umbilical cord tissue.

Other suitable extracellular components include glucosamine, which is believed to be incorporated into the body's mucopolysaccharides, and hyaluronic acid, chondroitin sulfate and nutrient substrate cartilage, available from many animals including cow, pig and chicken. Suitable amounts of glucosamine for use in the composition is about 0.5 grams to about 1 gram, administered 3 times daily as part of the total composition. A suitable amount of chondroitin sulfate is about 250 mg to about 500 mg, for example 390 mg to 490 mg, administered 3 to 4 times daily as part of the total composition.

The composition can also comprise one more probiotics. Suitable probiotics include a plurality of beneficial microorganisms (such as lactobacilli, acidophilus, and other yogurt cultures), enzymes, or combinations thereof. Suitable probiotics also include any substance that promotes the growth of beneficial microorganisms in the composition or subject to which the composition is administered, either alone or in combination with other probiotics.

The composition can also comprise at least one electrolyte, vitamin, mineral or trace element. Suitable electrolytes include sodium, potassium and calcium, and can be present in the composition in a concentration of between about 0.1% and about 50%, including any fractional percentage in intervals of about 0.01%. For example, the electrolyte (in particular, potassium) concentration can be represented as about "A.BC %," where A is any integer selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50; B is any integer selected from 0, 1, 2, 3, 4, 5, 6, 7, 8, or 9; and C is any integer selected from 0, 1, 2, 3, 4, 5, 6, 7, 8 or 9. Greater or lesser amounts of electrolytes for use in the composition are contemplated. Suitable vitamins and minerals include typical adult daily dosages, for example: Vitamin A (about 1000 to about 10,000 IU; Vitamin B1 or thiamine (about 50 mg); Vitamin B2 or riboflavin (about 50 mg); Vitamin B3 as niacin or niacinamide (about 50 to about 500 mg); Vitamin B5 or pantothenic acid (about 50 to about 100 mg); Vitamin B6 or pyridoxine (about 50 m); Vitamin B12 (about 300 to about 1000 mcg); Biotin (about 300 mcg); Choline (about 100 mg); Folic acid (about 800 mcg); Inositol (about 100 mg); Para-aminobenzoic acid (about 50 mg); Vitamin C (about 50 mg to about 3000 mg or more, in multiple daily doses); Bioflavonoids (mixed—about 500 mg); Hesperidin (about 100 mg); Rutin (about 25 mg); Vitamin D (about 400 IU); Vitamin E (about 200 to about 600 IU); Vitamin K (about 100 mcg); Apatite (for example microcrystalline hydroxyapaptite—about 4762 mcg; Chromium (about 150 mcg); Copper (about 3 mg); Iodine (about 225 mcg); Iron (about 18 mg); Magnesium (about 750 to about 1,000 mg); Manganese (about 10 mg); Molybdenum (about 30 mcg); Selenium (about 200 mg); and Zinc (about 50 mg). Greater or lesser amounts of vitamins, minerals or trace elements for use in the composition are contemplated.

Thus, the anabolic composition can comprise a surfactant as described above, which can be combined with one or more of at least one amino acid, at least one extracellular matrix compound, at least one electrolyte, vitamin, mineral or trace element; and at least one probiotic.

The composition can be formulated for oral, topical or parenteral use, for example as pharmaceutical formulations. A pharmaceutical formulation comprises the composition and at least one pharmaceutically acceptable excipient, carrier or additive. Suitable topical formulations include ointments, creams or lotions, eye ointments and eye or ear drops, impregnated dressings and aerosols, and can contain conventional excipients and additives such as preservatives, solvents to assist drug penetration and emollients in ointments and creams. Topical formulations can also comprise physiologically compatible carriers, such as cream or ointment bases and ethanol or oleyl alcohol for lotions. Such carriers can be present as from about 1% up to about 98% of the formulation, for example up to about 80% of the formulation.

Oral formulations can be in the form of a compressed solid or dry powder (for example finely milled powder), which can optionally be mixed with water or other suitable liquid vehicle before use. The biologic availability of an oral formulation can be tested by placing the formulation to a vessel containing water or water and an acidic compound (such as 1-5% HCl or acetic acid) to confirm that the formulation dissolves partially or completely. Partial or complete dissolution indicates good bioavailability. For parenteral administration, fluid formulations can be prepared utilizing the therapeutic formulations of the invention mixed with a sterile, pyrogen-free physiologically acceptable carrier or excipient, such as water or physiological saline.

Colorants, flavorants, viscosity modifiers and other additives commonly used in preparing pharmaceutical or nutritional formulations can also be used, as are known to those of ordinary skill in the art. Formulations of the composition can be readily made by those of ordinary skill in the art using standard techniques, for example as described in Remington's Pharmaceutical Science, 17th ed., Mack Publishing Company, Easton, Pa. (1985), the entire disclosure of which is herein incorporated by reference.

Thus, the composition can be administered by any oral or parenteral route, for example by mouth, intrarectally, intranasally, by inhalation into the lung, intravaginally, intravascularly (by infusion or injection), intrapertioneally, intramuscularly and local administration (such as injection or deposition) in or around the tissue to be treated.

The composition can be used to treat patients suffering from (or suspected to be suffering from) a variety of chronic diseases or conditions. For example, the composition can be administered to a patient suffering from, or suspected to be suffering from cancer. The types of cancer that can be treated include cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia and chronic myelocytic leukemia).

Types of cancers that can be treated with the composition also include cancers having their origin in any organ or tissue of the body, for example, the following organs or tissues, regardless of histologic subtype: breast; tissues of the male and female urogenital system (e.g., ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye (e.g., retinoblastomas).

Types of cancers that can be treated with the composition also include cancers or tumors in any prognostic stage of development, for example as measured by the "Overall Stage Groupings" (also called "Roman Numeral") or the "Tumor, Nodes, and Metastases" (TNM) staging systems. Appropriate prognostic staging systems and stage descriptions for a given cancer are known in the art, for example as described in the National Cancer Institute's "CancerNet" Internet website.

An effective amount of the composition is administered to a patient suffering from (or suspected to be suffering from) cancer. An effective amount is that amount of the composition which inhibits the proliferation of a cancer cell. As used herein, to "inhibit the proliferation of a cancer cell" means to kill a cancer or tumor cell, or permanently or temporarily arrest the growth of the cell. Inhibition of tumor cell proliferation can be inferred if the number of tumor cells in the subject remains constant or decreases after administration of the composition, or cancer cell cycles and the metabolic cycles of associated organelles (such as the mitochondria) are normalized. An inhibition of cancer or tumor cell proliferation can also be inferred if the absolute number of such cells increases, but the rate of tumor growth decreases. The number of cancer cells in a subject's body can be determined by direct measurement, or by estimation from the size of primary or metastatic tumor masses. The size of a tumor mass and extent and location of metastasis can be ascertained, for example, by direct visual observation or by diagnostic imaging methods such as X-ray, magnetic resonance imaging, ultrasound, scintigraphy and PET scan. Such diagnostic imaging methods can be employed with or without contrast agents, as is known in the art. The size of a tumor mass can also be ascertained by physical means, such as palpation of the mass or measurement of the mass with a measuring instrument such as a caliper. Ascertaining the size and location of tumors or metastases can also be used to direct the focal administration of the composition, for example by direct injection to or around the tumor or metastases.

An effective amount of the composition can also comprise that amount which stops the progression of, lessens or reverses any condition or symptom associated with the cancer. For example, an effective amount can comprise an amount of the composition sufficient to stop the progression of, lessen or reverse cachexia and/or anorexia associated with a cancer (see, e.g., Examples 1 and 2 below). Indeed, an in vitro reversal of breast cancer of 76%-83% was observed after one week of intravenous administration of the composition. The prognosis of a patient with head and neck cancer also improved greatly after one week intravenous infusion of the composition. One skilled in the art can readily determine an effective amount of the composition to be administered to a patient, by taking into account factors such as the size and weight of the subject; the extent of the tumor growth or disease penetration; the age, health and sex of the subject; the route of administration; and whether the administration is regional (e.g., local) or systemic.

One skilled in the art can also readily determine an appropriate dosage regimen for administering the composition to a patient. For example, the composition can be administered to the subject once, for example as a single infusion or oral administration. Alternatively, the agent can be administered multiple times, for example once, twice, thrice, four, five or six times daily to a patient for a period of from about three to about twenty-eight days, such as from about seven to about fourteen days. In one dosage regimen, the agent is administered orally or parenterally three to four times weekly (or every other day), for three to six months or for an indefinite time period to maintain therapeutic effects.

The compositions can also be used to help reduce the risks of adverse reactions associated with the use of certain allergenic plasticizers in renal dialysis, and thereby prevent recurrent anaphylaxis in dialysis and ameliorate acute flare-ups. Furthermore, the compositions are useful in reducing the risk of kidney or other organ or tissue transplantation rejections. Asthma may also be treated, as well as ailments of the GI tract such as regional ileitis (Crohn's disease) and other inflammatory bowel diseases, including ulcerative colitis, mucous colitis, and liver disease such as congenital biliary atresia. The composition is particularly useful for treating inflammatory bowel diseases that are resistant to present therapies, and for treating inflammation such as that associated with atherosclerosis (e.g., peripheral vascular disease) and complications of this, which can include threatened limb loss, gangrene, coronary artery disease, myocardial infarction, stroke or cerebral vascular accident. Further diseases that can be treated with the composition include degenerative, congenital and hereditary diseases, such as congenital aneurysm (Berry aneurysm).

The composition can be used also in the treatment of trauma and deforming diseases, such as leprosy, and skin and nerve damage. Bacterial infections, such as drug resistant tuberculosis, chronic fatigue and muscle weakness can also be treated.

Diseases of the endoderm, ectoderm, mesoderm and mesenchymal surfaces can be treated with the composition. For example, diseases of the ectodermal surfaces including skin, hair, nails and teeth are amenable to treatment by the compositions. In particular, eczema, urticaria and psoriasis can be treated. The compositions can also accelerate healing and reduce the risks of corneal graft rejection.

The anabolic compositions can also reduce the effects of aging, for example when the production of digestive enzymes and growth hormone is diminished. The composition can also be used to treat immunopathies such as milk allergies, colitis, and autoimmune diseases.

Furthermore, compositions can be used to treat AIDS patients, for example those on anti-protease drugs. AIDS patients on conventional anti-protease drugs often have extreme hyperlipidemia, with serum triglyceride levels of 3,000 to 6,000 mg %. Thus, the anti-protease medication may need to be reduced or withdrawn to protect the heart and blood vessels from the medication's side-effects, such as coronary artery disease. Administration of the composition to AIDS patients on anti-protease drugs can reduce the hyperlipidemia and minimize the undesirable side effects of the drug. As a result, anti-protease dosages can be lessened while achieving the same therapeutic results.

Metabolic storage diseases, such as glycogen storage diseases lipid storage disorder, and demyelinating diseases (such as multiple sclerosis and Pelizeus-Merzbacher disease) can also be treated with the composition, as well as disorders of the blood-brain barrier and neurological diseases (e.g., rabies) and meningitis. Degenerative neurological diseases such as ALS, pernicious anemia, Alzhiemer's disease, Huntington's chorea, and prion-based diseases such as Kreutzfield-Jacob disease can also be treated with the composition. The composition can be used for preventive treatment of the diseases and conditions discussed herein.

For the diseases discussed above, the patient is administered an effective amount of the composition. An effective amount of the composition can also comprise that amount which stops the progression of, lessens or reverses any condition or symptom associated with the disease. For example, an effective amount can comprise an amount of the composition sufficient to stop the progression of, lessen or reverse inflammation associated with an inflammatory bowel disease. One skilled in the art can readily determine an effective amount of the composition to be administered to a patient, by taking into account factors such as the size and weight of the subject; the extent of disease penetration; the age, health and sex of the subject; the route of administration; and whether the administration is regional (e.g., local) or systemic. Dosage routes and dosage regimens are as described above for treatment of cancer.

Without being bound to any theory, it is thought that the essential components of the composition promote favorable substrate nutrition in vivo as well as in vitro for stem cells to thrive and participate in tissue repair, replacement and regeneration. Such effects may occur in mesodermal and mesenchymal tissue, as well as endodermal surfaces such as the gut lining and respiratory tract.

Furthermore, but without wishing to be bound by any theory, the simultaneous administration of components of the therapeutic formulations is believed to work synergistically to promote tissue healing at higher levels and at a more rapid speed than if the components were administered individually at different times.

Again without wishing to be bound by any theory, it is believed that by administering the therapeutic formulations of the present invention and avoiding or minimizing ingestion of foods containing microorganism metabolites or catabolic products (such as dairy products), the patient's recovery is enhanced because the gastrointestinal tract will only be minimally occupied in proteolysis of exogenous proteins and will still serve its immune-like functions, such as control microorganisms (an antibiotic-like function), elimination of viruses, and aiding in the repair of injured tissue to permit tissue healing through the supply of adequate nutrients.

Alternatively, and again without wishing to be bound by any theory, the composition provides nutrition to non-neoplastic cells of the patient, while depriving neoplastic cells of their primary nutrition source. Thus, the composition is advantageously used to combat the cachexia/anorexia syndrome so often seen in cancer patients.

EXAMPLES

The following examples are used to illustrate preferred embodiments of the invention and are not meant to limit the scope of the invention in any way.

In medicine, the average dosages are determined from a bell-curve. For example, most of the patients might respond to dosages as given. However, the beginning of the bell curve response might be 10% to 50% of these dosages and the end of the bell curve might be 125% to 200% of these dosages. Further results may be augmented by addition of component No. 4 and No. 5 to compositions comprising components Nos. 1-3. In addition, this provision applies to all examples included by reference of Patent Ser. Nos. 60/149,338, 09/639,859, 10/752,298, and 10/765,664.

Example 1

Example of Multi-Center Study

Within three to six weeks of initiation of this treatment using the compositions of the invention approaching 95% of Crohn's disease (CD) and pediatric Crohn's disease (PCD) patients are being studied in double-blind, placebo-controlled multi-center including 35 radiographically tagged inflammatory neutrophile permeability studies as well as the open study are able to discontinue the immune suppression therapy.

Remarkably, the discontinuance is not associated with relapse for a period of at least six months. More than 95% are maintained in the disease-free state for as long as one year. Growth arrest and puberty suppression are overcome within six weeks in more than 20 patients with a predictable efficacy of over 95% in 150 patients (⅓ of 450 being studied, (PCD cases treated exceed 200 patients). Controlled in-vitro tissue culture studies of biopsied Crohn's tissue evidences significant (approaching more than 95%) reduction in inflammatory mediator chemokines relative to controls after 24 hours.

The compositions also avert the need for surgery to address another Crohn's Disease complication (intestinal fistulae) in more than 95% of the cases, and in those cases that require surgery in more than 95% (reduction surgical mortality with use of subject composition).

Also, in medicine the average dosages are determined from a bell-curve. For example, most of the patients might respond to dosages as given. However, the beginning of the bell curve response might be 10% to 50% of these dosages and the end of the bell curve might be 125% to 200% of these dosages.

In medicine, the average dosages are determined from a bell-curve. For example, most of the patients might respond to dosages as given in example 2 (infant and child). However, the beginning of the bell curve response might be 10% to 50% of these dosages and the end of the bell curve might be 125% to 200% of these dosages.

Example 2

Congenital biliary atresia (CBA) is a rare fatal (prior to treatment with this invention) disease without liver transplant, with a U.S. incidence of only 300 cases per year (approximately 1 per 1 million of U.S. population) with symptoms occurring at onset of infancy that include: poor appetite, poor food intake, extreme jaundice, (21 mgm percent bilirubin, with biliary obstruction further confirmed by an abnormal dye excretion study. stools were gray, acholic, lacking normal stool bilirubin color), lassitude, weight loss, failure to thrive, abnormal liver function tests, abnormal liver ultrasound, and abnormal biopsy.

Therapy with the compositions of the invention in a CBA patient using components No. 1 and No. 2 re-established organ function, stimulated tissue healing and tissue protein synthesis concurrent with significant anti-inflammatory activity, clearance of all abnormal liver function, and averted the required for a liver transplant.

Components No. 1 and No. 2 were used and the composition comprised of 20 to 30 grams L-amino acids and glycine in the molar ratio of breast milk suspended in 4 oz. of water. Four to 6 doses administered daily were sufficient to normalize, over a period of 3 months all abnormal liver function studies, abnormal liver ultrasound, abnormal biopsy, as well as reversing symptoms of jaundice, poor appetite, poor food intake, lassitude, weight loss, and failure to thrive, off liver transplant list. The patient was sent home with happy disposition, not crying normal stools, sleeping well and easily burped.

Component No. 3 can also be added in the dosage of 0.5 to 2 grams per day, and optional components No. 4 (¼ to ½ of the dosages as administered in Example 3b) and component No. 5 can (¼ to ½ the dosage as administered in Example 3b) can also be added to compositions of the subject invention.

Example 3

Crohn's Disease, (CD) Case Report, Part (a)

A 71 year old female patient with more than 3 decades of Crohn's disease whose symptoms included diarrhea, constipation, severe bouts of abdominal pain and fever, generalized aching, extreme fatigue, nausea, food and dairy intolerance, increased sedimentation rate, recently had a flare up of the Crohn's disease. Response from 4 mgm of corticosteroid, once daily was unsatisfactory. Corticosteroid dosing was then increased to 4 times daily for acute flare ups.

The patient received a composition comprising 5 to 25 grams of L-amino acids and glycine, lecithin (phospholipid-PC), and extracellular matrix components comprising collagen, proteoglycan aggregate complex of cartilage and chondroitin sulfate (shark cartilage 740 mg. per capsule, 4 capsules twice daily). Symptoms of severe abdominal pain and diarrhea, and the flare-up were cleared within 24 hours. The improvement continued over the next few weeks, and the patient responded to the least amount of corticosteroids (alternating daily dosages of a half a tablet (2 mg) with a full tablet (4 mg) required to prevent flare-ups in the past several decades of management.

This reduction in steroid dosage has also reduced severe unsightly bruising and poor healing of lacerations and associated intolerance of sutures. Her lacerations have been most successfully healed with non-suture steri strips.

The second therapeutic component comprises 2.1 grams of omega 3 seed oil, (flax oil, sunflower oil, sesame seed oil 1.7 grams of omega 6 oil, and 1 gram omega 9 oil (Flora brand) (with the following well tolerated preferred recent substitution of omega 3 fish oil and seed oil for just few weeks: 2 capsules 1-2 times daily, Thera Tears, serving size 2 softgels per serving, containing per 2 capsule Vitamin E (as d-alpha tocopherol concentrate) 100 IU (anti-rancidity antioxidant), Organic Flaxseed Oil 500 mg, EPA (Eicosapentaenoic Acid) (from Fish Oil) 225 mg, and DHA (Docosahexaenoic Acid) (from Fish Oil) 50 mg. The anti-rancidity antioxidant vitamin E present in this capsule prevents the development of catabolic products that are counter to the components of this therapeutic innovation accounting for the tolerance of this fish oil product.

This patient is one of the unusual patients intolerant to fish oil. Patients with ileitis have a deficiency of pancreatic lipase and enteric coated fish oil capsules may be more helpful in overcoming this intolerance. This anti-inflammatory immune modulatory pharmacologic activity is furthered by the addition of vitamin A (5,000 units), 250 ml of vitamin C, 400 ml vitamin E (d alpha tocopherol), selenium (20 mg) and Zinc (15 mg).

It should be noted here that significant progress has been made here and in these foregoing embodiments in masking a major problematic taste of the amino acid component which formerly, in the prior art, brought about the requirement of gastric tube administration and associated hospitalization.

Encapsulation of the medication would eliminate use of the gastric tube by by-passing the problematic taste of the amino acid component. However, for the pediatric or adult patient who can not take capsules, a vegetable flavored juice such as, but not limited to, tomato juice or V8 could be used as a flavored vehicle. One heaping teaspoon (approximately 5 grams) to 5 ounces of juice, was found by a taste panel to thoroughly mask the most objectionable taste of the first component, the amino acid product. This amino acid component includes, but is not limited to, Neocate for Infant use. This Crohn's patient was included in our taste panel in our attempt to improve the palatability of the objectionable amino acid component of subject composition.

Case report: Example 3, part (b) Crohn's disease

Further response to addition of therapeutic components No. 4 and No. 5 (All 5 component therapeutic composition response).

Further progress report and addition of components No. 4 and No. 5 to this patient care added even further to significantly improve her clinical course. The addition of components No. 4 and No. 5 have provided for normalization of enzyme composition secretion of the tissue and the normalization of the micro-organism flora with associated normalization of function of this gastrointestinal Crohn's diseased tissue has made possible for this patient for the first time to further reduce from one tablet of the corticosteroid that this three component therapy has permitted to use ½ tablet of corticosteroid (triamcinalone generic) for the first time in three decades without usual further steroid withdrawal symptoms of arthralgia common in steroid withdrawal as noted repeatedly in this patient in the past unsuccessful attempts of steroid reduction.

The side effects this patient has sustained from long-term corticosteroids has been worsening of osteoporosis documented by two successive bone scans two years apart, recurrent bruising and failure to heal including two threats of the need for skin graft which this subject composition stem cell-like treatment has prevented. Bruising and healing time of skin trauma as well as GI flare ups of diarrhea greatly improved.

Example 4

Countering Wound Healing Impairment with Steroids

The prior embodiments documented the reversal of the need for skin graft in wound treatment of a Crohn's patient (exemplified by adding deficient vitamin A locally to anabolic counter collagenase stimulated by long-term corticosteroids) along with wound healing when zinc, in the form of zinc oxide, was added to composition No. 5.

Example 5

Orthopedic and Anti-Arthritic Subject Composition Therapy—Case Report

A female patient age 48 has been treated for acute degenerative arthritis right hip confirmed by x-ray findings. Acute onset, May of 02 associated with progressive pain limping and requirement of support with a cane temporarily relieved by anti-inflammatory drug Vioxx with x-ray findings of severe inflammatory degenerative arthritis associated with absence of joint space of right hip joint and clinical regression right hip. Joint prosthetic replacement even though only age 48 was recommended by rheumatologist and orthopod. Patient refused surgical care and responded with use of extracellular matrix:

ECM: Glucosamine 750 mg. daily, Shark cartilage 450 mg., Cartilage 50 mg, gelatin, a denatured collagen, porcine origin, 1 to 2 tablespoons in fruit juice.

The addition of an anti-inflammatory immune modulator (omega 3 flax-seed oil, 1000 mg) provided a progressive response with reappearance of the hip joint space on x-ray (severe inflammatory changes had interfered with visualization of any joint space). Since the patient is now pain-free and no longer requires a cane supportive of walking, however still had a mild limp, the completion of the synthetic stem cell first and second component chiral L amino acid and non chiral glycine in the molar ratio of human tissue supportive of the stem cell, along with polar surface active lipid as phospholipid lecithin was suggested in the form of Neocate progressing from 5 grams daily to 15 grams daily to three times daily. It is expected that this additional therapy should significantly add to the therapeutic response progression.

Anti-inflammatory, immune modulatory bio-efficacy, bio-safety and pharmacologic activity is present with all four components of synthetic stem cell therapeutic subject composition.

Example 6

Inactivation of Cat Dander Allergen of Cat, to Lessen Respiratory Allergy Symptomatology after Cat Exposure (with Therapeutic Component No. 2)

High HLB liquid crystalline phase semi-conductor bio-computer used here and its biophysical hydrophilic micellar counterpart with its anti-allergenic subject composition therapeutic embodiments, in vitro basophilic de-granulation measure by histamine release comparing efficacy of treated cat dander in preventing histamine release with untreated cat dander when exposed to serum from cat allergic patients.

Example 7

The Use of High HLB Surfactant in Cancer May be Used Alone or as an Optional Component of Component No. 2

Comparative studies of inactivation of in-vitro cancer using tissue culture techniques with high HLB surfactant, Tween 80 are illustrated in Table 1.

Results of Treating T47D breast cancer tissue cells (Normalized):

TABLE 1

| MTS (Breast cancer Mitochondrial activity Assay) | | | |
|---|---|---|---|
| Culture Time | 24 h | 48 h | % normalization of Breast cancer cells |
| Control | 1.0 | 1.0 | 0% |
| **Tween 80 (0.125%) | 0.48 | 0.24 | 76% |
| PC (0.125%) | 0.92 | 0.98 | |
| Tween 80 + PC (0.125% + 0.12596) | 0.61 | 0.42 | 58% |
| GS-1 (grape seed Extract, 0.5 mg 1-ml | 0.29 | 0.17 | 83% |
| Tween 80 + GS-1 | 0.27 | 0.17 | 83% |
| PC + GS-1 | 0.34 | 0.17 | 83% |

Breast cancer (Comparative histopathologic studies before and after treatment with high HLB Tween 80 surfactant
**Histopathologic studies correlate with a more than 50% reduction of cancer cells seen after 48 hours of treatment with 0.125% Tween 80.

Summary of Cell Inhibition Assays

Development of metastatic cancer involves several steps, usually separated in to initiating and promotional steps.

Initiation involves somatic mutation leading to altered expression of genes controlling DNA synthesis and cell replication. Promotion involves stimulation of the mutated cell to continued division. Subsequent mutations in these altered cells lead to more aggressive replication and invasion of neighboring tissues. In many tumors, the tumor cells are cycling while their neighbors are in the GO phase of the cell cycle. Substances which interfere with mutagenesis or with cell division could prove to be anti-carcinogenic.

Several extracts of these for their abilities to inhibit the metabolism of cells isolated from breast and cervical cancer tissue have been examined in regard to the anti-cancer effects of extracts which have proven capable of significantly inhibiting the metabolism of these cancer tumor cells. In addition to and equal to the effects of high HLB surfactants for comparative testing. These comparative studies were performed and results are reported in the above table. Metabolism was comparatively measured with controls and other extracts as to the reduction of mitochondrial activity, (MTS). This compound is a substrate for the mitochondrial enzymes—and is reduced to a blue formazan product.

Activity of the extracts was tested with the MCF-7 and T47-D breast cancer cell lines and against the CaSki and SiHa cervical cell lines. During the later experiments, the CRL 7367 and CRL 7368 cell lines became available and were included in subsequent trials. CRL 7368 is a line established from transformed fibroblasts isolated from a breast cancer. CRL 7367 was established from apparently healthy skin fibroblasts taken from the same donor.

Methods

In the first experiments—The extracted therapeutic test agents were derived from specified tissue. Water extracts of the crushed tissue, were also prepared. For the later experiments, specific varieties of extracts were prepared and examined: Cells were obtained from American Type Culture Collection (ATCC, Washington, D.C.) and were cultured as recommended by ATCC. Experiments were performed in 96 well microtiter plates. Each well contained $1.0 \times 10^4$ cells suspended in a total volume of 200 ml. Test wells contained the designated amount of extract in cell culture medium. Control wells contained the same amount of extract solvent in medium. Plates were incubated in an atmosphere of 5% $CO_2$ for 24 or 48 hours with extract or solvent. At this time, -pl-(MTS) were added to each well and incubation was continued for an additional 4 hours after which time the optical density (OD) at nm of each well was recorded. In each experiment, each sample was assayed in triplicate and the mean optical density (OD) for the three wells containing the same culture was calculated.

Results

Data are presented as suppression ratios. The suppression ratio defined here as the mean optical density (OD) for the wells containing extract divided by the mean optical density (OD) for the control wells. A value of this ratio of 1.0 indicates that the extract had no effect on metabolism of the cells being tested. A value of less than 1.0 indicates inhibition of cell metabolism by the extract or the high HLB surfactant Tween 80.

The purpose of the work was to determine which therapeutic agent extracts (further separated by chromatography) explored through this methodology for anti-cancer activity. The data presented here represents semi-quantitative anti-cancer screening tests. Extracts with ratios in the range 0.51-0.74 were considered moderately active and therefore appropriate for considered use along with preventive anti-cancer treatment and active anti-cancer treatment. In co-use with anti-cancer treatment and radiation treatment, may lessen the dose and the side effects of these current therapeutic agents. Extracts with metabolism suppression ratios less than or equal to 0.5 represented a suppression of metabolism of at least 50% or greater than that of the controls and were considered definitely active potential anti-cancer agents, as was the case of High HLB Tween 80 with ethylene maturation apoptosis promoting factor with a 76% suppression of mitochondrial metabolism of cancer cells.

In the first experiments, tissue extract prepared in the laboratory and water extract from tissue commercially obtained were, comparatively examined. These results were presented in Table 1. The data indicated that comparatively both therapeutic agents derived from tissue extracts freshly prepared in this laboratory and water extract inhibit can cell metabolism at the higher concentrations tested. There is a clear dose effect indicating that therapeutic agents derived from tissue extracts prepared in our laboratory at concentrations lower than 0.004 and commercially available water extract concentrations lower than 0.02 do not inhibit metabolism. Data for alcohol extracts were also presented. The extracts had minimal effects on metabolism after three days of treatment, but after five days of treatment the ethanol extract had inhibited metabolism of both breast cancer cell lines by over 60%. Some extracts suppressed the MCF-7 cell One, but had minimal effect on the T47-T cell line or on the cervical cancer cell lines even when the extract anti-cancer treatment agent composed 4% of the total culture volume. Of all the extracts examined the tissue extract anti-cancer treatment agent* obtained with 70% acetone/30% water was the most active.

Acetone is an agent used in separating phospholipid surfactants, e.g. phosphatidylcholine (PC), phosphatidyl serine (PS), phosphatidyl inositol (PI), and phosphatidyl ethanolamine (PE) acetone insoluble representing 58% of surfactants present in soy lecithin. 70% acetone and 30% water used here as a tissue extracting agent is most probably an extracted surfactant*.

Example 8

Case Report—Therapeutic Composition to Counter Withdrawal Symptoms and Side Effects of Medications and Drugs and Drug Addiction and Dependency The Therapeutic Results and Rationale for inclusion of Components No. 4 and No. 5: This detailed therapeutic replication of normal human tissue (and therefore complete reversal of disease tissue) and by including the products of therapeutic component Nos. 4 and 5, (added to component Nos. 1, 2, and 3 past month and added past two months to care of prior patient), normalization of enzyme composition secretion of the tissue and the normalization of the microorganism flora with associated normalization of function of this gastrointestinal Crohn's diseased tissue has made possible for this patient for the first time (and not reported or taught in that art) to further reduce from one tablet of the corticosteroid that this three component therapy has permitted to use ½ tablet instead of corticosteroid (triamcinalone, common generic) for the first time in three decades without usual further steroid withdrawal symptoms of arthralgia common in steroid withdrawal as noted repeatedly in this patient in the past unsuccessful attempts of steroid reduction.

The side effects this patient has sustained from long-term corticosteroids has been worsening of osteoporosis documented by two successive bone scans to years apart, recurrent bruising and failure to heal including two threats of the need for skin graft which this subject composition stem cell-like treatment has prevented. Bruising and healing time of skin trauma as well as GI flare ups of diarrhea greatly improved.

These therapeutic compositions may also be specifically applied to addiction by mimicking normal tissue metabolism and normal tissue including the L-amino acid glycine molar ratio of endorphin to metabolically stimulate and in fact coerce, by the law of mass action, the proteins assemblage system of the body to produce this hormone. Since one mole of tyrosine, two moles of glycine and one mole of phenylalanine seem to be essential for the narcotic effects of beta endorphin and the met and leu-enkephalins, this anti-addiction effect then would be compared to the complete L-amino acid glycine molar ratio of beta endorphin. This molar ratio of beta endorphin also includes one mole of methionine, two moles of threonine, two moles of serine, four moles of lysine, two additional moles of phenylalanine, one mole of glutamine, one mold of proline, one mole of valine, one mole of leucine, two moles of asparagine, two moles of alanine, two moles of isoleucine, one mole of tyrosine, one mole of glycine, and one mole of glutamic acid.

The same principles and therapeutic components have been applied in normalizing, as noted in prior embodiments, dependency or withdrawal symptoms such as, but not limited to, the use of drugs in controlled substances, alcohol and/or drug and tobacco addiction in the medical patient or veterinary practice or experimental conditions such as the animal or tissue culture.

Therefore, these therapeutic compositions form a clinical bridge beyond other advanced technologies that have not to date found a clinical application with exemplary bio-safety.

Example 9

Case Report—Treatment of *E. coli* Sepsis

Patient age 77, male, recovered from 10 day hospitalization for surgical intact removal of gangrenous gallbladder and *E. coli* sepsis, Apr. 26, 2004, responded to a total of 16 days IV Azactam 2 grams and Clindamycin 0.9 g, reduced to 0.6 g, q 8 hrs. Balanced B-50 complex, Nature Made, OTC, Mission Hills Calif. 91346-9606.

Ingredients 50 mg of: B-1 Thiamin, B-2 Riboflavin, B-3 Niacin, B-6 Pyrdoxin, Pantothenic Acid, Folic Acid 400 mcg, Biotin 50 mcg.

Administered orally (PO), concurrent with IV antibiotics for *E. coli* sepsis (glossitis, magenta inflamed tongue evidence for B-complex associated with IV antibiotics) prompted the initiation of this medication and within 1 hour of use profound weakness associated with sepsis and post-op state. These beneficial effects were maintained with the continued use of balanced B-complex 2xs daily with Centrum OTC multi-vitamin and mineral compound. This effect correlates with the pre-clinical mouse colony *E. coli* infected animal studies 90% improvement noted in the Japanese literature March, 2004. This clinical effect is novel to the prior art in that it has not been reported in the clinical medical literature to date.

(E.R. admission acute cholecystitis, 20,000 WBC, which increased to 30,000 wbc. Surgery not performed for 2.5 days.) IV antibiotics well tolerated.

Common post-op complication of severe weakness and fatigue significantly lessened with balanced B Complex, including 50 mg Riboflavin (magenta red tongue prior to this treatment).

PHx of multiple lupoid severe antibiotic vital organ reactions inclusive of: pericardial infusion due to Biaxin, Penicillin induced nephritis, albuminuria and one occasion frank hematuria. Lupoid hepatitis, Sulfonamides and anti-fungal Miconozole, Drug fever—Quinolones, Flagyl and Percocet intolerance.

Local combination of antacid and anesthetic gave prompt relief but hindered acute findings of the disease.

Along with this consideration, nitroglycerin dilated the bile ducts in addition to the coronary arteries. Also noteworthy, nitroglycerin gave relief. This clinical correlation with pre-clinical study in mice is highly significant in that mice have been naturally bred to resist squalor and *E coli* exposure.

Example 10

Case Report—Anti-Cancer Therapy

Case Report Part a:

A clinical anticancer bi-lamellar surfactant liquid crystal essential fatty acid emulsion therapeutic study with the additional strategy of "starving" the cancer cell's high carbohydrate based Pet Scan metabolic activity companion to foregoing surfactant liquid crystal high HLB of 16 in vitro anticancer study A 59 year old male patient was treated for an adenocarcinoma of the left parotid gland and responded to surgical excision, chemotherapy and radiation.

Five months later within a 1 to 2 cm. radius of prior adenocarcinoma tumor a left tonsillar squamous cell carcinoma was detected with multiple metastasis to bone, lung and brain, with weight loss and cachexia with a very poor prognosis.

Two dosages of chemotherapy were administered. It was noted that an unexpected dramatic clinical response was noted after "supportive" (which proved to be remarkably definitive), essential fatty acid lipid 20% non pyrogenic soybean oil emulsion, 4-11% linolenic acid, 44-62% linoleic acid, oleic acid 19-30% stearic acid 1.4%-5% (Intralipid 20% Baxter Healthcare Corporation package insert) and 1.2% "egg yolk lecithin phospholipid", 2.25% hydrophilic glycerine, and H20 totaling 500 ml and 900 K Cal daily for 5 days. PC was used here at 5x surfactant concentration of ¼% Tween "80. Thereby equilibrating the lower HLB PC with the high HLB (16) of Tween 80 was successfully used in cancer in vitro (prior embodiment).

HLB is a mathematically additive phenomenon. Tween 80 in-vitro studies reversed and normalized 76% to 83% mitochondrial metabolic activity breast cancer and 50% of the histopathologic in 24 to 48 hours.

Interpreting this dramatic response in light of the normalization of the cancer tissue with foregoing in vitro studies derived from: (1) a similar high HL B surfactant effect with cell membrane egg lecithin phospholipid closer to normal cell membrane of a stem cell (fertilized egg) and (2) closer to mimicking the biochemistry of the stem cell, the primary inventive mimicking analog directive of this series of inventions, (3) and in consideration of and based upon the fact that the PET scan is indicative of an aggressive cancer which has significant for carbohydrate dependent metabolism marker mechanisms.

The use of IV feeding carbohydrate free, hydrophilic surfactant, essential lipid appears to counter the significant PET scan utilization of Intravenous administration of glucose radioactively tagged in the cancer patient. The glucose dependent cancer cell growth and in a sense "starved" these cancer cells, (a strategy that we were searching for). In addition, this lipid ketogenic IV feeding also turned off insulin production, an important molecular stimulus of rapid cell growth and differentiation of cancer tissue. Also without the analog requirement of an electric spark as in a gasoline engine (the opposite of an oil driven diesel engine) the adverse oxidative metabolic predisposition to cancer and inflammation.

While not wishing to be bound to any theory the in-vitro study high HLB surfactant and the intrinsic mitochondrial lipid may have been the coordinated team effect in vitro of normalization of cancer tissue using the foregoing rationale mechanism readily adaptable to oncologic care.

Future in vitro and in vivo studies will be carried out on cancer tissue and cancer patients respectively in a similar fashion adding to the foregoing preclinical and clinical trials 0.25 percent of Tween 80 and 0.15 percent of sodium lauryl sulfate as well as in further contrast in conjunction with 1.2% PC 20% essential lipid to increase the total high HLB efficacy. These studies will be monitored with PET scan.

Case Report Part b:

To further the anticancer effect of anti-inflammatory therapy of aspirin as observed in bowel cancer (50% efficacy) 25% efficacy in breast cancer;

This therapy aspirin 0.30.g to 0.6 g three × daily anti-inflammatory therapy is added to 2a to meet any possible future therapeutic resistance.

This anti-inflammatory aspirin therapy is further compared to the use of anti-inflammatory therapeutic Component No. 2 which includes 2 grams of omega 3 fish oil 350 mg EPA, 250 mg DHA of total 750 omega 3 fatty acid fish oil with antioxidant of 20 units natural vitamin E (d alpha tocopherol) Carlson Arlington Heights, Ill. 60004 and optional inclusion of seed oil, flaxseed oil 250 to 500 mg OTC preferably organic.

High HLB 11 PC 0.9 g American Lecithin, Oxford, Conn. 3× daily

Case Report Part c:

To further advance this anti-cancer effect of therapeutic Component No. 2 as modified in 2a, 2b and further modified in 2b with aspirin to be studied regarding furthering anti-cancer potential by adding sequentially and comparatively Component Nos. 3, 4, and 5. These comparative effects to be studied pre-clinically as a computer model, in vitro animal model and finally in clinical applications in cancer patients, (as a forthcoming NIH planned study to e monitored with a PET scan study.

Note:

This anti-cancer anti-inflammatory therapeutic effect in cancer correlates well with the countless clinical observations that chronic inflammation such as but not limited to ulcerative colitis predisposes to bowel cancer. Asbestosis due to inhalant exposure to asbestos results in pulmonary accumulation of non-metabolizable asbestos bodies which has a cancer inducing incubation period for as long as 20 years with resultant pleural lining cancer of poor prognosis, the mesothelioma.

Example 11

Case Report—Crohn's Disease (CD)

Case Report Part a:

3 Component Therapeutic Subject Composition not in Prior Art

A 71-year-old female patient with more than 3 decades of Crohn's disease whose. symptoms included diarrhea, constipation, severe bouts of abdominal pain and fever, G.I. bleeding generalized aching, extreme fatigue, nausea, food and dairy intolerance, increased sedimentation rate, recently had a flare up of the Crohn's disease. Response from 4 mgm of corticosteroid, once daily was unsatisfactory. Corticosteroid dosing vas then increased to 4 times daily for acute flare ups. Symptoms cleared and permitted 25% decrease in corticosteroid and 80% decrease in corticosteroid that were required for flare ups.

The patient received a composition comprising 5 to 0.25 grams of L-amino acids and glycine, Neocate infant formula in the genetic code and molar ratio of human tissue, (breast milk and stem cell human tissue), lecithin, (phospholipid) P.C. and extracellular matrix components comprising collagen, proteoglycan aggregate complex of cartilage and Component No. 3 chondroitin sulfate (shark cartilage 740 mg. per capsule, 4 capsules twice daily). Symptoms of severe abdominal pain and diarrhea, and the flare-up were cleared within 24 hours. The improvement continued over the next few weeks, and the patient responded to the least amount of corticosteroids. (alternating daily dosages of a half a tablet (2 mg) with a full tablet. (4 mg) required to prevent flare-ups in the past several decades of management.

This reduction in steroid dosage has also reduced severe unsightly bruising and poor healing of lacerations and associated intolerance of sutures. Her lacerations have been most successfully healed with non-suture steri strips.

The second therapeutic component comprises 2.1 grams of omega 3 seed oil, (flax oil, sunflower oil, sesame seed oil 1.7 grams of omega 6 oil, and 1 gram omega 9 oil (Flora brand) (with the following well tolerated preferred recent substitution of omega 3 fish oil and seed oil for just few weeks: 2 capsules 1-2 times daily, Thera Tears, serving size 2 softgels per serving, containing per 2 capsule Vitamin E (as d-alpha tocopherol concentrate) 100 IU (anti-rancidity antioxidant), Organic Flaxseed Oil 500 mg, EPA (Eicosapentaenoic Acid) (from Fish Oil) 225 mg, and DHA (Docosahexaenoic Acid) (from Fish Oil) 50 mg. The anti-rancidity antioxidant vitamin E present in this capsule prevents the development of catabolic products that are counter to the components of this therapeutic innovation accounting for the tolerance of this fish oil product.

This patient is one of the unusual patients intolerant to fish oil with the exception of the foregoing formulation. Patients with ileitis have a deficiency of pancreatic lipase and enteric coated fish oil capsules may be more helpful in overcoming this intolerance. This anti-inflammatory immune modulatory pharmacologic activity is furthered by the addition of vitamin A (5,000 units), 250 mg of vitamin C, 400 units vitamin E (d alpha tocopherol), Selenium (20 mcg) and Zinc (15 mg).

It should be noted here that significant progress has been made here and in these foregoing embodiments in masking a major problematic taste of the amino acid component which formerly, in the prior art, brought about the requirement of gastric tube administration and associated hospitalization. Also the dose of the L-amino acid glycine, in the molar ratio and the genetic code of human tissue formulation, was moderated to 5 to 25 g 3× daily.

Encapsulation of the medication would eliminate use of the gastric tube by by-passing the problematic taste of the amino acid component. However, for the pediatric or adult patient who can not take capsules, a vegetable flavored juice such as, but not limited to, tomato juice or V8 could be used as a flavored vehicle. One heaping teaspoon (approximately 5 grams) to 5 ounces of juice, was found by a taste panel to thoroughly mask the most objectionable taste of the first component, the amino acid product. This amino acid component includes, but is not limited to, Neocate for Infant use. This Crohn's patient was included in our taste panel in our attempt to improve the palatability of the objectionable amino acid component of subject composition.

Case Report 3 Part b—Crohn's Disease Therapeutic Composition:

Further response to addition of therapeutic components No. 4 and No. 5 (All 5 component therapeutic composition response).

Further progress report and addition of components No. 4 and No. 5 to this patient care added even further to significantly improve her clinical course. The addition of components 4 and No. 5 have provided for normalization of enzyme composition secretion of the tissue and the normalization of the micro-organism flora with associated normalization of function of this gastrointestinal Crohn's diseased tissue has made possible for this patient for the first time to further reduce from one tablet of the corticosteroid that this three component therapy has permitted to use ½ tablet of corticosteroid (triamcinalone generic) for the first time in three decades without usual further steroid withdrawal symptoms of arthralgia common in steroid \I withdrawal as noted repeatedly in this patient in the past unsuccessful attempts of steroid reduction. With this 5 component therapeutic composition there was a 50% decrease in daily corticosteroid dosage without any flare up of Crohn's disease symptoms. A significant corticosteroid sparing effect was achieved with this 5 component therapy.

Particularly significant in that the side effects this patient has sustained from long-term corticosteroids has been worsening osteoporosis documented by two successive bone scans two years apart, recurrent bruising and failure to heal including two threats of the need for skin graft which this subject composition stem cell-like treatment has prevented bruising and healing time of skin trauma as well as GI flare ups of diarrhea greatly improved.

The goal of these series of inventions has been achieved in the normalization of diseased tissue synergistically with the addition of gentle bio-safe medical food and medical food (plant and animal) tissue derived as biochemical components.

Each disease group was studied for deficiencies which were corrected as exemplified by component No. 4 and No. 5 to complete the mimicking and analog structure of normal tissue in the normal replication of human tissue normalizing its structure and function in order to bring about the arrest of the vicious cycle of diseases and their pathogenic mechanisms.

Component No. 4:

The 4th component helps to attain this goal by mimicking and being analog to normal human tissue by using these components 1 through 5 synergistically, comprises vitamins, minerals, and trace elements. Utilizing documented deficiencies of vitamins, minerals and trace elements from available studies or performing pilot study guide lines. Exemplary deficiencies in Crohn's disease are documented in the embodiments of the examples presented. Vitamins, minerals and trace elements can be provided in various concentrations:

Vitamin B12 (500 micrograms), Nature Made Nutritional Products, Mission Hills, Calif., 91348

Centrum Silver which includes: vitamin A (as beta-carotene 5,000 units), vitamin D 400 units, Selenium 20 micrograms, Whitehall-Robins Healthcare, Madison, N.J. 07940 (see below for complete list of contents).

| Centrum Silver Supplement Facts | |
|---|---|
| Serving Size 1 Tablet % DV | Each Tablet Contains % DV |
| Vitamin A 5000 U (20% as Beta Carotene | Magnesium 100 mg |
| Vitamin C 60 mg | Zinc 15 mg |
| Vitamin D 400 U | Selenium 20 mcg |
| Vitamin E 45 U | Copper 2 mg |
| Vitamin K 10 mcg | Maganese 2 mg |
| Thiamin 1.5 mg | Chromium 150 mcg |
| Riboflavin 1.7 mg | Molybdenum 75 mcg |
| Niacin 20 mg | Chloride 72 mg |
| Vitamin $B_6$ 3 mg | Potassium 80 mg |
| Folic Acid 400 mcg | Boton 150 mcg |
| Vitamin $B_{12}$ 25 mcg | Nickel 5 mcg |
| Biotin 30 mcg | Silicon 2 mg |
| Pantothenic Acid 10 mg' | Vanadium 10 mcg |
| Calcium 200 mg | Lutein 250 mcg |
| Phosphorus 48 mg | |
| Iodine 150 mg | |

Balanced B 50 Complex, containing Thiamin (50 mg), Riboflavin (50 mg), Niacin (50 mg), Vitamin B6 (50 mg), Folic Acid (400 mcg), Vitamin B12 (50 mcg), Biotin (50 mcg), Panthothanic Acid (50 mg.), Nature Made Nutritional Products, Mission Hills, Calif., 91348

Vitamin C, (500 mg) Timed release capsules, J.R. Carlson Lab. Inc., Arlington Heights, Ill. 60004

Vitamin E, (400 units), D alpha tocopherol, J.R. Carlson Lab. Inc., Arlington Hts. Ill. 60004

Component No. 5:

An extension of treatment of the synthetic stem cell therapy subject composition in the same patient as Ex. 1 with the addition of component No. 4 presented in detail in Ser. No. 09/639,859 and therapeutic component No. 5 enzyme and pro-biotic 0.9 g tablets two tablets daily to three times a day preferably before meals of enzyme replacement and pro-biotic microflora normalizing factor that comprises Phytozyme, #6122, (Life Plus Int'l. Batesville, Ark.), Amylase (50 mg), Bile (45 mg), Bromelain (30 mg), Lipase (25 mg), Pancreatin 6× (NF) (100 mg), Pancrelipase (110 mg), Papain (30 mg), Pepsin (70 mg), Betaine HCl (100 mg), and Probiolic Blend (20 mg) tablet, dosage 2 tablets 2 to 3× daily having the ingredients: Betaine, HCl, Pancrelipase, Pancreatin 6× (NF), Pepsin, Dicalciuim Phosphate, Amylase, Bile, Bromelain, Papain, Lipase, L-Glutaminic Acid, (ProBio Tx), Stabilized Probiotic Blend (each dosage: 200,000,000 probiotic microflora including *Lactobacillus acidophilus* DDS-1, *Bifido-bacterium bifidum, Lactobacillus bulgaricus, Lactobacillus salivarius*), vegetable and fruit concentrates. Deficiencies of pancreatic enzymes are readily available in exampled disease, Crohn's disease, along with cystic fibrosis. Therefore corrected here in the therapeutic component formulations to normalize not only human tissue but its secretions. Reversal to normal flora with probiotic also readily available and, therefore, used here for the same therapeutic rationale of normalization of tissue, its symbiotic surface bacteria and associated secretion contents of enzymes.

In the case of the gastrointestinal tract in diseases such as, but not limited to, Crohn's disease, the addition of enzymatic therapy of component No. 5 and the addition of pancreatic and enzymatic replacement of deficiencies present herein normalizes the gastrointestinal secretion component and byproduct of human tissue. The addition of probiotic microorganism therapy such as, but not limited to, *Saccharomyces boulardii* helps normalize the abnormal microflora that the disease gastrointestinal tract such as but not limited to Crohn's disease predisposes to thereby even further normalizing abnormal microflora (which this vicious cycle chronic granulomatous Crohn's disease has fostered) the gastrointestinal microflora, tissues and secretions.

This detailed therapeutic replication of normal human tissue secretions, deficient in such diseases as Crohn's disease and cystic fibrosis, (and therefore synergizes further complete reversal of disease tissue). By including therapeutic component Nos. 4 and 5 and secretions of the tissue and the normalization of the micro-organism flora with associated normalization of function of this gastrointestinal Crohn's diseased tissue has made possible for this patient for the first time to further reduce from one tablet of the corticosteroid that this three component therapy has permitted to use ½ tablet instead (Triamcinalone, generic) for the first time in three decades. The side effects this patient has sustained from long-term corticosteroids has been worsening of osteoporosis documented by two successive bone scans two years apart, recurrent bruising and failure to heal including two threats of the need for skin graft which this subject composition stem cell-like treatment has prevented.

These favorable conditions make it more and more difficult for the diseased tissue, such as but not limited to chronic granulomatous disease, as in Crohn's disease and thereby reversing the vicious cycle of this disease and other diseases such as but not limited to Crohn's disease. This has proved itself clinically in the embodiment example cited here wherein digestive enzyme formulation containing pancreatic enzyme replacement, (as well to as bile which has also been incriminated as deficient in Crohn's disease) along with pro-biotic micro-organism resulted in flora normalization. The pro-biotic in this case was *Lactobacillus acidophilus, Bifidobacterium bifidum, Lactobacillus bulgaricus, Lactobacillus salivarius* use of in this addition and completion of the normalization therapeutic stem cell-like repair kit formulation.

Most importantly component steps are analogous to a team or corporate approach to the normalization of tissue with anabolic reconstructive reversal of the pathogenesis of a complex vicious cycled catabolic destructive disease further analog to the underlying pathogenetic mechanisms and the basis of the former refractory state of disease. Crohn's disease and many other diseases with such analogous pathogenetic destructive componental mechanisms, associated deficiencies and medication side effects can be treated with the subject composition. Preferably to best address this disease state, all components of synthetic stem cell like subject composition formulations are contained in the molar ratios of human tissue.

Conclusion:

Through the use of medical food derived synergistic components, drug usage with significant side effects have been significantly spared. Such high risk drugs as corticosteriods in Example #3 have been greatly minimized in successful Crohn's Disease management. This goal of eliminating the side effects of 3 decades of systemic corticosteroids is being furthered by the addition of Entocort (budesonide), a primarily a gastrointestinal surface acting corticosteroid whereby 1 to 2 dosages, 3 mgm capsule of Entocort EC will be used daily to further attempt the complete discontinuance of high risk systemic corticosteroids.

Drug efficacy has been maximized and their side effects minimized as in anti-sepsis therapy and as in the anti-cancer therapy discussed supra.

Each disease group was studied for deficiencies which were corrected as exemplified by components No. 4 and No. 5 to complete the mimicking and analog structure of normal tissue in the normal replication of human tissue normalizing its structure and function in order to bring about the arrest of the vicious cycle of diseases and their pathogenic mechanisms.

The goal of these series of inventions has been achieved in the normalization of diseased tissue synergistically with the addition of gentle bio-safe medical food and medical food (plant and animal) tissue derived as biochemical components.

Example 12

Case Report—Treatment of Gout

Another case example of a gentle, side effect free, economic drug discovery derived from this new drug discovery technology and new periodic table. A patient is being treated for gout. Patient is intolerant to cyclo-oxygenase Cox 1 anti-inflammatory drugs such as ASA even in small dosages. Intolerant that side effects of severe fatigue interfere with daily activity. The patient was also found to be intolerant to Cox 2 inhibitor Bextra 20 mgm unanticipated side effects was pyrosis of almost 1 weeks duration whereas the anti-oxidant ascorbic acid as 8 grams 16 capsules'/gram each of time release ascorbic acid granules (Carlson Lab, Arlington Heights, Ill.). The time released granules was used avoid similar upper GI symptoms (family history of a bleeding ulcer) this 8 gram course of ascorbic acid was repeated once or twice in 4-8 hrs was associated with complete relief of acute and severe gouty arthritis symptoms (uric acid blood levels of 8-10 g %). Such large dosages of ascorbic acid have been repeatedly reported as harmless.

Thereby this new drug discovery therapeutics for gout was again stored from medical foods and proves to be bio-safe, free of side effects and economically derived. This is in sharp contrast to such highly effective but high risk medications such as Allopurinol with such severe side effects that include a mortality risk. This risk is particularly pertinent in patients such as case#1 with multiple severe drug reactions that threaten vital organs such false lupus drug reactions.

Uric acid is an anti-oxidant that is replaced by the innocuous antioxidant ascorbic acid.

The anti-oxidant ascorbic acid can be synthesized by the animal kingdom where as the anti-oxidant in uric acid is not present in animals helpful comparative biology in drug development.

Example 13

The Protective Use of Liquid Crystal Subject Composition Medication Therapy in Nuclear Radiation Treatment of Cancer Tissue protection against nuclear radiation, such as used in oncology or inadvertent nuclear radiation accidents or bioterrorism. It has been observed in approximately 100 controlled animal studies that the tissues have been protected by specifically, but not limited to, component No. 1, $NH_2$ and SH moieties.

Example 14

Direct Anti-Inflammatory Effect of Liquid Crystal on Inflamed Ileum, Obtained by Biopsy, and In Vitro Chemokine Tissue Studies Results showed reduced production of the pro-inflammatory cytokine IL-1B in ileitis, obtained by biopsy, by more than 80% in 24 hours of medication exposure. This reduction was significantly greater than that observed in normal intestinal tissue. The mean reduction of IL-1B 1248 pg/g compared with a mean reduction in a normal intestinal tissue sample of 200 pg/g.

Example 15

Bio-Terrorism Vaccine Protection Utilizing Oral Mucosal Delivery of Vaccine

In the experimental animal, oral mucosal delivery of vaccine was performed and found to produce equal antibody protection as vaccine administered by injection. Further patented and patent pending technology, including liquid crystal processing to remove allergenic and untoward pathogenic factors while increasing immunogenicity.

Example 16

Treatment of Tonsillar Cancer Anal, Cancer and Small Cell Lung Cancer

At the time of treatment, Patient 1 was an approximately 35 year old male diagnosed with tonsillar cancer. H is prognosis was determined to be poor. At the time of treatment, Patient 2 was an 81 year old male diagnosed with anal cancer having local dissemination. At the time of treatment, Patient 3 was an approximately 70 year old female diagnosed with intractable small cell lung cancer, with metastasis and cachexia. Patient 3 weighed approximately 90 lbs and complained of fatigue.

Patient 2 received a sterile non-pyrogenic composition of about 20% essential fatty acids (a mixture of linoleic and linolenic acid), 1.2% egg yolk phospholipid, and about 2% glycerin in water for injection. This composition is sold commercially as "Intralipid," and was obtained from Baxter Healthcare Corp. (Deerfield, Ill.). Intralipid is manufactured for Baxter Healthcare by Fresenius Kabi AB (Uppsala, Sweden). Five hundred milliliters of Intralipid was given intravenously three times a week for one week. Patients 1 and 3 received a similar composition called Liposyn (Abbot Laboratories) intravenously three times a week for one week. Patient 2 received 500 ml per dose and Patient 3 was administered only 250 ml per dose. Liposyn is a sterile, nonpyrogenic fat emulsion for intravenous administration, which contains about 10% safflower oil, 1.2% egg phosphatides and about 2.5% glycerin in water for injection.

Patients 1-3 showed an improvement in overall health, including an increase in energy and relief of the fatigue and listlessness characteristic of cancer and disseminated cancer. Clinical signs of disease were visibly lessened. Regarding Patient 1, the prognosis was so grave that any signs of recovery were unexpected. However, after one week of treatment, it was reported that the improvement in Patient 1 was so dramatic that health-care personnel had to verify the patient's name to be sure he was the same patient that had been admitted. Patient's 1 improvement continued throughout the entire course of treatment. Patient 2 was observed walking down the hall one month after treatment, and his gait was remarkably brisk in view of his age, and the extent and location of his anal cancer. Patient 3 suffered from the fatigue characteristic of cancer, particularly when complicated by metastasis and cachexia. However, 24 hours after administering the composition to Patient 3, her fatigue completely resolved, which was a completely unexpected result in a patient with such a poor prognosis. This complete clearance of fatigue was noted again, lasting for 24 hours, after administration of the next two doses.

Example 17

Treatment of Squamous Cell Cancer, Lung Adenocarcinoma, Metastatic Lung Cancer and Anal Cancer Patient 4 is a 57-year old male with squamous cell cancer of the hypopharynx. Within one week, this patient was given a single dose of 500 ml Intralipid (20%) and a single dose of 500 ml Intralipid (10%). After this treatment, the patient showed some clinical improvement in energy levels and a decrease in lassitude.

Patient 5 is a 74-year old female with adenocarcinoma of the lung. This patient received three 500 ml doses of Intralipid (20%) in one week, and showed moderately increased energy levels and a reduction in lassitude.

Patient 6 is an 81-year old male suffering from right upper lobe lung cancer with metastatic spread in cervical lymph nodes right to left. This patient received one-daily doses of 250 ml Intralipid (10%) for 3 consecutive days. Patient 6 showed marked improvement in energy levels and a more than 60% lessening of radiation treatment side effects.

Patient 7 is an adult male, 82-years old, suffering from anal cancer complicated by severe cachexia. At the time of treatment, this patient weighed approximately 144 lbs. Upon 3 times weekly dosing with 500 ml Intralipid (20%), the size of a superficial tumor in the anal/perianal area (initially 5 cm) was reduced 40% in size after three days of treatment. After five treatments, the enlarged inguinal lymph nodes returned to normal. One indication that local dissemination of the cancer had improved.

From clinical observations of these patients before, during and after treatment with the Intralipid and Liposyn compositions, it is believed that the improvement in their clinical condition was the direct result of administering the composition.

Example 18

Treatment of Crohn's Disease

A 73 year old female patient suffering from Crohn's disease (symptoms included diarrhea, constipation, severe bouts of abdominal pain and fever, G.I. bleeding, generalized aching, extreme fatigue, nausea, and food and dairy intolerance) was being treated with corticosteroids administered three times weekly. This patient was administered a composition comprising about 10.6 g Neocate infant formula containing L-amino acids and glycine; about 50-100 mg lecithin; about 12.5-40 mg phosphatidyl choline; about 1000 mg fish oil concentrate (Entero-coated Fish Oil, 180 mg EPA and 120 mg DHA, Leiner Health Products, LLC, Carson Calif.); VSL (*Biffidum bacterium breve, Lactobacillus acidophilus, B. bacterium longum, L. plantarum, B. bacterium infantis, L. baracaciae, Streptococcus thermophilus, L. bulgaricus*) and/or Digestive Formula two-phase digestive aid available from Life Plus International, Batesville, Ak. (1 tablet daily, contains pancreatin, pancreolipase, pepsin, amylase, papain, bromelain and lipase, betaine, *lactobacillus* microflora such as *L. salivarius, L. acidophilus*, L. dds-1, *L. bulgaricus* and *Biffidum bacteria*, bile, lecithin, peppermint leaf, aloe vera and beetroot), extracellular matrix components comprising collagen, proteoglycan aggregate complex of cartilage and chondroitin sulfate (bovine and/or shark cartilage, four 740 mg capsules, twice or more daily), 3 mg boron, microcrystalline hydroxyapaptite (4762 mcg supplied as "Boneup" from Jarrow Formulas, Los Angeles, Calif., of which 1000 mcg is Ca, 510 mcg is P, and 1514 mcg is protein, 500 mg magnesium oxide, 10 mg zinc monomethionate, 1 mg copper gluconate, 1 mg manganese citrate, 300 mg glucosamine, 200 mg Vitamin C, 500 IU of Vitamin D3, 100 mcg Vitamin K as menaquinone-7, 400 mcg folic acid, and 100 mcg Vitamin B12), 200 mcg selenium, an additional 500-1000 mcg Vitamin B12, and 5 ml (preferably at bedtime) daily to three times a week of cherry flavored potassium chloride oral solution U.S.P. 10% (HUMCO, Texarkana, Tex. 75501), which contains 20 mEq (1.5 g) of potassium chloride. At times, the patient was given the potassium chloride solution as much as 5 ml three times a day as much 15 ml two to three times a day. Clinical observation showed an amelioration of severe abdominal pain and diarrhea, a decrease in fatigue, and control of osteoporosis caused by steroid use, age and previous ovarectomy. Complete normality of sedimentation rate and C-reactive proteins was also observed. A recent mild myocardial infarction has prompted the addition of three 900 mg arginine capsules in addition to the above-listed components which, along with nitroglycerin patches, has served to reduce angina. A goiter present in the patient's neck has also been maintained at a manageable size, which has precluded the need for surgical removal of the goiter. It should be noted that, at time, the VSL is not swallowed, but only used as a mouth rinse because it can aggravate the patient's diarrhea. While the present invention has been described in connection with the described embodiments, it is understood that other similar embodiments may be used or modifications and additions made to the described embodiments for performing the same function without derivating therefrom. Therefore, the invention should not be limited to any single embodiment, but rather should be construed in breadth and scope in accordance with the recitation of the appended claims.

The following applications are hereby incorporated by reference in their entireties, including all figures, formulae, references, amino acid and nucleic acid sequences, and tables: Ser. No. 10/765,664, filed Jan. 26, 2004; 60/442,278, filed Jan. 24, 2003; 60/447,779, filed Feb. 13, 2003; 60/448,003, filed Feb. 18, 2003; 60/448,497, filed Feb. 19, 2003; 60/478,565, filed Jun. 12, 2003; 60/493,237, filed Aug. 6, 2003; 60/523,936, filed Nov. 21, 2003; Ser. No. 10/752,298, filed Jan. 5, 2004; 60/437,939, filed Jan. 3, 2003; Ser. No. 10/269,613, filed Oct. 11, 2002; 60/358,890, filed Feb. 22, 2002; 60/350,119, filed Nov. 9, 2001; Ser. No. 09/611,857, filed Jul. 7, 2000; Ser. No. 09/781,586, filed Feb. 9, 2001; Ser. No. 09/639,859, filed Aug. 16, 2000; Ser. No. 09/731,608, filed Dec. 7, 2000; 60/149,338, filed Aug. 17, 1999; U.S. Provisional Patent Application Ser. Nos. 60/577,120; filed Jun. 4, 2004, entitled "Pharmacology and Pharmacodynamic Rationale Sourcing of Q101 KC for Crohn's Disease and Pediatric Crohn's Disease", Leonard Girsh (Inventor) and; 60/557,584; filed Mar. 29, 2004; 60/550,797, filed Mar. 5, 2004; and 60/478,565, filed Jun. 12, 2004.

REFERENCES

1. Griffiths A M, Nguyen P, Smith C, MacMillan J H, Sherman P M. Growth and clinical course of children with Crohn's disease. Gut. 1993 July; 34(7): 939-43.
2. Thearle M, Horlick M, Bilezikian J P, Levy J, Gertner J M, Levine L S, Harbison M, Berdon W, Oberfield S E. Osteoporosis: an unusual presentation of childhood Crohn's disease. J Clin Endocrinol Metab. 2000 June; 85(6): 2122-6.
3. King R A. Pediatric inflammatory bowel disease. Child Adolesc Psychiatr Clin N Am. 2003 July; 12(3): 537-50.
4. Belli, D C, Seidman, E, Bouthillier, L, Weber, A M, Roy, C C, Pletinex, M, et al. Chronic intermittent elemental diet improves growth failure in children with Crohn's disease. Gastroenterol. 1988; 94:603-610.
5. Seidman E G, Roy C C, Weber A M, Morin C L. Nutritional therapy of Crohn's disease in childhood. Dig Dis Sci 1987; 32:82-8S.
6. Morin, C L, Roulet, M, Roy, C C, Weber, A. Continuous elemental enteral alimentation in children with Crohn's disease and growth failure. Gastroenterol. 1980; 79:1205-1210.
7. C O'Morain, A M Segal, A J Levi, and H B Valman. Elemental diet in acute Crohn's disease. Arch. Dis. Child. 1983; 58:44-47.
8. Teahon K, Bjarnason I, Pearson M, Levi A J. Ten years' experience with an elemental diet in the management of Crohn's disease. Gut. 1990; 31:1133-1137.
9. O'Morain C, Segal A W, Levi A J. Elemental diet as primary treatment of acute Crohn's disease: a controlled trial. Br Med J 1984; 288:1859-62.
10. O'Morain, C., A W Segal, and A J Levi. Elemental Diets in Treatment of Acute Crohn's Disease. Br Med J 1990; 281:1173-1175.
11. Teahon K, Smethurst P, Pearson M, Levi A J and Bjarnason I. The effect of elemental diet on intestinal permeability and inflammation in Crohn's disease. Gastroenterol. 1991; 101:84-8.
12. Sanderson I R, Boulton P, Menzies I, Walker-Smith J A. Improvement of abnormal lactulose/rhamnose permeability in active Crohn's disease of the small bowel by an elemental diet. Gut 1987; 28:1073-1076.
13. Riordan A M, Hunter J O, Cowan R E, Crampton J R, Davidson A R, Dickinson R J, et al. Treatment of Crohn's disease by exclusion diet: East Anglian multicentre controlled trial. Lancet 1993; 342:1131-4.
14. Belluzzi A, Brignola C, Campieri M, Pera A, Boschi S, Miglioli M. Effect of an enteric-coated fish oil preparation on relapses in Crohn's disease. N Engl J Med 1996; 334:1557-60.
15. Lorenz R, Weber P C, Szimnau P, Heldwein W, Strasser T, Loeschke K. Supplementation with n-3 fatty acids from fish oil in chronic inflammatory bowel disease: A randomized, placebo-controlled, double-blind cross-over trial. J Intern Med. Suppl. 1989; 225(731):225-232.
16. Belluzzi A, Brignola C, Campieri M, et al. Effects of new fish oil derivative on fatty acid phospholipid-membrane pattern in a group of Crohn's disease patients. Dig Dis Sci 1994; 39:2589-94.

17. Mate J, Castanos R, Garcia-Samaniego J, Pajares J M. Does dietary fish oil maintain the remission of Crohn's disease (CD): a study case control. Gastroenterol. 1993; 100:A-228(abstr).
18. Prudden J F, Allen J. The clinical acceleration of healing with a cartilage preparation. JAMA 1965; 192(5):352-356.
19. Houck J C, Jacob R A, DeAngelo L, et al.: The inhibition of inflammation and the acceleration of tissue repair by cartilage powder. Surgery 1962; 51:632-38.
20. Prudden J F, Nishihara G, Baker L. The acceleration of wound healing with cartilage-I. Surg Gynecol Obstet. 1957; 105:283-287.
21. Biochemistry, (2000) Third Edition, C K Mathews, K E van Holde and K G Ahern. 303-4.
22. Bleichner G, Bléhaut H, Mentec H, Moyse D. *Saccharomyces boulardii* prevents diarrhea in critically ill tube-fed patients. A multicenter, randomized double-blind placebo-controlled trial. Intens Care Med 1997; 23:517-523.
23. United States Census Bureau, National Population Estimates (by Age) (http://eire.census.gov/popest/data/national/tables/asro/NA-EST2002-ASRO-01.php).
24. Cosgrove, M. The epidemiology of pediatric inflammatory bowel disease. Arch Dis Child 1996 (74/Suppl.); 5:460-61.
25. Hildebrand, H., Brydolf, M. Holmquist, L., Krantz, I., Kristiansson, B. Incidence and prevalence of inflammatory bowel disease in children in south-western Sweden. Acta Paedoatr 1994 (83/Suppl.); 6:640-45.

I claim:
1. A therapeutic composition for enhancing protein synthesis in a damaged or diseased tissue in a human, the composition comprising:
   a) at least one extracellular matrix compound selected from glycosaminoglycan, proteoglycan aggregate complex of hyaluronic acid, extracellular matrix protein and chondroitin in an amount effective as an anti-neo-inflammatory and anti-neo-angiogenetic agent in the damaged or diseased tissue;
   b) about one to three grams of at least one polar surface active lipid selected from the group consisting of phosphatidic acid, phosphatidylethanolamine, lecithin, phosphatidylserine, phosphatidylinositol, 2-lysolecithin, plasmalogen, choline plasmalogen, phostidylglycerol, diphosphatidylglycerol, sphingomyelin, and any combination of 2, 3, 4, 5, 6, 7, 8, 9, 10, or 11 of said polar active surface lipids;
   c) a plurality of enantiomerically pure L-amino acids and glycine of about 9 to 25 grams in a molar ratio that is representative of the molar ratio of amino acids in a normal human tissue corresponding to the damaged or diseased tissue;
   d) a component selected from the group consisting of Polyoxyethylene Sorbitan Monooleate, Sorbitan monooleate, grape seed extract, grape extract, and combinations thereof; and
   e) vitamins, minerals or trace elements selected from the group consisting of Vitamin B12, Vitamin E, selenium, zinc, and combinations thereof.

SEQUENCE LISTING

<160> NUMBER OF SEQ ID NOS: 1

<210> SEQ ID NO 1
<211> LENGTH: 153
<212> TYPE: PRT
<213> ORGANISM: Homo sapiens

<400> SEQUENCE: 1

```
Gly Leu Ser Asp Gly Glu Trp Gln Leu Val Leu Asn Val Trp Gly Lys
1               5                   10                  15

Val Glu Ala Asp Ile Pro Gly His Gly Gln Glu Val Leu Ile Arg Leu
                20                  25                  30

Phe Lys Gly His Pro Glu Thr Leu Glu Lys Phe Asp Lys Phe Lys His
            35                  40                  45

Leu Lys Ser Glu Asp Glu Met Lys Ala Ser Glu Asp Leu Lys Lys His
    50                  55                  60

Gly Ala Thr Val Leu Thr Ala Leu Gly Gly Ile Leu Lys Lys Lys Gly
65                  70                  75                  80

His His Glu Ala Glu Thr Lys Pro Leu Ala Gln Ser His Ala Thr Lys
                85                  90                  95

His Lys Ile Pro Val Lys Tyr Leu Glu Phe Ile Ser Glu Cys Ile Ile
            100                 105                 110

Gln Val Leu Gln Ser Lys His Pro Gly Asp Phe Gly Ala Asp Ala Gln
        115                 120                 125

Gly Ala Met Asn Lys Ala Leu Glu Leu Phe Arg Lys Asp Met Ala Ser
    130                 135                 140

Asn Tyr Lys Glu Leu Gly Phe Gln Gly
145                 150
```

2. The composition of claim 1, further comprising one or more compound(s) generally accepted as safe (GRAS) selected from the group consisting of aspartame perfluorocarbon resins, perfluorocarbon cured elastomers, [alpha]-Amylase enzyme preparation from *Bacillus stearothermophilus*, benzoic acid, bromelain, catalase, lactic acid, linoleic acid, potassium acid tartrate, propionic acid, stearic acid, tartaric acid, diacetyl tartaric acid esters of mono- and diglycerides, ammonium bicarbonate, ammonium carbonate, ammonium chloride, ammonium hydroxide, ammonium citrate, dibasic, ammonium phosphate, monobasic; ammonium phosphate, dibasic; bacterially-derived carbohydrase enzyme preparation; bacterially-derived protease enzyme preparation; bentonite; benzoyl peroxide; n-Butane; isobutane; Calcium glycerophosphate; Calcium lactate; Calcium pantothenate; Calcium propionate; Calcium stearate; Carbon dioxide; Beta-carotene; Cellulase enzyme preparation derived from *Trichoderma longibrachiatum*; Clove and its derivatives; Cocoa butter substitute; Copper gluconate; Copper sulfate; L-Cysteine; L-Cysteine monohydrochloride; Dextrin; Diacetyl; Enzyme-modified fats; Ethyl alcohol; Ficin; Glucono delta-lactone; Corn gluten; Wheat gluten; Glyceryl monooleate; Glyceryl behenate; Glyceryl palmitostearate; Helium; Inositol; Insoluble glucose isomerase enzyme preparations; Isopropyl citrate; Animal lipase; Magnesium carbonate; Magnesium chloride; Magnesium hydroxide; Magnesium oxide; Magnesium phosphate; Magnesium stearate; Magnesium sulfate; Malt; Malt syrup (malt extract); Manganese chloride; Manganese citrate; Manganese gluconate; Manganese sulfate; Microparticulated protein product; Mono- and diglycerides; Monosodium phosphate derivatives of mono- and diglycerides; Niacin; Niacinamide; Nickel; Nitrogen; Nitrous oxide; Peptones; Pancreatin; Papain; Pectins; Pepsin; Potassium bicarbonate; Potassium carbonate; Potassium chloride; Potassium hydroxide; Potassium lactate; Propane; Pyridoxine hydrochloride; Rennet (animal-derived) and chymosin preparation (fermentation-derived); Riboflavin; Riboflavin-5'-phosphate (sodium); Sodium benzoate; Sodium carbonate; Sodium hydroxide; Sodium hypophosphite; Sodium lactate; Sodium metasilicate; Sodium propionate; Sodium sesquicarbonate; Sodium tartrate; Sodium potassium tartrate; Starter distillate; Stearyl citrate; Thiamine hydrochloride; Thiamine mononitrate; [alpha]-Tocopherols; Triacetin; Tributyrin; Triethyl citrate; Trypsin; Urease enzyme preparation from *Lactobacillus fermentum*; Vitamin A; Vitamin B12; Candelilla wax; Carnauba wax; Baker's yeast extract; Zein; Sulfamic acid; Clay (kaolin); Ferric oxide; Iron oxides; Japan wax; Tall oil; Alfalfa; Allspice; Almond, bitter (free from prussic acid); Ambrette; *Angelica* root; *Angelica* seed or stem; Angostura; Anise; Asafetida; Balm; Balsam of Peru; Basil; Bay leaves; Bay; Bergamot (bergamot orange); Bois de rose; Cacao; Camomile (chamomile); *Capsicum*; Caraway; Cardamom seed (cardamon); Carob bean; Carrot; Cascarilla bark; *Cassia* bark, Chinese; *Cassia* bark, Padang or Batavia; *Cassia* bark, Saigon; Celery seed; Cherry, wild, bark; Chervil; Chicory; Cinnamon bark, Ceylon; Cinnamon bark, Chinese; Cinnamon bark, Saigon; Cinnamon leaf, Ceylon; Cinnamon leaf, Chinese; Cinnamon leaf, Saigon; Citronella; Citrus peels; Clary (clary sage); Clove bud; Clove leaf; Clove stem; Clover; Coca; Coffee; Cola nut; Coriander; Corn silk; Cumin (cummin); Curacao orange peel; Cusparia bark; Dandelion; Dandelion root; Dill; Dog grass (quackgrass, *triticum*); Elder flowers; Estragole; Estragon (tarragon); Fennel, sweet; Fenugreek; Galanga (galangal); Garlic; Geranium; Geranium, East Indian Geranium, rose; Ginger; *Glycyrrhiza*; Glycyrrhizin, ammoniated; Grapefruit; Guava; Hickory bark; Horehound (hoarhound); Hops; Horsemint; Hyssop; Immortelle; Jasmine; Juniper (berries); Kola nut; Laurel berries; Laurel leaves; Lavender; Lavender, spike; Lavandin; Lemon; Lemon balm (see balm); Lemon grass; Lemon peel; Licorice; Lime; Linden flowers; Locust bean; Lupulin; Mace; Malt (extract); Mandarin; Marjoram, sweet; Mate 1; Menthol; Menthyl acetate; Molasses (extract); Mustard; Naringin; Neroli, bigarade; Nutmeg; Onion; Orange, bitter, flowers; Orange, bitter, peel; Orange leaf; Orange, sweet; Orange, sweet, flowers; Orange, sweet, peel; *Origanum*; Palmarosa; Paprika; Parsley; Pepper, black; Pepper, white; Peppermint Peruvian balsam; Petitgrain; Petitgrain lemon; Petitgrain mandarin or tangerine; Pimenta; Pimenta leaf; Pipsissewa leaves; Pomegranate; Prickly ash bark; Rose absolute; Rosa; Rose; Rose buds; Rose flowers; Rose fruit (hips); Rose geranium; Rose leaves; Rosemary; Rue; Saffron; Sage; St. John's bread; Savory, summer; Savory, winter; *Schinus molle*; Sloe berries; Spearmint; Spike lavender; Tamarind; Tangerine; Tannic acid; Tarragon; Tea; Thyme; *Triticum*; Tuberose; Turmeric; Vanilla; Violet flowers; Violet leaves; Violet leaves absolute; Wild cherry bark; Ylang-ylang; and Zedoary bark, or any combination of said compounds.

3. The composition of claim 1, further comprising a flavorant.

4. The composition of claim 3, wherein said flavorant is a fruit juice.

5. The composition of claim 4, wherein said fruit juice is tomato juice.

6. The composition of claim 1, wherein said amino acids are L-Leucine, L-Proline, L-Arginine, L-Valine, L-Aspartic Acid, L-Isoleucine, Glycine, L-Threonine, L-Tyrosine, L-Phenylalanine, L-Serine, L-Histidine, L-Alanine, L-Cystine, L-Tryptophan, L-Methionine, L-Glutamine, L-Glutamic Acid, L-asparagine, L-cysteine, L-Lysine, L-Taurine, and L-Carnitine.

7. The composition of claim 1, wherein said component (c) comprises Corn Syrup Solids, High Oleic Safflower Oil, Refined Vegetable Oil, L-Lysine L-Glutamate, Calcium Phosphate Dibasic, and less than 2% (by weight) of each of the following: L-Leucine, Tripotassium Citrate, L-Proline, L-Arginine, L-Valine, L-Aspartic Acid, L-Isoleucine, Glycine, L-Threonine, L-Tyrosine, L-Phenylalanine, L-Serine, L-Histidine, L-Alanine, Mono and Diglycerides, Sodium Chloride, L-Cystine, L-Tryptophan, Magnesium Acetate, L-Methionine, Potassium Chloride, Diacetyl Tartaric Acid Esters of Monoglycerides, L-Glutamine, Choline Bitartrate, L-Glutamic Acid, M-Inositol, L-Ascorbic Acid, Soy Lecithin, Tricalcium Phosphate, Ferrous Sulfate, Zinc Sulfate, L-Carnitine, Niacinamide, DL-alpha Tocopheryl Acetate, Calcium D-Pantothenate, Cupric Sulfate, Manganese Sulfate, Pyridoxine Hydrochloride, Vitamin A Acetate, Riboflavin, Thiamine Chloride Hydrochloride, Potassium Iodide, Chromium Sulfate, Phylloquinone, Sodium Molybdate, Folic Acid, Sodium Hydrogen Selenite, D-Biotin, Vitamin $D_3$ and Cyanocobalamin.

8. The composition of claim 7, wherein said composition further comprises taurine.

9. A method of treating Crohn's disease comprising the administration of a composition according to claim 1 to an individual in an amount effective to alleviate symptoms associated with Crohn's disease.

* * * * *